US010471163B2

(12) United States Patent
Loving et al.

(10) Patent No.: US 10,471,163 B2
(45) Date of Patent: Nov. 12, 2019

(54) ACTIVATABLE FIBRIN-BINDING PROBES

(71) Applicant: The General Hospital Corporation, Boston, MA (US)

(72) Inventors: Galen Loving, Berkeley, CA (US); Peter D. Caravan, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 256 days.

(21) Appl. No.: 14/917,733

(22) PCT Filed: Sep. 12, 2014

(86) PCT No.: PCT/US2014/055508
§ 371 (c)(1),
(2) Date: Mar. 9, 2016

(87) PCT Pub. No.: WO2015/038968
PCT Pub. Date: Mar. 19, 2015

(65) Prior Publication Data
US 2016/0346411 A1    Dec. 1, 2016

Related U.S. Application Data

(60) Provisional application No. 61/877,325, filed on Sep. 13, 2013, provisional application No. 61/879,278, filed on Sep. 18, 2013.

(51) Int. Cl.
*A61K 51/00*    (2006.01)
*A61M 36/14*    (2006.01)
*A61K 51/08*    (2006.01)
*A61K 49/00*    (2006.01)
*A61K 49/14*    (2006.01)
*C07K 7/08*     (2006.01)

(52) U.S. Cl.
CPC ........ *A61K 51/088* (2013.01); *A61K 49/0056* (2013.01); *A61K 49/14* (2013.01); *A61K 51/08* (2013.01); *C07K 7/08* (2013.01)

(58) Field of Classification Search
CPC ...... A61K 51/00; A61K 51/08; A61K 51/088; A61K 38/00; A61K 2121/00; A61K 2123/00; A61K 49/00; A61K 49/14; A61K 49/0056; C07K 7/08
USPC .......... 424/1.11, 1.65, 1.69, 1.81, 1.85, 1.89, 424/9.1, 9.2, 9.3, 9.4, 9.5, 9.6; 514/1, 514/1.1; 530/300; 534/7, 10–16
See application file for complete search history.

(56) References Cited

U.S. PATENT DOCUMENTS

| 4,427,646 A | 1/1984 | Olexa et al. |
| 4,816,561 A * | 3/1989 | Todaro ............. C07K 7/08 530/324 |
| 4,899,755 A | 2/1990 | Lauffer et al. |
| 6,217,846 B1 | 4/2001 | Stuttle |
| 6,299,857 B1 | 10/2001 | Elmaleh et al. |
| 6,991,775 B2 | 1/2006 | Koerner et al. |
| 7,238,341 B2 | 7/2007 | Zhang et al. |
| 2008/0254036 A1 | 10/2008 | Sinha et al. |

FOREIGN PATENT DOCUMENTS

| EP | 0 063 002 | 10/1982 |
| EP | 0 869 820 | 3/2005 |
| WO | WO 86/06605 | 11/1986 |
| WO | WO 91/03200 | 3/1991 |
| WO | WO 95/28179 | 10/1995 |
| WO | WO 96/17628 | 6/1996 |
| WO | WO 96/23524 | 8/1996 |
| WO | WO 96/23526 | 8/1996 |
| WO | WO 97/18841 | 5/1997 |
| WO | WO 98/18495 | 5/1998 |
| WO | WO 98/18496 | 5/1998 |
| WO | WO 98/18497 | 5/1998 |
| WO | WO 98/18498 | 5/1998 |
| WO | WO 98/47538 | 10/1998 |
| WO | WO 98/57666 | 10/1998 |
| WO | WO 98/53857 | 12/1998 |
| WO | WO 2001/009188 | 2/2001 |
| WO | WO 2008/071679 | 6/2008 |

OTHER PUBLICATIONS

International Search Report and Written Opinion dated Jan. 21, 2015 in international application No. PCT/US2014/055508.
Altschul et al. "Gapped BLAST and PSI_BLAST: a new generation of protein database search programs," Nucleic Acids Res., 1997, 25(17):3389-3402.
Ay et al., "In Vivo Molecular Imaging of Thrombosis and Thrombolysis Using a Fibrin-Binding Positron Emission Tomographic Probe," Circ. Cardiovasc. Imaging, 2014, 7: 697-705.
Berge et al., "Pharmaceutical Salts," Journal of Pharmaceutical Science, Jan. 1977, 66: 1-19.
Blasi et al., "Effect of Chelate Type and Radioisotope on the Imaging Efficacy of 4 Fibrin-Specific PET Probes," J Nucl. Med., 2014, 55: 1157-1163.
Boros et al., "Pycup—A Bifunctional, Cage-like Ligand for 64Cu Radiolabeling," Molecular Pharmaceutics, 2014, 11(2): 617-629.
Ciesienski, et al., "Fibrin-Targeted PET Probes for the Detection of Thrombi," Molecular Pharmaceutics, 2013, 10(3): 1100-1110.
Hara et al., "Molecular Imaging of Fibrin Deposition in Deep Vein Thrombosis Using Fibrin-Targeted Near-Infrared Fluorescence," J Am. Coll. Cardiol Img.,2012, 5:607-615.
International Preliminary Report on Patentability, dated Mar. 24, 2016 in international application No. PCT/US2014/055508, 11 pages.

(Continued)

*Primary Examiner* — D. L. Jones
(74) *Attorney, Agent, or Firm* — Fish & Richardson P.C.

(57) ABSTRACT

Provided herein are methods for determining the presence or absence of active thrombus formation using a linear polypeptide that binds fibrin upon cyclization. Also provided are compounds comprising linear polypeptide probes that are cyclized in the presence of protein disulfide isomerase.

2 Claims, 23 Drawing Sheets

Specification includes a Sequence Listing.

(56) References Cited

OTHER PUBLICATIONS

Kolodziej et. al., "Fibrin Specific Peptides Derived by Phage Display: Characterization of Peptides and Conjugates for Imaging," Bioconjug. Chem, 2012, 23(3): 548-556.
Kurz, et al.,"Rat model of arterial thrombosis induced by ferric chloride," Thrombosis Research, Nov. 1990, 60(4): 269-280.
Merrifield, "Solid Phase Peptide Synthesis. I. The Synthesis of a Tetrapeptide," J. Am. Chem. Soc., 1963, 85(14):2149-2154.
Moskowitz and Budzynski, "The (DD)E Complex Is Maintained by a Composite Fibrin Polymerization Site," Biochemistry, 1994, 33: 12937-12944.
Olexa et al., "Structure of fragment E species from human cross-linked fibrin," Biochemistry, 1981, 20(21): 6139-6145.
Overoye-Cha, et al., "EP-2104R: A Fibrin-Specific Gadolinium-Based MRI Contrast Agent for Detection of Thrombus," J Am. Chem. Soc., 2008, 130(18): 6025-6039.
Sirol et al., "Fibrin-targeted contrast agent for improvement of in vivo acute thrombus detection with magnetic resonance imaging Atherosclerosis," Sep. 2005, 182(1): 79-85.
Spraggon et al., "Crystal structures of fragment D from human fibrinogen and its crosslinked counterpart from fibrin," Nature, 1997, 389: 455-462.
Starmans et al., "SPECT imaging of fibrin using fibrin-binding peptides," Contrast Media & Mol Imaging, May-Jun. 2013, 8(3): 229-237.
Uppal et al., "Molecular imaging of fibrin in a breast cancer xenograft mouse model," Invest Radial., 2012; 47(10):553-8.

* cited by examiner

RC  LC

Ipsi:contra ratio = 5.3

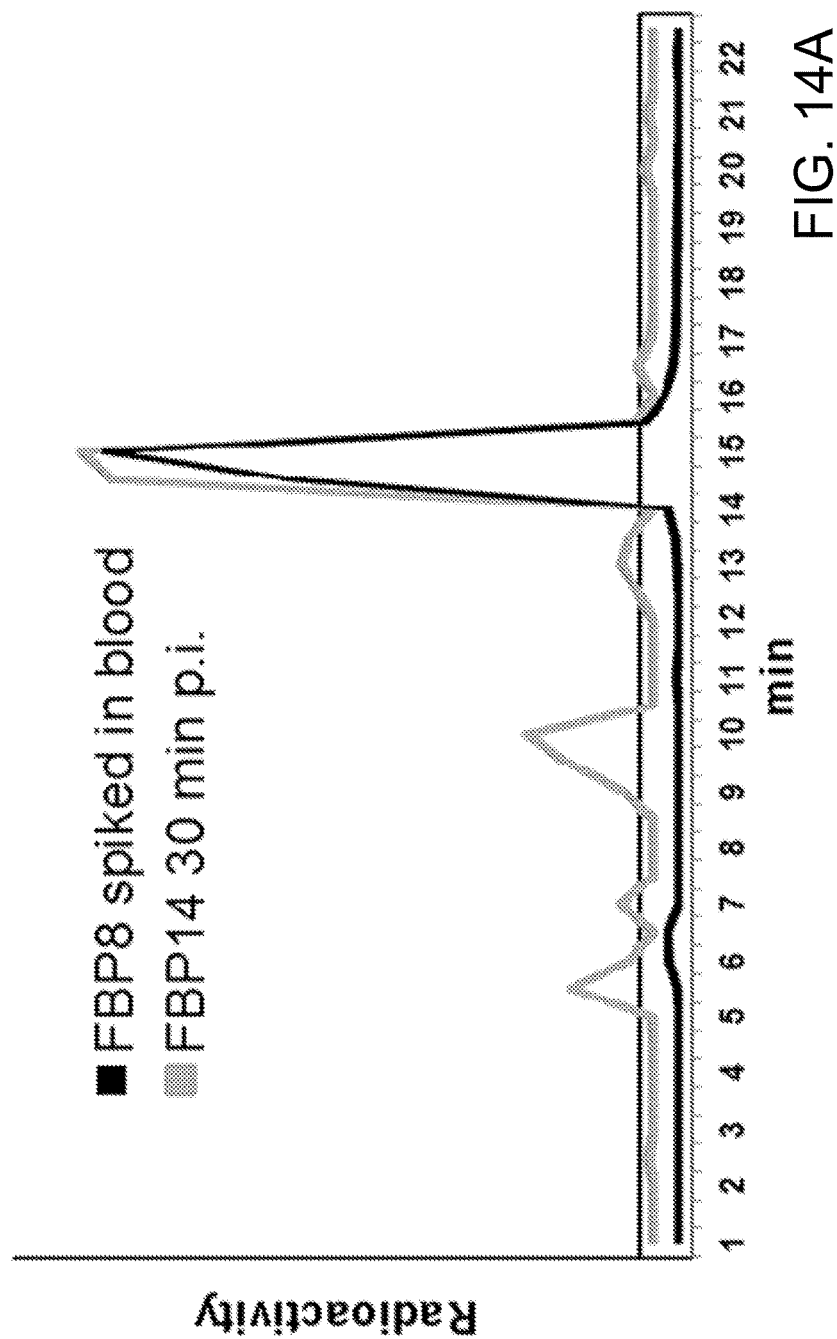

ACTIVATABLE FIBRIN-BINDING PROBES

CROSS-REFERENCE TO RELATED APPLICATIONS

This application is a U.S. National Phase Application under 35 U.S.C. § 371 of International Patent Application No. PCT/US2014/055508, filed on Sep. 12, 2014, which claims priority to U.S. Provisional Application Ser. Nos. 61/877,325, filed Sep. 13, 2013, and 61/879,278, filed Sep. 18, 2013, all of which are incorporated by reference in their entireties.

FEDERALLY SPONSORED RESEARCH OR DEVELOPMENT

This invention was made with Government support under Grant No. HL109448, awarded by the National Institutes of Health. The Government has certain rights in the invention.

TECHNICAL FIELD

This disclosure relates to probes useful for determining the presence or absence of an active thrombus and more particularly to linear polypeptide probes that are cyclized in the presence of protein disulfide isomerase.

BACKGROUND

Blood clot formation resulting in the complete occlusion of a blood vessel (thrombosis) often leads to serious life threatening events such as stroke and heart attack. The composition of a thrombus changes as it matures and exhibits variations in, for example, activated platelets, which play a role in mediating both thrombus formation and the wound healing process.

SUMMARY

The present application provides, inter alia, a method for determining the presence or absence of active thrombus formation in a subject, the method comprising:
administering to the subject an effective amount of a compound of Formula (I):

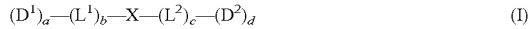
$$(D^1)_a—(L^1)_b—X—(L^2)_c—(D^2)_d \quad\quad (I)$$

or a pharmaceutically acceptable salt thereof,
wherein:
X is a linear polypeptide comprising at least two disulfide moieties, wherein upon cyclization of the at least two disulfide moieties, the resulting cyclized polypeptide is capable of binding to fibrin;
each $D^1$ is independently a detectable agent;
each $D^2$ is independently a detectable agent;
$L^1$ is a linker;
$L^2$ is a linker;
a is an integer from 0 to 4;
b is 0 or 1;
wherein if a is 0, b is 0;
c is 0 or 1;
d is an integer from 0 to 4;
wherein if d is 0, c is 0;
wherein at least one of a and d is an integer from 1 to 4;
and
detecting the presence of the reaction product of the compound of Formula (I) and a protein disulfide isomerase, wherein the presence of the reaction product indicates the presence of active thrombus formation in the subject.

The present application further provides a method for imaging a thrombus containing activated platelets in a subject, the method comprising:
administering to the subject an effective amount of a compound of Formula (I):

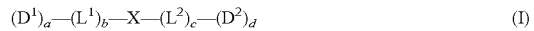
$$(D^1)_a—(L^1)_b—X—(L^2)_c—(D^2)_d \quad\quad (I)$$

or a pharmaceutically acceptable salt thereof,
wherein:
X is a linear polypeptide comprising at least two disulfide moieties, wherein upon cyclization of the at least two disulfide moieties, the resulting cyclized polypeptide is capable of binding to fibrin;
each $D^1$ is independently a detectable agent;
each $D^2$ is independently a detectable agent;
$L^1$ is a linker;
$L^2$ is a linker;
a is an integer from 0 to 4;
b is 0 or 1;
wherein if a is 0, b is 0;
c is 0 or 1;
d is an integer from 0 to 4;
wherein if d is 0, c is 0;
wherein at least one of a and d is an integer from 1 to 4;
and
imaging the reaction product of the compound of Formula (I) and a protein disulfide isomerase, wherein the reaction product is bound to the thrombus.

The present application further provides a method of treating a subject, the method comprising:
administering to the subject an effective amount of a compound of Formula (I):

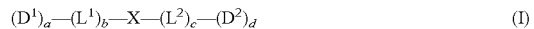
$$(D^1)_a—(L^1)_b—X—(L^2)_c—(D^2)_d \quad\quad (I)$$

or a pharmaceutically acceptable salt thereof,
wherein:
X is a linear polypeptide comprising at least two disulfide moieties, wherein upon cyclization of the at least two disulfide moieties, the resulting cyclized polypeptide is capable of binding to fibrin;
each $D^1$ is independently a detectable agent;
each $D^2$ is independently a detectable agent;
$L^1$ is a linker;
$L^2$ is a linker;
a is an integer from 0 to 4;
b is 0 or 1;
wherein if a is 0, b is 0;
c is 0 or 1;
d is an integer from 0 to 4;
wherein if d is 0, c is 0;
wherein at least one of a and d is an integer from 1 to 4;
b) detecting the presence of the reaction product of the compound of Formula (I) and a protein disulfide isomerase, wherein the presence of the reaction product indicates the presence of active thrombus formation in the subject;
c) identifying a subject who has active thrombus formation; and
d) selecting for the identified subject a treatment comprising an anti-thrombotic.

In some embodiments, the anti-thrombotic treatment comprises surgical intervention or administration of an anticoagulant or coagulation inhibitory agent, an anti-platelet or platelet inhibitory agent, a thrombin inhibitor, a thrombolytic or fibrinolytic agent, or an anti-inflammatory or NSAID agent. In some embodiments, the anti-coagulant or coagulation inhibitory agent is selected from the group consisting of heparin, sodium crystalline clathrate, and warfarin. In some embodiments, the anti-platelet or platelet inhibitory agent is selected from the group consisting of asprin, piroxicam, and ticlopidine. In some embodiments, the thrombin inhibitor is selected from the group consisting of a boropeptide, hirudin, and argatroban. In some embodiments, the thrombolytic or fibrinolytic agent is selected from the group consisting of a plasminogen activator, anistreplase, urokinase, and streptokinase. In some embodiments, the anti-inflammatory or NSAID agent is aspirin or ibuprofen.

In some embodiments, each disulfide moiety of X is a group of Formula (A):

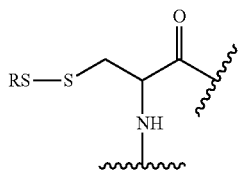

(A)

wherein each R is independently selected from the group consisting of $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-7 membered heterocycloalkyl, 4-10 membered heteroaryl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{a1}$, $NR^{c1}C(=O)OR^{b1}$, $NR^{c1}C(=O)NR^{c1}R^{d1}$, $C(=NR^{e})R^{b1}$, $C(=NR^{e})NR^{c1}R^{d1}$, $NR^{c1}C(=NR^{e})NR^{c1}R^{d1}$, $NR^{c1}S(=O)R^{b1}$, $NR^{c1}S(=O)_2NR^{c1}R^{d1}$; wherein the $C_{1-6}$ alkyl, $C_{6-10}$ aryl, 4-7 membered heterocycloalkyl, and 4-7 membered heteroaryl groups are each optionally substituted with 1, 2, or 3 independently selected $R^A$ groups;

each $R^A$ is independently selected from the group consisting of OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$alkylsulfonyl, carbamyl, $C_{1-3}$ alkylcarbamyl, di($C_{1-3}$alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$alkyl)aminocarbonylamino;

each $R^{a1}$, $R^{b1}$, $R^{c1}$, and $R^{d1}$ is independently selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-7 membered heterocycloalkyl, and 4-10 membered heteroaryl.

In some embodiments, each R is independently selected from the group consisting of a non-natural cysteine residue, a non-natural derivative of cysteine (e.g., penicillamine), $C_{6-10}$ aryl (e.g., phenyl), and 4-10 membered heteroaryl. In some embodiments, each R is independently selected from the group consisting of a non-natural cysteine residue, penicillamine, phenyl, 2-pyridine, 3-pyridine, and 4-pyridine.

In some embodiments, each disulfide moiety of X is selected from the group consisting of:

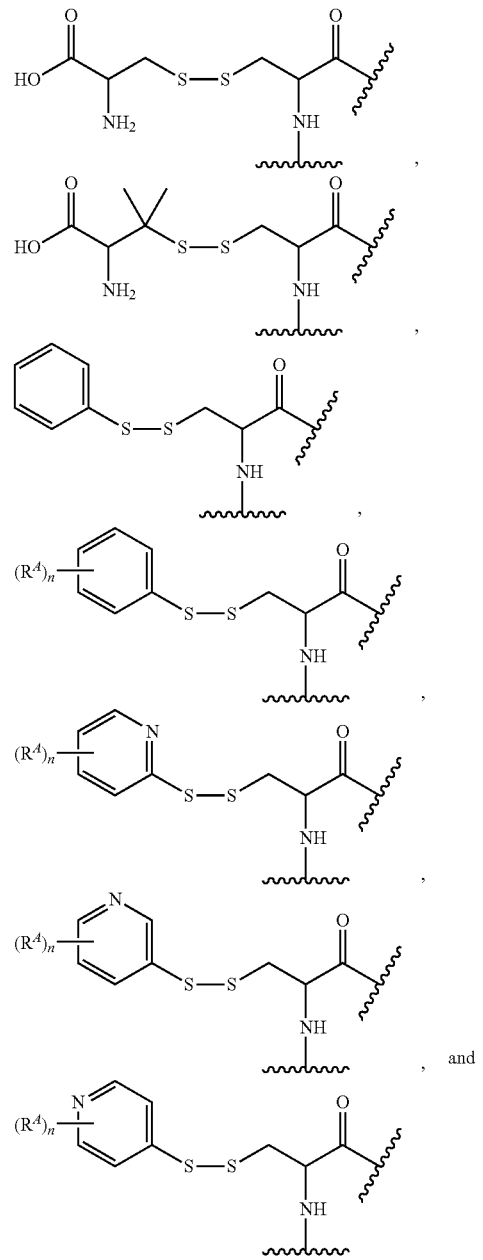

each $R^A$ is independently selected from the group consisting of OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$alkylsulfonyl, carbamyl, $C_{1-3}$ alkylcarbamyl, di($C_{1-3}$alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl) aminosulfonylamino, aminocarbonylamino, $C_{1-3}$ alkylaminocarbonylamino, and di($C_{1-3}$alkyl)aminocarbonylamino;

each $R^{a1}$, $R^{b1}$, $R^{c1}$, and $R^{d1}$ is independently selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-7 membered heterocycloalkyl, and 4-10 membered heteroaryl; and n is an integer from 1 to 3.

In some embodiments, X is a linear polypeptide comprising a sequence having at least 80% sequence identity to a sequence selected from the group consisting of:

(SEQ ID NO: 1)
W-Q-P-C*-P-W-E-S-W-T-F-C*-W-D-P (SEQ ID NO: 2)
W-Q-P-C*-P-A-E-S-W-T-F-C*-W-D-P (SEQ ID NO: 3)
G-P-P-G-W-Q-P-C*-P-W-E-S-W-T-F-C*-W-D-P (SEQ ID NO: 4)
G-G-R-G-W-Q-P-C*-P-W-E-S-W-T-F-C*-W-D-P (SEQ ID NO: 5)
G-W-Q-P-C*-P-W-E-S-W-T-F-C*-W-D-P (SEQ ID NO: 6)
S-G-S-G-T-W-Q-P-C*-P-W-E-S-W-T-F-C*-W-D-P (SEQ ID NO: 7)
W-Q-P-C*-P-W-E-S-W-T-Cha-C*-W-D-P (SEQ ID NO: 8)
W-Q-P-C*-P-W-E-S-W-T-Ffe4-C*-W-D-P (SEQ ID NO: 9)
W-Q-P-C*-P-W-E-S-W-T-F34fe-C*-W-D-P (SEQ ID NO: 10)
R-G-W-Q-P-C*-P-W-E-S-W-T-F-C*-W-D-P (SEQ ID NO: 11)
R-W-Q-P-C*-P-W-E-S-W-T-F-C*-W-D-P (SEQ ID NO: 12)
S-G-S-G-S-G-S-G-W-Q-P-C*-P-W-E-S-W-T-F-C*-W-D-P (SEQ ID NO: 13)
K-K-G-W-Q-P-C*-P-W-E-S-W-T-F-C*-W-D-P (SEQ ID NO: 14)
K-G-K-G-K-G-W-Q-P-C*-P-W-E-S-W-T-F-C*-W-D-P (SEQ ID NO: 15)
S(Galnac)-W-Q-P-C*-P-W-E-S-W-T-F-C*-W-D-P (SEQ ID NO: 16)
Thf2ca-W-Q-P-C*-P-W-E-S-W-T-F-C*-W-D-P (SEQ ID NO: 17)
R-R-G-G-W-Q-P-C*-P-W-E-S-W-T-F-C*-W-D-P (SEQ ID NO: 18)
S(Galnac)-T-W-Q-P-C*-P-W-E-S-W-T-F-C*-W-D-P (SEQ ID NO: 19)
W-Q-P-C*-Hvot4-W-E-S-W-T-F-C*-W-D-P (SEQ ID NO: 20)
G-P-P-G-W-Q-P-C*-P-A-E-S-W-T-F-C*-W-D-P (SEQ ID NO: 21)
G-G-R-G-W-Q-P-C*-P-A-E-S-W-T-F-C*-W-D-P (SEQ ID NO: 22)
K-K-G-W-Q-P-C*-P-A-E-S-W-T-F-C*-W-D-P (SEQ ID NO: 23)
K-G-K-G-K-G-W-Q-P-C*-P-A-E-S-W-T-F-C*-W-D-P (SEQ ID NO: 24)
G-W-Q-P-C*-P-A-E-S-W-T-F-C*-W-D-P (SEQ ID NO: 25)
S-G-S-G-S-G-S-G-W-Q-P-C*-P-A-E-S-W-T-F-C*-W-D-P -continued (SEQ ID NO: 26)
W-Q-P-C*-P-A-E-S-W-T-Ffe4-C*-W-D-P (SEQ ID NO: 27)
W-Q-P-C*-P-A-E-S-W-T-Cha-C*-W-D-P (SEQ ID NO: 28)
W-Q-P-C*-P-A-E-S-W-T-F34fe-C*-W-D-P (SEQ ID NO: 29)
Thf2ca-W-Q-P-C*-P-A-E-S-W-T-F-C*-W-D-P (SEQ ID NO: 30)
S-G-S-G-T-W-Q-P-C*-P-A-E-S-W-T-F-C*-W-D-P (SEQ ID NO: 31)
R-R-G-G-W-Q-P-C*-P-A-E-S-W-T-F-C*-W-D-P (SEQ ID NO: 32)
R-R-G-G-W-Q-P-C*-Hvot4-W-E-S-W-T-F-C*-W-D-P (SEQ ID NO: 33)
J-S-W-Q-P-C*-P-A-E-S-W-T-Cha-C*-W-D-P (SEQ ID NO: 34)
G-W-Q-P-C*-P-A-E-S-W-T-Cha-C*-W-D-P (SEQ ID NO: 35)
R-G-W-Q-P-C*-P-A-E-S-W-T-F-C*-W-D-P (SEQ ID NO: 36)
R-G-W-Q-P-C*-P-A-E-S-W-T-Cha-C*-W-D-P (SEQ ID NO: 37)
R-S-W-Q-P-C*-P-A-E-S-W-T-F-C*-W-D-P;

wherein C* is a group of Formula (A).

In some embodiments, X is a linear polypeptide comprising a sequence having at least 80% sequence identity to a sequence:

(SEQ ID NO: 38)
$X_1$-$X_2$-C*-P*-Y*-$X_3$-L-C*-$X_4$-$X_5$-$X_6$ wherein:

C* is a group of Formula (A);

P* is proline or a non-natural derivative thereof;

Y* is tyrosine or a non-natural derivative thereof;

$X_1$ is W, Y, F, S, Bip, Hx, Dpr, Cy, Gu, Ad, Hfe, 3-Pal, 4-Pal, DopaMe2, nY, dW, dF, F(3/4*), or Y(3*), wherein F(3/4*) is a phenylalanine substituted at either the 3 or the 4 position with a moiety such as $CH_3$, $CF_3$, $NH_2$, $CH_2NH_2$, CN, F, Cl, Br, I, Et, or Ome, and Y(3*) is a tyrosine substituted at the 3 position with a moiety such as F, Cl, Br, I, and $NO_2$;

$X_2$ is E, H, dE, S, H(Bzl), 2-Pal, Dpr, or Th;

$X_3$ is G or D;

$X_4$ is H, F, Y, or W;

$X_5$ is I, L, V, N, Bpa, Bal, Hfe, Nle, Tle, NV, Phg, Cha, Taz, Fua, Th, 4-Pal, or F(3/4*), wherein F(3/4*) is a phenylalanine substituted at either the 3 or the 4 position with a moiety such as $CF_3$, Et, iPr, or OMe; and $X_6$ is N, Q, I, L, or V, or not present. In some embodiments, at least one of $X_1$, $X_2$, $X_5$, P*, and Y* is a non-natural derivative of an amino acid. In some embodiments, P* is proline and Y* is a non-natural derivative of tyrosine, substituted at the 3 position by F, Cl, Br, I, or $NO_2$. In some embodiments, P* is 4-hydroxyproline and Y* is tyrosine.

In some embodiments, X is a linear polypeptide comprising a sequence having at least 80% sequence identity to a sequence selected from the group consisting of:

```
W-dE-C*-P(4-OH)-Y(3-Cl)-G-L-C*-W-I-Q                           (SEQ ID NO: 39)

Y-dE-C*-P(4-OH)-Y(3-Cl)-G-L-C*-Y-I-Q                           (SEQ ID NO: 40)

Y-dE-C*-P(4-OH)-Y(3-Cl)-G-L-C*-W-I-Q                           (SEQ ID NO: 41)

W-dE-C*-P(4-OH)-Y(3-Cl)-G-L-C*-Y-I-Q                           (SEQ ID NO: 42)

W-dE-C*-P(4-OH)-Y(3-Cl)-D-L-C*-W-I-Q                           (SEQ ID NO: 43)

Y-dE-C*-P(4-OH)-Y(3-Cl)-D-L-C*-Y-I-Q                           (SEQ ID NO: 44)

Y-dE-C*-P(4-OH)-Y(3-Cl)-D-L-C*-W-I-Q                           (SEQ ID NO: 45)

W-dE-C*-P(4-OH)-Y(3-Cl)-D-L-C*-Y-I-Q                           (SEQ ID NO: 46)

F(4-OMe)-H-C*-P(4-OH)-Y(3-Cl)-D-L-C*-H-I-L                     (SEQ ID NO: 47)

Y-H-C*-P(4-OH)-Y(3-Cl)-G-L-C*-W-I-Q                            (SEQ ID NO: 48)

W-dE-C*-P-Y(3-Cl)-G-L-C*-W-I-Q                                 (SEQ ID NO: 49)

W-dE-C*-P(4-OH)-Y-G-L-C*-W-I-Q                                 (SEQ ID NO: 50)

F-H-C*-P(4-OH)-Y(3-Cl)-D-L-C*-H-I-L                            (SEQ ID NO: 51)

F(4-OMe)-H-C*-P(4-OH)-Y(3-Cl)-D-L-C*-H-I                       (SEQ ID NO: 52)

F(4-OMe)-H-C*-P(4-OH)-Y(3-I)-D-L-C*-H-Bpa                      (SEQ ID NO: 53)

F-H-C*-P(4-OH)-Y(3-I)-D-L-C*-H-Hfe                             (SEQ ID NO: 54)

F-H-C*-P(4-OH)-Y(3-I)-D-L-C*-H-Bpa                             (SEQ ID NO: 55)

Y(3-Cl)-H-C*-P(4-OH)-Y(3-I)-D-L-C*-H-I                         (SEQ ID NO: 56)

F(4-OMe)-H-C*-P(4-OH)-Y(3-I)-D-L-C*-H-I-L                      (SEQ ID NO: 57)

F(4-OMe)-H(Bzl)-C*-P(4-OH)-Y(3-Cl)-D-L-C*-H-Bpa                (SEQ ID NO: 58)

F-H-C*-P(4-OH)-Y(3-Cl)-D-L-C*-H-I                              (SEQ ID NO: 59)

F(4-OMe)-H-C*-P(4-OH)-Y(3-I)-D-L-C*-H-I                        (SEQ ID NO: 60)

3Pal-H-C*-P(4-OH)-Y(3-I)-D-L-C*-H-I                            (SEQ ID NO: 61)

4Pal-H-C*-P(4-OH)-Y(3-I)-D-L-C*-H-I                            (SEQ ID NO: 62)

F(4-F)-H-C*-P(4-OH)-Y(3-I)-D-L-C*-H-I                          (SEQ ID NO: 63)

Y(3-I)-H-C*-P(4-OH)-Y(3-I)-D-L-C*-H-I                          (SEQ ID NO: 64)

F-H-C*-P(4-OH)-Y(3-I)-D-L-C*-H-I-L                             (SEQ ID NO: 65)

F(4-OMe)-H-C*-P(4-OH)-Y(3-Cl)-D-L-C*-H-Bpa-L                   (SEQ ID NO: 66)

F(4-OMe)-H-C*-P(4-OH)-Y(3-I)-D-L-C*-H-Bpa-L                    (SEQ ID NO: 67)

F-H(Bzl)-C*-P(4-OH)-Y(3-Cl)-D-L-C*-H-I-L                       (SEQ ID NO: 68)

1Nal-H-C*-P(4-OH)-Y(3-I)-D-L-C*-H-I                            (SEQ ID NO: 69)

MY-H-C*-P(4-OH)-Y(3-I)-D-L-C*-H-I                              (SEQ ID NO: 70)

F(4-OMe)-H(Bzl)-C*-P(4-OH)-Y(3-I)-D-L-C*-H-Bpa                 (SEQ ID NO: 71)

F(4-OMe)-H(Bzl)-C*-P(4-OH)-Y(3-Cl)-D-L-C*-H-I                  (SEQ ID NO: 72)

F-H-C*-P(4-OH)-Y(3-I)-D-L-C*-3Pal-I                            (SEQ ID NO: 73)

F(4-I)-H-C*-P(4-OH)-Y(3-I)-D-L-C*-H-I                          (SEQ ID NO: 74)

F(4-Br)-H-C*-P(4-OH)-Y(3-I)-D-L-C*-H-I                         (SEQ ID NO: 75)

F(4-Me)-H-C*-P(4-OH)-Y(3-I)-D-L-C*-H-I                         (SEQ ID NO: 76)

F(4-CF3)-H-C*-P(4-OH)-Y(3-I)-D-L-C*-H-I                        (SEQ ID NO: 77)

F(4-CN)-H-C*-P(4-OH)-Y(3-I)-D-L-C*-H-I                         (SEQ ID NO: 78)

Y(3-NO2)-H-C*-P(4-OH)-Y(3-I)-D-L-C*-H-I                        (SEQ ID NO: 79)

Y(2-F)-H-C*-P(4-OH)-Y(3-I)-D-L-C*-H-I                          (SEQ ID NO: 80)

F(4-CH2NH2)-H-C*-P(4-OH)-Y(3-I)-D-L-C*-H-I                     (SEQ ID NO: 81)

F(4-NH2)-H-C*-P(4-OH)-Y(3-I)-D-L-C*-H-I                        (SEQ ID NO: 82)

F(34-F2)-H-C*-P(4-OH)-Y(3-I)-D-L-C*-H-I                        (SEQ ID NO: 83)

DopaMe2-H-C*-P(4-OH)-Y(3-I)-D-L-C*-H-I                         (SEQ ID NO: 84)

F(2-OMe)-H-C*-P(4-OH)-Y(3-I)-D-L-C*-H-I                        (SEQ ID NO: 85)

F(3-Me)-H-C*-P(4-OH)-Y(3-I)-D-L-C*-H-I                         (SEQ ID NO: 86)

F-H-C*-P(4-OH)-Y(3-I)-D-L-C*-H-I                               (SEQ ID NO: 87)

F-H-C*-P(4-OH)-Y(3-I)-D-L-C*-H-F(3-CF3)                        (SEQ ID NO: 88)

F(3-CF3)-H-C*-P(4-OH)-Y(3-I)-D-L-C*-H-I                        (SEQ ID NO: 89)

F(3-OMe)-H-C*-P(4-OH)-Y(3-I)-D-L-C*-H-I                        (SEQ ID NO: 90)

Hfe-H-C*-P(4-OH)-Y(3-I)-D-L-C*-H-I                             (SEQ ID NO: 91)

nY-H-C*-P(4-OH)-Y(3-I)-D-L-C*-H-I                              (SEQ ID NO: 92)
```

(SEQ ID NO: 93)
W-E-C*-P(4-OH)-Y(3-Cl)-G-L-C*-W-I-Q (SEQ ID NO: 94)
F-H-C*-P(4-OH)-Y(3-I)-D-L-C*-H-I-L (SEQ ID NO: 95)
F(4-OMe)-H(Bzl)-C*-P(4-OH)-Y(3-I)-D-L-C*-H-I (SEQ ID NO: 96)
F-H-C*-P(4-OH)-Y(3-I)-D-L-C*-H-Nle (SEQ ID NO: 97)
F-H-C*-P(4-OH)-Y(3-I)-D-L-C*-H-Tle (SEQ ID NO: 98)
F-H-C*-P(4-OH)-Y(3-I)-D-L-C*-H-F(4-CF3)

(SEQ ID NO: 99)
F-H-C*-P(4-OH)-Y(3-I)-D-L-C*-H-Bip (SEQ ID NO: 100)
F-H-C*-P(4-OH)-Y(3-I)-D-L-C*-H-F(4-Et)

(SEQ ID NO: 101)
F-H-C*-P(4-OH)-Y(3-I)-D-L-C*-H-F(4-OMe)

(SEQ ID NO: 102)
F-H-C*-P(4-OH)-Y(3-I)-D-L-C*-H-F(3-OMe)

(SEQ ID NO: 103)
F(F5)-H-C*-P(4-OH)-Y(3-I)-D-L-C*-H-I (SEQ ID NO: 104)
F-H-C*-P(4-OH)-Y(3-F)-D-L-C*-H-I-L (SEQ ID NO: 105)
W-E-C*-P(4-OH)-Y(3-Cl)-G-L-C*-W-I-Q (SEQ ID NO: 106)
T-dE-C*-P(4-OH)-Y(3-Cl)-G-L-C*-W-I-Q (SEQ ID NO: 107)
F-H-C*-P-Y(3-Cl)-D-L-C*-H-I-L (SEQ ID NO: 108)
Y(26-Me)-H-C*-P(4-OH)-Y(3-I)-D-L-C*-H-I (SEQ ID NO: 109)
W-E-C*-P(4-OH)-Y(3-Cl)-G-L-C*-H-I-Q (SEQ ID NO: 110)
dF-dE-C*-P(4-OH)-Y(3-Cl)-G-L-C*-W-I-Q (SEQ ID NO: 111)
Y-E-C*-P(4-OH)-Y(3-Cl)-G-L-C*-Y-I-Q (SEQ ID NO: 112)
W-E-C*-P(4-OH)-Y(3-Cl)-G-L-C*-F-I-Q (SEQ ID NO: 113)
H-dE-C*-P(4-OH)-Y(3-Cl)-G-L-C*-W-I-Q (SEQ ID NO: 114)
F-H-C*-P(4-OH)-Y(3-I)-D-L-C*-H-I-L (SEQ ID NO: 115)
W-E-C*-P-Y-G-L-C*-W-I-Q (SEQ ID NO: 116)
F-H-C*-P(4-OH)-Y(3-I)-D-L-C*-H-nV (SEQ ID NO: 117)
F-H-C*-P(4-OH)-Y(3-I)-D-L-C*-H-Phg (SEQ ID NO: 118)
F-H-C*-P(4-OH)-Y(3-I)-D-L-C*-H-F(3-Me)

(SEQ ID NO: 119)
F-H-C*-P(4-OH)-Y(3-I)-D-L-C*-4Pal-I (SEQ ID NO: 120)
S-dE-C*-P(4-OH)-Y(3-Cl)-G-L-C*-W-I-Q (SEQ ID NO: 121)
W-E-C*-P(4-OH)-Y(3-Cl)-G-L-C*-Y-I-Q (SEQ ID NO: 122)
Y-E-C*-P(4-OH)-Y(3-Cl)-G-L-C*-W-I-Q (SEQ ID NO: 123)
F-dE-C*-P(4-OH)-Y(3-Cl)-G-L-C*-W-I-Q (SEQ ID NO: 124)
F-H-C*-P-Y-D-L-C*-H-I-L (SEQ ID NO: 125)
F-H-C*-P(4-OH)-Y(3-I)-D-L-C*-H-I-L (SEQ ID NO: 126)
F-H-C*-P(4-OH)-Y-D-L-C*-H-Bpa (SEQ ID NO: 127)
F-H-C*-P(4-OH)-Y(3-Cl)-G-L-C*-H-I-L (SEQ ID NO: 128)
S(Bzl)-H-C*-P-Y-D-L-C*-H-I-L (SEQ ID NO: 129)
H-E-C*-P(4-OH)-Y(3-Cl)-G-L-C*-H-I-Q (SEQ ID NO: 130)
F(4-OMe)-H-C*-P(4-OH)-Y-D-L-C*-H-I-L (SEQ ID NO: 131)
F-H-C*-P(4-OH)-Y(3-I)-D-L-C*-Bpa-I (SEQ ID NO: 132)
Ad-H-C*-P(4-OH)-Y(3-I)-D-L-C*-H-I (SEQ ID NO: 133)
F-H-C*-P(4-OH)-Y(3-Cl)-F-L-C*-H-I-L (SEQ ID NO: 134)
F-E-C*-P(4-OH)-Y(3-Cl)-G-L-C*-W-I-Q (SEQ ID NO: 135)
F-H-C*-P(4-OH)-Y(3-Cl)-2-Nal-L-C*-H-I-L (SEQ ID NO: 136)
F-H-C*-P(4-OH)-Y-D-L-C*-H-I-L (SEQ ID NO: 137)
Hfe-H-C*-P(4-OH)-Y-D-L-C*-H-I-L (SEQ ID NO: 138)
Bip-H-C*-P(4-OH)-Y-D-L-C*-H-I-L (SEQ ID NO: 139)
W-E-C*-P-Y-G-L-C*-W-I-Q (SEQ ID NO: 140)
F(4-OMe)-W-C*-P(4-OH)-Y(3-I)-D-L-C*-H-I (SEQ ID NO: 141)
F-H-C*-P(4-OH)-Y(3-I)-D-L-C*-2Pal-I (SEQ ID NO: 142)
F-H-C*-P(4-OH)-Y(3-I)-D-L-C*-Taz-I (SEQ ID NO: 143)
F-H-C*-P(4-OH)-Y(3-I)-D-L-C*-Dht-I,
and (SEQ ID NO: 144)
Gu-H-C*-P(4-OH)-Y(3-I)-D-L-C*-H-I.

In some embodiments, X is a linear polypeptide comprising a sequence having at least 80% sequence identity to a sequence:

```
                                            (SEQ ID NO: 145)
C*-P*-Y*-X1-L-C*
``` wherein $X_1$ is G or D;

C* is a group of Formula (A);

P* is proline or its non-natural derivative 4-hydroxyproline; and

Y* is tyrosine or a non-natural derivative of tyrosine substituted at the 3 position with a moiety selected from the group consisting of fluoro, chloro, bromo, iodo, and $NO_2$;

provided that at least one of P* or Y* is a non-natural derivative of the respective amino acid.

In some embodiments, X is a linear polypeptide comprising a sequence having at least 80% sequence identity to a sequence:

```
                                            (SEQ ID NO: 146)
C*-D-Y-Y-G-T-C*-X10
``` wherein:

C* is a group of Formula (A);

$X_{10}$ is selected from the group consisting of n(decyl)G, n(4-PhBu)G, MeL, Bpa, Bip, Me-Bip, F(4*), F(3-Me), F(3,4-difluoro), Amh, Hfe, Y(3,5-di-iodo), Pff, INal, dlNal, and MeL, wherein F(4*) is a phenylalanine substituted at the 4 position with a moiety selected from the group consisting of Et, $CF_3$, I, and iPr.

In some embodiments, X is a linear polypeptide comprising a sequence having at least 80% sequence identity to a sequence:

```
                                            (SEQ ID NO: 147)
X1-P*-C*-D-Y-Y-G-T-C*-X10-X11
``` wherein $X_1$ is any natural or non-natural amino acid,

C* is a group of Formula (A);

P* is proline or a non-natural derivative thereof, and wherein $X_{11}$ is selected from the group consisting of D, dD, βD, Inp, Nip, Me—D, dC, Cop, and Cmp.

In some embodiments, X is a linear polypeptide comprising a sequence having at least 80% sequence identity to a sequence selected from the group consisting of:

```
                                            (SEQ ID NO: 148)
L-P-C*-D-Y-Y-G-T-C*-n(Decyl)G-dD (SEQ ID NO: 149)
L-P-C*-D-Y-Y-G-T-C*-n(Decyl)G-D (SEQ ID NO: 150)
L-P-C*-D-Y-Y-G-T-C*-Bip-D (SEQ ID NO: 151)
L-P-C*-D-Y-Y-G-T-C*-Bip-dD (SEQ ID NO: 152)
L-P-C*-D-Y-Y-G-T-C*-MeL-Inp (SEQ ID NO: 153)
L-P-C*-D-Y-Y-G-T-C*-MeL-Cmp (SEQ ID NO: 154)
L-P-C*-D-Y-Y-G-T-C*-MeBip-D (SEQ ID NO: 155)
L-P*-C*-D-Y-Y-G-T-C*-n(Decyl)G-dD (SEQ ID NO: 156)
L-P*-C*-D-Y-Y-G-T-C*-n(Decyl)G-D (SEQ ID NO: 157)
L-P*-C*-D-Y-Y-G-T-C*-MeL-Inp (SEQ ID NO: 158)
L-P*-C*-D-Y-Y-G-T-C*-Bip-D (SEQ ID NO: 159)
L-P*-C*-D-Y-Y-G-T-C*-Bip-dD (SEQ ID NO: 160)
L-P*-C*-D-Y-Y-G-T-C*-Me-Bip-D (SEQ ID NO: 161)
L-P*-C*-D-Y-Y-G-T-C*-MeL-Cmp (SEQ ID NO: 162)
L-P*-C*-D-Y-Y-G-T-C*-L-D (SEQ ID NO: 163)
Cha-P*-C*-D-Y-Y-G-T-C*-Bip-D.
```

In some embodiments, X is a linear polypeptide comprising a sequence having at least 80% sequence identity to a sequence selected from the group consisting of:

```
                                            (SEQ ID NO: 164)
Y-dE-C*-P(4-OH)-3C-L-Y-G-L-C*-Y-I-Q (SEQ ID NO: 165)
R-W-Q-P-C*-P-A-E-S-W-T-Cha-C*-W-D-P (SEQ ID NO: 166)
R-W-Q-P-C*-P-A-E-S-W-T-Cha-C*-W-D-P-G-G-G-K.
```

In some embodiments, X is a linear polypeptide comprising a sequence having at least 80% sequence identity to a sequence:

```
                                            (SEQ ID NO: 167)
C*-X2-X3-Y-X5-X6-C*
``` wherein:

C* is a group of Formula (A);

$X_2$ is A, E, F, G, Ile, K, L, M, R, T, V, Y, N, D, Gln, H, S, or Tφ;

$X_3$ is S, F, A, or Y;

$X_5$ is G, A, or dA; and $X_6$ is T, V, or S. In some embodiments, (SEQ ID NO: 167) is: C*—$X_2$—$X_3$—Y—G—T—C* (SEQ ID NO: 168).

In some embodiments, X is a linear polypeptide comprising a sequence having at least 80% sequence identity to a sequence:

```
                                            (SEQ ID NO: 169)
X1-X2-C*-X4-X5-Y-X7-X8-C*-X10-X11
``` wherein:

C* is a group of Formula (A);

$X_1$ is R, D, H, L, or F;

$X_2$ is A, D, G, P, or S;

$X_4$ is A, E, F, G, Ile, K, L, M, R, T, V, Y, N, D, Gln, H, S, or Tφ;

$X_5$ is A, Y, F, or S;

$X_7$ is G, A, or dA;

$X_8$ is T, V, or S;

$X_{10}$ is H, L, or F; and $X_{11}$ is R, D, or H.

In some embodiments, X is a linear polypeptide comprising a sequence having at least 80% sequence identity to a sequence:

$$\text{C*-Y-}X_3\text{-S-Y-}X_6\text{-}X_7\text{-}X_8\text{-}X_9\text{-C*} \quad \text{(SEQ ID NO: 170)}$$

wherein:
C* is a group of Formula (A);
$X_3$ is N or D;
$X_6$ is G or Y;
$X_7$ is H or V;
$X_8$ is P or Tφ; and
and $X_9$ is Tφ or Y.

In some embodiments, X is a linear polypeptide comprising a sequence having at least 80% sequence identity to a sequence:

$$X_1\text{-}X_2\text{-}X_3\text{-C*-Y-}X_6\text{-S-Y-}X_9\text{-}X_{10}\text{-}X_{11}\text{-}X_{12}\text{-C*-}X_{14}\text{-}X_{15}\text{-}X_{16} \quad \text{(SEQ ID NO: 171)}$$

wherein:
$X_1$ is N or R;
$X_2$ is H or F;
$X_3$ is G or L;
C* is a group of Formula (A);
$X_6$ is N or D;
$X_9$ is G or Y;
$X_{10}$ is V or H;
$X_{11}$ is P or Tφ;
$X_{12}$ is Y or Tφ;
$X_{14}$ is D or S;
$X_{15}$ is Y or H;
and $X_{16}$ is S or H.

In some embodiments, X is a linear polypeptide comprising a sequence having at least 80% sequence identity to a sequence:

$$X_1\text{-}X_2\text{-C*-P-Y-}X_6\text{-L-C*-}X_9\text{-}X_{10}\text{-}X_{11} \quad \text{(SEQ ID NO: 172)}$$

wherein $X_1$ is Tφ, F, H, or Y;
$X_2$ is H, D, or E;
C* is a group of Formula (A);
$X_6$ is D, G, or A;
$X_9$ is H, F, Y, or Tφ;
$X_{10}$ is Ile, L, or V; and
$X_{11}$ is N, Gln, Ile, L, or V.

In some embodiments, X is a linear polypeptide comprising a sequence having at least 80% sequence identity to a sequence selected from the group consisting of:

R-S-C*-N-Y-Y-G-T-C*-L-H (SEQ ID NO: 173)

H-D-C*-Q-Y-Y-G-T-C*-L-H (SEQ ID NO: 174)

F-A-C*-H-Y-Y-G-T-C*-L-H (SEQ ID NO: 175)

R-P-C*-D-Y-Y-G-T-C*-F-D (SEQ ID NO: 176)

L-P-C*-D-Y-Y-G-T-C*-L-D (SEQ ID NO: 177)

F-S-C*-Tφ-Y-S-L-H-C*-H-R (SEQ ID NO: 178)

D-P-C*-S-Y-Y-G-T-C*-L-H (SEQ ID NO: 179)

L-P-C*-S-Y-Y-G-T-C*-L-H (SEQ ID NO: 180)

L-S-C*-D-Y-Y-G-T-C*-L-R (SEQ ID NO: 181)

L-A-C*-H-Y-Y-G-T-C*-L-H (SEQ ID NO: 182)

D-G-C*-H-Y-Y-G-T-C*-L-H (SEQ ID NO: 183)

R-P-C*-N-Y-Y-G-T-C*-L-H (SEQ ID NO: 184)

N-H-G-C*-Y-N-S-Y-G-V-P-Y-C*-D-Y-S (SEQ ID NO: 185)

R-F-L-C*-Y-D-S-Y-H-Tφ-Tφ-C*-S-H-H (SEQ ID NO: 186)

Tφ-F-H-C*-P-Y-D-L-C*-H-I-L (SEQ ID NO: 187)

Q-W-E-C*-P-Y-G-L-C*-Tφ-I-Q (SEQ ID NO: 188)

G-F-H-C*-P-Y-D-L-C*-H-I-L (SEQ ID NO: 189)

F-H-C*-P-Y-D-L-C*-H-I-L (SEQ ID NO: 190)

H-C*-P-Y-D-L-C*-H-I-L (SEQ ID NO: 191)

F-H-C*-P-Y-D-L-C*-H-I (SEQ ID NO: 192)

Tφ-E-C*-P-Y-G-L-C*-Tφ-I-Q (SEQ ID NO: 193)

E-C*-P-Y-G-L-C*-Tφ-I-Q (SEQ ID NO: 194)

Tφ-E-C*-P-Y-G-L-C*-Tφ-I (SEQ ID NO: 195)

P-C*-D-Y-Y-G-T-C*-L (SEQ ID NO: 196)

C*-D-Y-Y-G-T-C*-L (SEQ ID NO: 197)

C*-D-Y-Y-G-T-C* (SEQ ID NO: 198)

L-P-C*-D-Y-Y-D-A-T-C*-L-D (SEQ ID NO: 199)

L-A-C*-D-Y-Y-G-T-C*-L-D (SEQ ID NO: 200)

L-P-C*-A-Y-Y-G-T-C*-L-D (SEQ ID NO: 201)

L-P-C*-D-A-Y-G-T-C*-L-D (SEQ ID NO: 202)

L-P-C*-D-Y-A-G-T-C*-L-D (SEQ ID NO: 203)

L-P-C*-D-Y-Y-A-T-C*-L-D (SEQ ID NO: 204)

```
                                    (SEQ ID NO: 205)
L-P-C*-D-Y-Y-G-A-C*-L-D (SEQ ID NO: 206)
L-P-C*-D-Y-Y-G-T-C*-A-D (SEQ ID NO: 207)
L-P-C*-D-Y-Y-G-S-C*-L-D (SEQ ID NO: 208)
L-P-C*-D-Y-Y-G-V-C*-A-D (SEQ ID NO: 209)
G-F-H-C*-P-Y-D-L-C*-H-I-L (SEQ ID NO: 210)
F-H-C*-P-Y-D-L-C*-H-I-L (SEQ ID NO: 211)
H-C*-P-Y-D-L-C*-H-I-L (SEQ ID NO: 212)
F-H-C*-P-Y-D-L-C*-H-I (SEQ ID NO: 213)
W-E-C*-P-Y-G-L-C*-Tφ-I-Q (SEQ ID NO: 214)
E-C*-P-Y-G-L-C*-Tφ-I-Q
and (SEQ ID NO: 215)
W-E-C*-P-Y-G-L-C*-Tφ-I;
``` wherein C* is a group of Formula (A).

In some embodiments, X is a linear polypeptide comprising a sequence having at least 80% sequence identity to a sequence selected from the group consisting of:

```
                                    (SEQ ID NO: 216)
F-H-C*-P(4-OH)-Y(3-Cl)-D-L-C*-H-I-Q (SEQ ID NO: 217)
Y-D-E-C*-P(4-OH)-Y(3-Cl)-G-L-C*-Y-I-Q (SEQ ID NO: 218)
Q-W-E-C*-P-Y-G-L-C*-W-I-Q,
``` wherein C* is a group of Formula (A).

In some embodiments, X is a linear polypeptide comprising a sequence at least 80% identical to a sequence selected from the group consisting of:

```
                                    (SEQ ID NO: 51)
F-H-C*-P(4-OH)-Y(3-Cl)-D-L-C*-H-I-L
and (SEQ ID NO: 218)
Q-W-E-C*-P-Y-G-L-C*-W-I-Q
``` wherein C* is a group of Formula (A).

In some embodiments, each detectable agent independently comprises one or more groups independently selected from the group consisting of a radioactive isotope, a fluorescent material, a contrast agent, a luminescent material, and bioluminescent material. In some embodiments, each detectable agent independently comprises one or more groups independently selected from the group consisting of a radioactive isotope, a luminescent material, a contrast agent, or a mixture thereof.

In some embodiments, each detectable agent comprises a radioactive isotope. In some embodiments, each radioactive isotope is independently selected from the group consisting of $^{99m}$Tc, $^{51}$Cr, Al—$^{18}$F, $^{67}$Ga, $^{68}$Ga, $^{44}$Sc, $^{47}$Sc, $^{167}$Tm, $^{141}$Ce, $^{111}$In, $^{113}$In, $^{168}$Yb, $^{175}$Yb, $^{140}$La, $^{90}$Y, $^{86}$Y, $^{153}$Sm, $^{166}$Ho, $^{165}$Dy, $^{166}$Dy, $^{61}$Cu, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au, $^{111}$Ag, $^{199}$Au, $^{51}$Mn, $^{52m}$Mn, $^{52g}$Mn $^{52}$Fe, $^{60}$Cu, $^{72}$As, $^{94m}$Tc, $^{110}$In, $^{142}$Pr, $^{153}$Gd and $^{159}$Gd. In some embodiments, each radioactive isotope is independently selected from the group consisting of Al—$^{18}$F, $^{64}$Cu, $^{99m}$Tc, $^{68}$Ga, and $^{111}$In. In some embodiments, each radioactive isotope is Al—$^{18}$F. In some embodiments, each radioactive isotope is $^{64}$Cu. In some embodiments, each radioactive isotope is $^{99m}$Tc. In some embodiments, each radioactive isotope is $^{68}$Ga. In some embodiments, each radioactive isotope is $^{111}$In.

In some embodiments, each detectable agent comprises a contrast agent. In some embodiments, the contrast agent comprises $Gd^{3+}$.

In some embodiments, each detectable agent further comprises a chelating group independently selected from the group consisting of CB-TE2A, CB-TE1A1P, DiAmSar, DTPA, DOTA, DOTAGA, DOTMA, EDTA, EHPG, HBED, LICAM, MECAM, NOTA, NODAGA, PCTA, PDTA, TETA, TETMA, TTHA, CDTA, HBET, CP256.

In some embodiments, each of $D^1$ and $D^2$ are independently selected from the group consisting of:

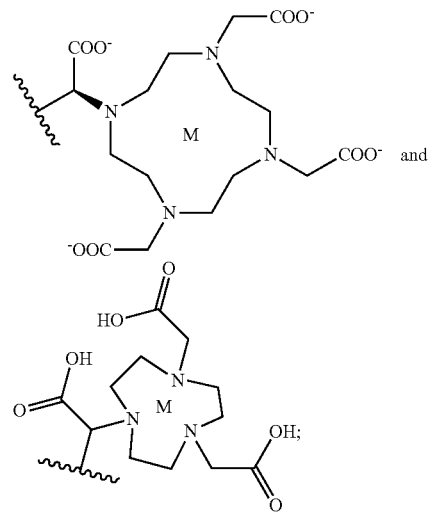

wherein each M is independently selected from Gd, $^{64}$Cu, and $^{68}$Ga. In some embodiments, $D^1$ is

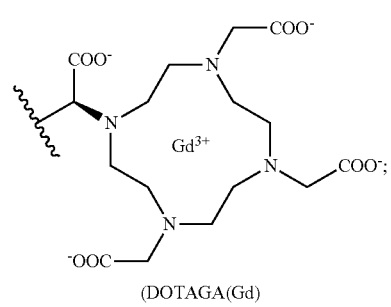

(DOTAGA(Gd))

$D^2$ is

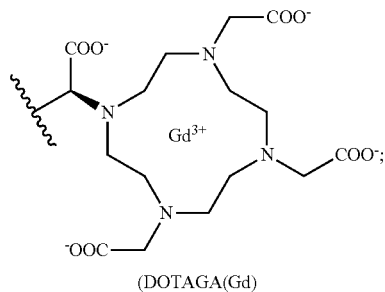

(DOTAGA(Gd))

a is 2; and
d is 2.

In some embodiments, $D^1$ is $^{68}$Ga-NODAGA; $D^2$ is $^{68}$Ga-NODAGA; a is 1; and d is 1.

In some embodiments, $D^1$ is $^{64}$Cu-NODAGA; $D^2$ is $^{64}$Cu-NODAGA; a is 1; and d is 1.

In some embodiments, each detectable agent comprises a fluorescent material. In some embodiments, each fluorescent material is independently selected from the group consisting of boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl)amino)hexanoic acid, Oregon Green 88, 6-(((4,4-difluoro-5-(2-pyrrolyl)-4-bora-3a,4a-diaza-s-indacene-3-yl)styryloxy)acetypaminohexanoic acid, 7-N,N-diethylaminocoumarin, sulforhodamine 101, VIVOTAG 680, umbelliferone, fluorescein, rhodamine, tetramethylrhodamine, dichlorotriazinylamine fluorescein, dansyl, and phycoerythrin. In some embodiments, each fluorescent material is tetramethylrhodamine.

In some embodiments, $L^1$ is selected from the group consisting of $C_{1-6}$ alkylene, $C_{2-6}$ alkenylene, $C_{2-6}$ alkynylene, $C_{1-6}$ haloalkylene, $C(=O)R^{a2}$, $C(=O)OR^{b2}$, $C(=O)NR^{c2}R^{d2}$, $NR^{c2}C(=O)R^{a2}$, $NR^{c2}C(=O)OR^{b2}$, $NR^{c2}C(=O)NR^{c2}R^{d2}$, $S(O)R^{e2}$, $S(O)_2R^{e2}$, $NR^{c2}S(O)R^{e2}$, $NR^{c2}S(O)_2R^{e2}$, $NR^{c2}S(=O)NR^{c2}R^{d2}$, and $NR^{c2}S(=O)_2NR^{c2}R^{d2}$; wherein:

each $R^{a2}$, $R^{b2}$, $R^{c2}$, $R^{d2}$, and $R^{e2}$ is independently selected from H, $C_{1-6}$ alkylene, $C_{1-6}$ haloalkylene, $C_{2-6}$ alkenylene, and $C_{2-6}$ alkynylene.

In some embodiments, $L^2$ is selected from the group consisting of $C_{1-6}$ alkylene, $C_{2-6}$ alkenylene, $C_{2-6}$ alkynylene, $C_{1-6}$ haloalkylene, $C(=O)R^{a2}$, $C(=O)OR^{b2}$, $C(=O)NR^{c2}R^{d2}$, $NR^{c2}C(=O)R^{a2}$, $NR^{c2}C(=O)OR^{b2}$, $NR^{c2}C(=O)NR^{c2}R^{d2}$, $S(O)R^{e2}$, $S(O)_2R^{e2}$, $NR^{c2}S(O)R^{e2}$, $NR^{c2}S(O)_2R^{e2}$, $NR^{c2}S(=O)NR^{c2}R^{d2}$, and $NR^{c2}S(=O)_2NR^{c2}R^{d2}$; wherein:

each $R^{a2}$, $R^{b2}$, $R^{c2}$, $R^{d2}$, and $R^{e2}$ is independently selected from H, $C_{1-6}$ alkylene, $C_{1-6}$ haloalkylene, $C_{2-6}$ alkenylene, and $C_{2-6}$ alkynylene.

In some embodiments, $L^1$ and $L^2$ are each $C(O)R^{a2}$, wherein each $R^{a2}$ is independently selected from the group consisting of $C_{1-6}$ alkylene, $C_{1-6}$ haloalkylene, $C_{2-6}$ alkenylene, and $C_{2-6}$ alkynylene. In some embodiments, $L^1$ and $L^2$ are each $C(O)R^{a2}$, wherein each $R^{a2}$ is $C_{1-6}$ alkylene. In some embodiments, each $L^1$ and $L^2$ is —C(O)CH$_2$CH$_2$—.

In some embodiments, the linear polypeptide comprising at least two disulfide moieties has a fibrin binding affinity of at least 25% of the fibrin binding affinity of the cyclized polypeptide. In some embodiments, the linear polypeptide comprising at least two disulfide moieties has a fibrin binding affinity of at least 10% of the fibrin binding affinity of the cyclized polypeptide. In some embodiments, the linear polypeptide comprising at least two disulfide moieties has a fibrin binding affinity of less than 1% of the fibrin binding affinity of the cyclized polypeptide.

The present application further provides a compound of Formula (I):

or a pharmaceutically acceptable salt thereof
wherein:
X is a linear polypeptide comprising at least two disulfide moieties and capable of binding to fibrin upon cyclization of the at least two disulfide moieties;
each $D^1$ is independently a detectable agent;
each $D^2$ is independently a detectable agent;
$L^1$ is a linker;
$L^2$ is a linker;
a is an integer from 0 to 4;
b is 0 or 1;
wherein if a is 0, b is 0;
c is 0 or 1;
d is an integer from 0 to 4;
wherein if d is 0, c is 0; and
wherein at least one of a and d is an integer from 1 to 4.

In some embodiments, each disulfide moiety of X is a group of Formula (A):

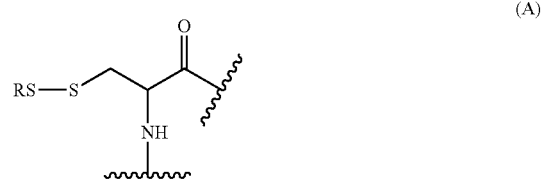

wherein each R is independently selected from the group consisting of $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-7 membered heterocycloalkyl, 4-10 membered heteroaryl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{a1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)R^{b1}$, $NR^{c1}S(=O)_2NR^{c1}R^{d1}$; wherein the $C_{1-6}$ alkyl, $C_{6-10}$ aryl, 4-7 membered heterocycloalkyl, and 4-7 membered heteroaryl groups are each optionally substituted with 1, 2, or 3 independently selected $R^A$ groups;

each $R^A$ is independently selected from the group consisting of OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$alkyl)aminosulfonylamino, aminocarbonylamino, $C_{1-3}$ alkylaminocarbonylamino, and di($C_{1-3}$ alkyl)aminocarbonylamino;

each $R^{a1}$, $R^{b1}$, $R^{c1}$, and $R^{d1}$ is independently selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-7 membered heterocycloalkyl, and 4-10 membered heteroaryl.

In some embodiments, each R is independently selected from the group consisting of a non-natural cysteine residue, a non-natural derivative of cysteine (e.g., penicillamine), $C_{6-10}$ aryl (e.g., phenyl), and 4-10 membered heteroaryl. In some embodiments, each R is independently selected from the group consisting of a non -natural cysteine residue, penicillamine, phenyl, 2-pyridine, 3-pyridine, and 4-pyridine.

In some embodiments, each disulfide moiety of X is selected from the group consisting of:

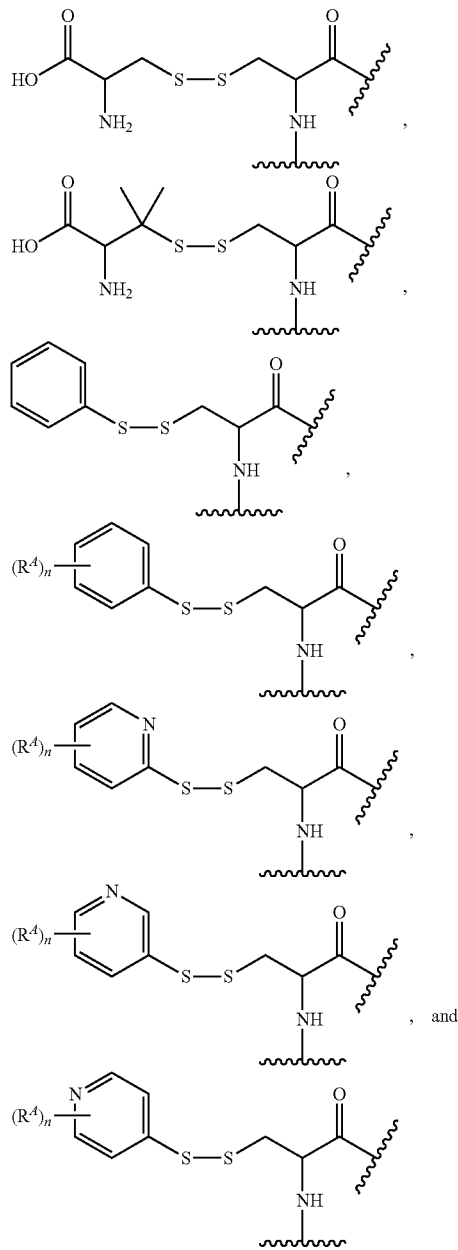
,

,

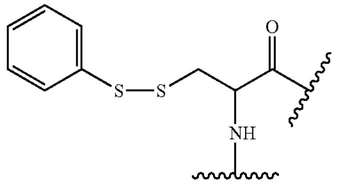

,

,

,

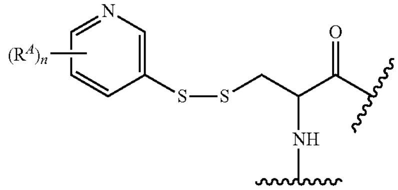

, and each $R^A$ is independently selected from the group consisting of OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$alkyl)aminosulfonylamino, aminocarbonylamino, $C_{1-3}$ alkylaminocarbonylamino, and di($C_{1-3}$ alkyl)aminocarbonylamino;

each $R^{a1}$, $R^{b1}$, $R^{c1}$, and $R^{d1}$ is independently selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-7 membered heterocycloalkyl, and 4-10 membered heteroaryl.

n is an integer from 1 to 3.

In some embodiments, X is a linear polypeptide comprising a sequence having at least 80% sequence identity to a sequence selected from the group consisting of:

(SEQ ID NO: 1)
W-Q-P-C*-P-W-E-S-W-T-F-C*-W-D-P (SEQ ID NO: 2)
W-Q-P-C*-P-A-E-S-W-T-F-C*-W-D-P (SEQ ID NO: 3)
G-P-P-G-W-Q-P-C*-P-W-E-S-W-T-F-C*-W-D-P (SEQ ID NO: 4)
G-G-R-G-W-Q-P-C*-P-W-E-S-W-T-F-C*-W-D-P (SEQ ID NO: 5)
G-W-Q-P-C*-P-W-E-S-W-T-F-C*-W-D-P (SEQ ID NO: 6)
S-G-S-G-T-W-Q-P-C*-P-W-E-S-W-T-F-C*-W-D-P (SEQ ID NO: 7)
W-Q-P-C*-P-W-E-S-W-T-Cha-C*-W-D-P (SEQ ID NO: 8)
W-Q-P-C*-P-W-E-S-W-T-Ffe4-C*-W-D-P (SEQ ID NO: 9)
W-Q-P-C*-P-W-E-S-W-T-F34fe-C*-W-D-P (SEQ ID NO: 10)
R-G-W-Q-P-C*-P-W-E-S-W-T-F-C*-W-D-P (SEQ ID NO: 11)
R-W-Q-P-C*-P-W-E-S-W-T-F-C*-W-D-P (SEQ ID NO: 12)
S-G-S-G-S-G-S-G-W-Q-P-C*-P-W-E-S-W-T-F-C*-W-D-P (SEQ ID NO: 13)
K-K-G-W-Q-P-C*-P-W-E-S-W-T-F-C*-W-D-P (SEQ ID NO: 14)
K-G-K-G-K-G-W-Q-P-C*-P-W-E-S-W-T-F-C*-W-D-P (SEQ ID NO: 15)
S(Galnac)-W-Q-P-C*-P-W-E-S-W-T-F-C*-W-D-P (SEQ ID NO: 16)
Thf2ca-W-Q-P-C*-P-W-E-S-W-T-F-C*-W-D-P (SEQ ID NO: 17)
R-R-G-G-W-Q-P-C*-P-W-E-S-W-T-F-C*-W-D-P (SEQ ID NO: 18)
S(Galnac)-T-W-Q-P-C*-P-W-E-S-W-T-F-C*-W-D-P (SEQ ID NO: 19)
W-Q-P-C*-Hvot4-W-E-S-W-T-F-C*-W-D-P (SEQ ID NO: 20)
G-P-P-G-W-Q-P-C*-P-A-E-S-W-T-F-C*-W-D-P -continued

```
                                                (SEQ ID NO: 21)
G-G-R-G-W-Q-P-C*-P-A-E-S-W-T-F-C*-W-D-P (SEQ ID NO: 22)
K-K-G-W-Q-P-C*-P-A-E-S-W-T-F-C*-W-D-P (SEQ ID NO: 23)
K-G-K-G-K-G-W-Q-P-C*-P-A-E-S-W-T-F-C*-W-D-P (SEQ ID NO: 24)
G-W-Q-P-C*-P-A-E-S-W-T-F-C*-W-D-P (SEQ ID NO: 25)
S-G-S-G-S-G-S-G-W-Q-P-C*-P-A-E-S-W-T-F-C*-W-D-P (SEQ ID NO: 26)
W-Q-P-C*-P-A-E-S-W-T-Ffe4-C*-W-D-P (SEQ ID NO: 27)
W-Q-P-C*-P-A-E-S-W-T-Cha-C*-W-D-P (SEQ ID NO: 28)
W-Q-P-C*-P-A-E-S-W-T-F34fe-C*-W-D-P (SEQ ID NO: 29)
Thf2ca-W-Q-P-C*-P-A-E-S-W-T-F-C*-W-D-P (SEQ ID NO: 30)
S-G-S-G-T-W-Q-P-C*-P-A-E-S-W-T-F-C*-W-D-P (SEQ ID NO: 31)
R-R-G-G-W-Q-P-C*-P-A-E-S-W-T-F-C*-W-D-P (SEQ ID NO: 32)
R-R-G-G-W-Q-P-C*-Hvot4-W-E-S-W-T-F-C*-W-D-P (SEQ ID NO: 33)
J-S-W-Q-P-C*-P-A-E-S-W-T-Cha-C*-W-D-P (SEQ ID NO: 34)
G-W-Q-P-C*-P-A-E-S-W-T-Cha-C*-W-D-P (SEQ ID NO: 35)
R-G-W-Q-P-C*-P-A-E-S-W-T-F-C*-W-D-P (SEQ ID NO: 36)
R-G-W-Q-P-C*-P-A-E-S-W-T-Cha-C*-W-D-P (SEQ ID NO: 37)
R-S-W-Q-P-C*-P-A-E-S-W-T-F-C*-W-D-P;
``` wherein C* is a group of Formula (A).

In some embodiments, X is a linear polypeptide comprising a sequence having at least 80% sequence identity to a sequence:

```
                                                (SEQ ID NO: 38)
X1-X2-C*-P*-Y*-X3-L-C*-X4-X5-X6
``` wherein:
C* is a group of Formula (A);
P* is proline or a non-natural derivative thereof;
Y* is tyrosine or a non-natural derivative thereof;
$X_1$ is W, Y, F, S, Bip, Hx, Dpr, Cy, Gu, Ad, Hfe, 3-Pal, 4-Pal, DopaMe2, nY, dW, dF, F(3/4*), or Y(3*), wherein F(3/4*) is a phenylalanine substituted at either the 3 or the 4 position with a moiety such as $CH_3$, $CF_3$, $NH_2$, $CH_2NH_2$, CN, F, Cl, Br, I, Et, or Orne, and Y(3*) is a tyrosine substituted at the 3 position with a moiety such as F, Cl, Br, I, and $NO_2$;
$X_2$ is E, H, dE, S, H(Bzl), 2-Pal, Dpr, or Th;
$X_3$ is G or D;
$X_4$ is H, F, Y, or W;
$X_5$ is I, L, V, N, Bpa, Bal, Hfe, Nle, Tle, NV, Phg, Cha, Taz, Fua, Th, 4-Pal, or F(3/4*), wherein F(3/4*) is a phenylalanine substituted at either the 3 or the 4 position with a moiety such as $CF_3$, Et, iPr, or OMe; and $X_6$ is N, Q, I, L, or V, or not present. In some embodiments, at least one of $X_1$, $X_2$, $X_5$, P*, and Y* is a non-natural derivative of an amino acid. In some embodiments, P* is proline and Y* is a non-natural derivative of tyrosine, substituted at the 3 position by F, Cl, Br, I, or $NO_2$. In some embodiments, P* is 4-hydroxyproline and Y* is tyrosine.

In some embodiments, X is a linear polypeptide comprising a sequence having at least 80% sequence identity to a sequence selected from the group consisting of:

```
                                                (SEQ ID NO: 39)
W-dE-C*-P(4-OH)-Y(3-Cl)-G-L-C*-W-I-Q (SEQ ID NO: 40)
Y-dE-C*-P(4-OH)-Y(3-Cl)-G-L-C*-Y-I-Q (SEQ ID NO: 41)
Y-dE-C*-P(4-OH)-Y(3-Cl)-G-L-C*-W-I-Q (SEQ ID NO: 42)
W-dE-C*-P(4-OH)-Y(3-Cl)-G-L-C*-Y-I-Q (SEQ ID NO: 43)
W-dE-C*-P(4-OH)-Y(3-Cl)-D-L-C*-W-I-Q (SEQ ID NO: 44)
Y-dE-C*-P(4-OH)-Y(3-Cl)-D-L-C*-Y-I-Q (SEQ ID NO: 45)
Y-dE-C*-P(4-OH)-Y(3-Cl)-D-L-C*-W-I-Q (SEQ ID NO: 46)
W-dE-C*-P(4-OH)-Y(3-Cl)-D-L-C*-Y-I-Q (SEQ ID NO: 47)
F(4-OMe)-H-C*-P(4-OH)-Y(3-Cl)-D-L-C*-H-I-L (SEQ ID NO: 48)
Y-H-C*-P(4-OH)-Y(3-Cl)-G-L-C*-W-I-Q (SEQ ID NO: 49)
W-dE-C*-P-Y(3-Cl)-G-L-C*-W-I-Q (SEQ ID NO: 50)
W-dE-C*-P(4-OH)-Y-G-L-C*-W-I-Q (SEQ ID NO: 51)
F-H-C*-P(4-OH)-Y(3-Cl)-D-L-C*-H-I-L (SEQ ID NO: 52)
F(4-OMe)-H-C*-P(4-OH)-Y(3-Cl)-D-L-C*-H-I (SEQ ID NO: 53)
F(4-OMe)-H-C*-P(4-OH)-Y(3-I)-D-L-C*-H-Bpa (SEQ ID NO: 54)
F-H-C*-P(4-OH)-Y(3-I)-D-L-C*-H-Hfe (SEQ ID NO: 55)
F-H-C*-P(4-OH)-Y(3-I)-D-L-C*-H-Bpa (SEQ ID NO: 56)
Y(3-Cl)-H-C*-P(4-OH)-Y(3-I)-D-L-C*-H-I (SEQ ID NO: 57)
F(4-OMe)-H-C*-P(4-OH)-Y(3-I)-D-L-C*-H-I-L (SEQ ID NO: 58)
F(4-OMe)-H(Bzl)-C*-P(4-OH)-Y(3-Cl)-D-L-C*-H-Bpa (SEQ ID NO: 59)
F-H-C*-P(4-OH)-Y(3-Cl)-D-L-C*-H-I (SEQ ID NO: 60)
F(4-OMe)-H-C*-P(4-OH)-Y(3-I)-D-L-C*-H-I (SEQ ID NO: 61)
3Pal-H-C*-P(4-OH)-Y(3-I)-D-L-C*-H-I
```

(SEQ ID NO: 62)
4Pal-H-C*-P(4-OH)-Y(3-I)-D-L-C*-H-I (SEQ ID NO: 63)
F(4-F)-H-C*-P(4-OH)-Y(3-I)-D-L-C*-H-I (SEQ ID NO: 64)
Y(3-I)-H-C*-P(4-OH)-Y(3-I)-D-L-C*-H-I (SEQ ID NO: 65)
F-H-C*-P(4-OH)-Y(3-I)-D-L-C*-H-I-L (SEQ ID NO: 66)
F(4-OMe)-H-C*-P(4-OH)-Y(3-Cl)-D-L-C*-H-Bpa-L (SEQ ID NO: 67)
F(4-OMe)-H-C*-P(4-OH)-Y(3-I)-D-L-C*-H-Bpa-L (SEQ ID NO: 68)
F-H(Bzl)-C*-P(4-OH)-Y(3-Cl)-D-L-C*-H-I-L (SEQ ID NO: 69)
1Nal-H-C*-P(4-OH)-Y(3-I)-D-L-C*-H-I (SEQ ID NO: 70)
MY-H-C*-P(4-OH)-Y(3-I)-D-L-C*-H-I (SEQ ID NO: 71)
F(4-OMe)-H(Bzl)-C*-P(4-OH)-Y(3-I)-D-L-C*-H-Bpa (SEQ ID NO: 72)
F(4-OMe)-H(Bzl)-C*-P(4-OH)-Y(3-Cl)-D-L-C*-H-I (SEQ ID NO: 73)
F-H-C*-P(4-OH)-Y(3-I)-D-L-C*-3Pal-I (SEQ ID NO: 74)
F(4-I)-H-C*-P(4-OH)-Y(3-I)-D-L-C*-H-I (SEQ ID NO: 75)
F(4-Br)-H-C*-P(4-OH)-Y(3-I)-D-L-C*-H-I (SEQ ID NO: 76)
F(4-Me)-H-C*-P(4-OH)-Y(3-I)-D-L-C*-H-I (SEQ ID NO: 77)
F(4-CF3)-H-C*-P(4-OH)-Y(3-I)-D-L-C*-H-I (SEQ ID NO: 78)
F(4-CN)-H-C*-P(4-OH)-Y(3-I)-D-L-C*-H-I (SEQ ID NO: 79)
Y(3-NO2)-H-C*-P(4-OH)-Y(3-I)-D-L-C*-H-I (SEQ ID NO: 80)
Y(2-F)-H-C*-P(4-OH)-Y(3-I)-D-L-C*-H-I (SEQ ID NO: 81)
F(4-CH2NH2)-H-C*-P(4-OH)-Y(3-I)-D-L-C*-H-I (SEQ ID NO: 82)
F(4-NH2)-H-C*-P(4-OH)-Y(3-I)-D-L-C*-H-I (SEQ ID NO: 83)
F(34-F2)-H-C*-P(4-OH)-Y(3-I)-D-L-C*-H-I (SEQ ID NO: 84)
DopaMe2-H-C*-P(4-OH)-Y(3-I)-D-L-C*-H-I (SEQ ID NO: 85)
F(2-OMe)-H-C*-P(4-OH)-Y(3-I)-D-L-C*-H-I (SEQ ID NO: 86)
F(3-Me)-H-C*-P(4-OH)-Y(3-I)-D-L-C*-H-I (SEQ ID NO: 87)
F-H-C*-P(4-OH)-Y(3-I)-D-L-C*-H-I (SEQ ID NO: 88)
F-H-C*-P(4-OH)-Y(3-I)-D-L-C*-H-F(3-CF3)

(SEQ ID NO: 89)
F(3-CF3)-H-C*-P(4-OH)-Y(3-I)-D-L-C*-H-I (SEQ ID NO: 90)
F(3-OMe)-H-C*-P(4-OH)-Y(3-I)-D-L-C*-H-I (SEQ ID NO: 91)
Hfe-H-C*-P(4-OH)-Y(3-I)-D-L-C*-H-I (SEQ ID NO: 92)
nY-H-C*-P(4-OH)-Y(3-I)-D-L-C*-H-I (SEQ ID NO: 93)
W-E-C*-P(4-OH)-Y(3-Cl)-G-L-C*-W-I-Q (SEQ ID NO: 94)
F-H-C*-P(4-OH)-Y(3-I)-D-L-C*-H-I-L (SEQ ID NO: 95)
F(4-OMe)-H(Bzl)-C*-P(4-OH)-Y(3-I)-D-L-C*-H-I (SEQ ID NO: 96)
F-H-C*-P(4-OH)-Y(3-I)-D-L-C*-H-Nle (SEQ ID NO: 97)
F-H-C*-P(4-OH)-Y(3-I)-D-L-C*-H-Tle (SEQ ID NO: 98)
F-H-C*-P(4-OH)-Y(3-I)-D-L-C*-H-F(4-CF3)

(SEQ ID NO: 99)
F-H-C*-P(4-OH)-Y(3-I)-D-L-C*-H-Bip (SEQ ID NO: 100)
F-H-C*-P(4-OH)-Y(3-I)-D-L-C*-H-F(4-Et)

(SEQ ID NO: 101)
F-H-C*-P(4-OH)-Y(3-I)-D-L-C*-H-F(4-OMe)

(SEQ ID NO: 102)
F-H-C*-P(4-OH)-Y(3-I)-D-L-C*-H-F(3-OMe)

(SEQ ID NO: 103)
F(F5)-H-C*-P(4-OH)-Y(3-I)-D-L-C*-H-I (SEQ ID NO: 104)
F-H-C*-P(4-OH)-Y(3-F)-D-L-C*-H-I-L (SEQ ID NO: 105)
W-E-C*-P(4-OH)-Y(3-Cl)-G-L-C*-W-I-Q (SEQ ID NO: 106)
T-dE-C*-P(4-OH)-Y(3-Cl)-G-L-C*-W-I-Q (SEQ ID NO: 107)
F-H-C*-P-Y(3-Cl)-D-L-C*-H-I-L (SEQ ID NO: 108)
Y(26-Me)-H-C*-P(4-OH)-Y(3-I)-D-L-C*-H-I (SEQ ID NO: 109)
W-E-C*-P(4-OH)-Y(3-Cl)-G-L-C*-H-I-Q (SEQ ID NO: 110)
dF-dE-C*-P(4-OH)-Y(3-Cl)-G-L-C*-W-I-Q (SEQ ID NO: 111)
Y-E-C*-P(4-OH)-Y(3-Cl)-G-L-C*-Y-I-Q (SEQ ID NO: 112)
W-E-C*-P(4-OH)-Y(3-Cl)-G-L-C*-F-I-Q (SEQ ID NO: 113)
H-dE-C*-P(4-OH)-Y(3-Cl)-G-L-C*-W-I-Q (SEQ ID NO: 114)
F-H-C*-P(4-OH)-Y(3-I)-D-L-C*-H-I-L (SEQ ID NO: 115)
W-E-C*-P-Y-G-L-C*-W-I-Q

```
F-H-C*-P(4-OH)-Y(3-I)-D-L-C*-H-nV          (SEQ ID NO: 116)

F-H-C*-P(4-OH)-Y(3-I)-D-L-C*-H-Phg         (SEQ ID NO: 117)

F-H-C*-P(4-OH)-Y(3-I)-D-L-C*-H-F(3-Me)     (SEQ ID NO: 118)

F-H-C*-P(4-OH)-Y(3-I)-D-L-C*-4Pal-I        (SEQ ID NO: 119)

S-dE-C*-P(4-OH)-Y(3-Cl)-G-L-C*-W-I-Q       (SEQ ID NO: 120)

W-E-C*-P(4-OH)-Y(3-Cl)-G-L-C*-Y-I-Q        (SEQ ID NO: 121)

Y-E-C*-P(4-OH)-Y(3-Cl)-G-L-C*-W-I-Q        (SEQ ID NO: 122)

F-dE-C*-P(4-OH)-Y(3-Cl)-G-L-C*-W-I-Q       (SEQ ID NO: 123)

F-H-C*-P-Y-D-L-C*-H-I-L                    (SEQ ID NO: 124)

F-H-C*-P(4-OH)-Y(3-I)-D-L-C*-H-I-L         (SEQ ID NO: 125)

F-H-C*-P(4-OH)-Y-D-L-C*-H-Bpa              (SEQ ID NO: 126)

F-H-C*-P(4-OH)-Y(3-Cl)-G-L-C*-H-I-L        (SEQ ID NO: 127)

S(Bzl)-H-C*-P-Y-D-L-C*-H-I-L               (SEQ ID NO: 128)

H-E-C*-P(4-OH)-Y(3-Cl)-G-L-C*-H-I-Q        (SEQ ID NO: 129)

F(4-OMe)-H-C*-P(4-OH)-Y-D-L-C*-H-I-L       (SEQ ID NO: 130)

F-H-C*-P(4-OH)-Y(3-I)-D-L-C*-Bpa-I         (SEQ ID NO: 131)

Ad-H-C*-P(4-OH)-Y(3-I)-D-L-C*-H-I          (SEQ ID NO: 132)

F-H-C*-P(4-OH)-Y(3-Cl)-F-L-C*-H-I-L        (SEQ ID NO: 133)

F-E-C*-P(4-OH)-Y(3-Cl)-G-L-C*-W-I-Q        (SEQ ID NO: 134)

F-H-C*-P(4-OH)-Y(3-Cl)-2-Nal-L-C*-H-I-L    (SEQ ID NO: 135)

F-H-C*-P(4-OH)-Y-D-L-C*-H-I-L              (SEQ ID NO: 136)

Hfe-H-C*-P(4-OH)-Y-D-L-C*-H-I-L            (SEQ ID NO: 137)

Bip-H-C*-P(4-OH)-Y-D-L-C*-H-I-L            (SEQ ID NO: 138)

W-E-C*-P-Y-G-L-C*-W-I-Q                    (SEQ ID NO: 139)

F(4-OMe)-W-C*-P(4-OH)-Y(3-I)-D-L-C*-H-I    (SEQ ID NO: 140)

F-H-C*-P(4-OH)-Y(3-I)-D-L-C*-2Pal-I        (SEQ ID NO: 141)

F-H-C*-P(4-OH)-Y(3-I)-D-L-C*-Taz-I         (SEQ ID NO: 142)

F-H-C*-P(4-OH)-Y(3-I)-D-L-C*-Dht-I,        (SEQ ID NO: 143)
and

Gu-H-C*-P(4-OH)-Y(3-I)-D-L-C*-H-I.         (SEQ ID NO: 144)
```

In some embodiments, X is a linear polypeptide comprising a sequence having at least 80% sequence identity to a sequence:

$$C^*-P^*-Y^*-X_1-L-C^* \quad \text{(SEQ ID NO: 145)}$$

wherein $X_1$ is G or D;

C* is a group of Formula (A);

P* is proline or its non-natural derivative 4-hydroxyproline; and

Y* is tyrosine or a non-natural derivative of tyrosine substituted at the 3 position with a moiety selected from the group consisting of fluoro, chloro, bromo, iodo, and $NO_2$;

provided that at least one of P* or Y* is a non-natural derivative of the respective amino acid.

In some embodiments, X is a linear polypeptide comprising a sequence having at least 80% sequence identity to a sequence:

$$C^*-D-Y-Y-G-T-C^*-X_{10} \quad \text{(SEQ ID NO: 146)}$$

wherein:

C* is a group of Formula (A);

$X_{10}$ is selected from the group consisting of n(decyl)G, n(4-PhBu)G, MeL, Bpa, Bip, Me-Bip, F(4*), F(3-Me), F(3,4-difluoro), Amh, Hfe, Y(3,5-di-iodo), Pff, lNal, dlNal, and MeL, wherein F(4*) is a phenylalanine substituted at the 4 position with a moiety selected from the group consisting of Et, $CF_3$, I, and iPr.

In some embodiments, X is a linear polypeptide comprising a sequence having at least 80% sequence identity to a sequence:

$$X_1-P^*-C^*-D-Y-Y-G-T-C^*-X_{10}-X_{11} \quad \text{(SEQ ID NO: 147)}$$

wherein $X_1$ is any natural or non-natural amino acid,

C* is a group of Formula (A);

P* is proline or a non-natural derivative thereof, and wherein $X_{11}$ is selected from the group consisting of D, dD, βD, Inp, Nip, Me-D, dC, Cop, and Cmp.

In some embodiments, X is a linear polypeptide comprising a sequence having at least 80% sequence identity to a sequence selected from the group consisting of:

```
L-P-C*-D-Y-Y-G-T-C*-n(Decyl)G-dD      (SEQ ID NO: 148)

L-P-C*-D-Y-Y-G-T-C*-n(Decyl)G-D       (SEQ ID NO: 149)

L-P-C*-D-Y-Y-G-T-C*-Bip-D             (SEQ ID NO: 150)

L-P-C*-D-Y-Y-G-T-C*-Bip-dD            (SEQ ID NO: 151)
```

-continued

```
                                                 (SEQ ID NO: 152)
L-P-C*-D-Y-Y-G-T-C*-MeL-Inp (SEQ ID NO: 153)
L-P-C*-D-Y-Y-G-T-C*-MeL-Cmp (SEQ ID NO: 154)
L-P-C*-D-Y-Y-G-T-C*-MeBip-D (SEQ ID NO: 155)
L-P*-C*-D-Y-Y-G-T-C*-n(Decyl)G-dD (SEQ ID NO: 156)
L-P*-C*-D-Y-Y-G-T-C*-n(Decyl)G-D (SEQ ID NO: 157)
L-P*-C*-D-Y-Y-G-T-C*-MeL-Inp (SEQ ID NO: 158)
L-P*-C*-D-Y-Y-G-T-C*-Bip-D (SEQ ID NO: 159)
L-P*-C*-D-Y-Y-G-T-C*-Bip-dD (SEQ ID NO: 160)
L-P*-C*-D-Y-Y-G-T-C*-Me-Bip-D (SEQ ID NO: 161)
L-P*-C*-D-Y-Y-G-T-C*-MeL-Cmp (SEQ ID NO: 162)
L-P*-C*-D-Y-Y-G-T-C*-L-D (SEQ ID NO: 163)
Cha-P*-C*-D-Y-Y-G-T-C*-Bip-D.
```

In some embodiments, X is a linear polypeptide comprising a sequence having at least 80% sequence identity to a sequence selected from the group consisting of:

```
                                                 (SEQ ID NO: 164)
Y-dE-C*-P(4-OH)-3C-L-Y-G-L-C*-Y-I-Q (SEQ ID NO: 165)
R-W-Q-P-C*-P-A-E-S-W-T-Cha-C*-W-D-P (SEQ ID NO: 166)
R-W-Q-P-C*-P-A-E-S-W-T-Cha-C*-W-D-P-G-G-G-K.
```

In some embodiments, X is a linear polypeptide comprising a sequence having at least 80% sequence identity to a sequence:

```
                                                 (SEQ ID NO: 167)
C*-X_2-X_3-Y-X_5-X_6-C*
``` wherein:
C* is a group of Formula (A);
$X_2$ is A, E, F, G, Ile, K, L, M, R, T, V, Y, N, D, Gln, H, S, or Tφ;
$X_3$ is S, F, A, or Y;
$X_5$ is G, A, or dA; and
$X_6$ is T, V, or S. In some embodiments, (SEQ ID NO: 167) is: C*—$X_2$—$X_3$—Y—G—T —C* (SEQ ID NO: 168).

In some embodiments, X is a linear polypeptide comprising a sequence having at least 80% sequence identity to a sequence:

```
                                                 (SEQ ID NO: 169)
X_1-X_2-C*-X_4-X_5-Y-X_7-X_8-C*-X_10-X_11
``` wherein:
C* is a group of Formula (A);
$X_1$ is R, D, H, L, or F;
$X_2$ is A, D, G, P, or S;
$X_4$ is A, E, F, G, Ile, K, L, M, R, T, V, Y, N, D, Gln, H, S, or Tφ;
$X_5$ is A, Y, F, or S;
$X_7$ is G, A, or dA;
$X_8$ is T, V, or S;
$X_{10}$ is H, L, or F; and
$X_{11}$ is R, D, or H.

In some embodiments, X is a linear polypeptide comprising a sequence having at least 80% sequence identity to a sequence:

```
                                                 (SEQ ID NO: 170)
C*-Y-X_3-S-Y-X_6-X_7-X_8-X_9-C*
``` wherein:
C* is a group of Formula (A);
$X_3$ is N or D;
$X_6$ is G or Y;
$X_7$ is H or V;
$X_8$ is P or Tφ; and
and $X_9$ is Tφ or Y.

In some embodiments, X is a linear polypeptide comprising a sequence having at least 80% sequence identity to a sequence:

```
                                                 (SEQ ID NO: 171)
X_1-X_2-X_3-C*-Y-X_6-S-Y-X_9-X_10-X_11-X_12-C*-X_14-X_15-X_16
``` wherein:
$X_1$ is N or R;
$X_2$ is H or F;
$X_3$ is G or L;
C* is a group of Formula (A);
$X_6$ is N or D;
$X_9$ is G or Y;
$X_{10}$ is V or H;
$X_{11}$ is P or Tφ;
$X_{12}$ is Y or Tφ;
$X_{14}$ is D or S;
$X_{15}$ is Y or H;
and $X_{16}$ is S or H.

In some embodiments, X is a linear polypeptide comprising a sequence having at least 80% sequence identity to a sequence:

```
                                                 (SEQ ID NO: 172)
X_1-X_2-C*-P-Y-X_6-L-C*-X_9-X_10-X_11
``` wherein $X_1$ is Tφ, F, H, or Y;
$X_2$ is H, D, or E;
C* is a group of Formula (A);
$X_6$ is D, G, or A;
$X_9$ is H, F, Y, or Tφ;
$X_{10}$ is Ile, L, or V; and
$X_{11}$ is N, Gln, He, L, or V.

In some embodiments, X is a linear polypeptide comprising a sequence having at least 80% sequence identity to a sequence selected from the group consisting of:

```
                                                 (SEQ ID NO: 173)
R-S-C*-N-Y-Y-G-T-C*-L-H
```

```
                                            (SEQ ID NO: 174)
H-D-C*-Q-Y-Y-G-T-C*-L-H (SEQ ID NO: 175)
F-A-C*-H-Y-Y-G-T-C*-L-H (SEQ ID NO: 176)
R-P-C*-D-Y-Y-G-T-C*-F-D (SEQ ID NO: 177)
L-P-C*-D-Y-Y-G-T-C*-L-D (SEQ ID NO: 178)
F-S-C*-Tφ-Y-S-L-H-C*-H-R (SEQ ID NO: 179)
D-P-C*-S-Y-Y-G-T-C*-L-H (SEQ ID NO: 180)
L-P-C*-S-Y-Y-G-T-C*-L-H (SEQ ID NO: 181)
L-S-C*-D-Y-Y-G-T-C*-L-R (SEQ ID NO: 182)
L-A-C*-H-Y-Y-G-T-C*-L-H (SEQ ID NO: 183)
D-G-C*-H-Y-Y-G-T-C*-L-H (SEQ ID NO: 184)
R-P-C*-N-Y-Y-G-T-C*-L-H (SEQ ID NO: 185)
N-H-G-C*-Y-N-S-Y-G-V-P-Y-C*-D-Y-S (SEQ ID NO: 186)
R-F-L-C*-Y-D-S-Y-Y-H-Tφ-Tφ-C*-S-H-H (SEQ ID NO: 187)
Tφ-F-H-C*-P-Y-D-L-C*-H-I-L (SEQ ID NO: 188)
Q-W-E-C*-P-Y-G-L-C*-Tφ-I-Q (SEQ ID NO: 189)
G-F-H-C*-P-Y-D-L-C*-H-I-L (SEQ ID NO: 190)
F-H-C*-P-Y-D-L-C*-H-I-L (SEQ ID NO: 191)
H-C*-P-Y-D-L-C*-H-I-L (SEQ ID NO: 192)
F-H-C*-P-Y-D-L-C*-H-I (SEQ ID NO: 193)
Tφ-E-C*-P-Y-G-L-C*-Tφ-I-Q (SEQ ID NO: 194)
E-C*-P-Y-G-L-C*-Tφ-I-Q (SEQ ID NO: 195)
Tφ-E-C*-P-Y-G-L-C*-Tφ-I (SEQ ID NO: 196)
P-C*-D-Y-Y-G-T-C*-L (SEQ ID NO: 197)
C*-D-Y-Y-G-T-C*-L (SEQ ID NO: 198)
C*-D-Y-Y-G-T-C*

(SEQ ID NO: 199)
L-P-C*-D-Y-Y-D-A-T-C*-L-D (SEQ ID NO: 200)
L-A-C*-D-Y-Y-G-T-C*-L-D (SEQ ID NO: 201)
L-P-C*-A-Y-Y-G-T-C*-L-D (SEQ ID NO: 202)
L-P-C*-D-A-Y-G-T-C*-L-D (SEQ ID NO: 203)
L-P-C*-D-Y-A-G-T-C*-L-D (SEQ ID NO: 204)
L-P-C*-D-Y-Y-A-T-C*-L-D (SEQ ID NO: 205)
L-P-C*-D-Y-Y-G-A-C*-L-D (SEQ ID NO: 206)
L-P-C*-D-Y-Y-G-T-C*-A-D (SEQ ID NO: 207)
L-P-C*-D-Y-Y-G-S-C*-L-D (SEQ ID NO: 208)
L-P-C*-D-Y-Y-G-V-C*-A-D (SEQ ID NO: 209)
G-F-H-C*-P-Y-D-L-C*-H-I-L (SEQ ID NO: 210)
F-H-C*-P-Y-D-L-C*-H-I-L (SEQ ID NO: 211)
H-C*-P-Y-D-L-C*-H-I-L (SEQ ID NO: 212)
F-H-C*-P-Y-D-L-C*-H-I (SEQ ID NO: 213)
W-E-C*-P-Y-G-L-C*-Tφ-I-Q (SEQ ID NO: 214)
E-C*-P-Y-G-L-C*-Tφ-I-Q and (SEQ ID NO: 215)
W-E-C*-P-Y-G-L-C*-Tφ-I;
``` wherein C* is a group of Formula (A).

In some embodiments, X is a linear polypeptide comprising a sequence having at least 80% sequence identity to a sequence selected from the group consisting of:

```
                                            (SEQ ID NO: 216)
F-H-C*-P(4-OH)-Y(3-Cl)-D-L-C*-H-I-Q (SEQ ID NO: 217)
Y-D-E-C*-P(4-OH)-Y(3-Cl)-G-L-C*-Y-I-Q (SEQ ID NO: 218)
Q-W-E-C*-P-Y-G-L-C*-W-I-Q,
``` wherein C* is a group of Formula (A).

In some embodiments, X is a linear polypeptide comprising a sequence at least 80% identical to a sequence selected from the group consisting of:

```
                                            (SEQ ID NO: 51)
F-H-C*-P(4-OH)-Y(3-Cl)-D-L-C*-H-I-L
and
                                            (SEQ ID NO: 218)
Q-W-E-C*-P-Y-G-L-C*-W-I-Q
``` wherein C* is a group of Formula (A).

In some embodiments, each detectable agent independently comprises one or more groups independently selected from the group consisting of a radioactive isotope, a fluorescent material, a contrast agent, a luminescent material, and bioluminescent material. In some embodiments, each detectable agent independently comprises one or more groups independently selected from the group consisting of a radioactive isotope, a luminescent material, a contrast agent, or a mixture thereof.

In some embodiments, each detectable agent comprises a radioactive isotope. In some embodiments, each radioactive isotope is independently selected from the group consisting of $^{99m}$Tc, $^{51}$Cr, Al—$^{18}$F, $^{67}$Ga, $^{68}$Ga, $^{44}$Sc, $^{47}$Sc, $^{167}$Tm, $^{141}$Ce, $^{111}$In, $^{113}$In, $^{168}$Yb, $^{175}$Yb, $^{140}$La, $^{90}$Y, $^{86}$Y, $^{153}$Sm, $^{166}$Ho, $^{165}$Dy, $^{166}$Dy, $^{61}$Cu, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au, $^{111}$Ag, $^{199}$Au, $^{51}$Mn, $^{52m}$Mn, $^{52g}$Mn $^{52}$Fe, $^{60}$Cu, $^{72}$As, $^{94m}$Tc, $^{110}$In, $^{142}$Pr, $^{153}$Gd and $^{159}$Gd. In some embodiments, each radioactive isotope is independently selected from the group consisting of Al—$^{18}$F, $^{64}$Cu, $^{99m}$Tc, $^{68}$Ga, and $^{111}$In. In some embodiments, each radioactive isotope is Al—$^{18}$F. In some embodiments, each radioactive isotope is $^{64}$Cu. In some embodiments, each radioactive isotope is $^{99m}$Tc. In some embodiments, each radioactive isotope is $^{68}$Ga. In some embodiments, each radioactive isotope is $^{111}$In.

In some embodiments, each detectable agent comprises a contrast agent. In some embodiments, the contrast agent comprises $Gd^{3+}$.

In some embodiments, each detectable agent further comprises a chelating group independently selected from the group consisting of CB-TE2A, CB-TE1A1P, DiAmSar, DTPA, DOTA, DOTAGA, DOTMA, EDTA, EHPG, HBED, LICAM, MECAM, NOTA, NODAGA, PCTA, PDTA, TETA, TETMA, TTHA, CDTA, HBET, CP256.

In some embodiments, each of $D^1$ and $D^2$ are independently selected from the group consisting of:

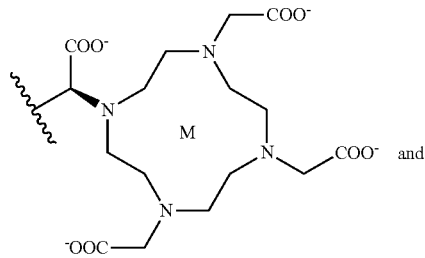

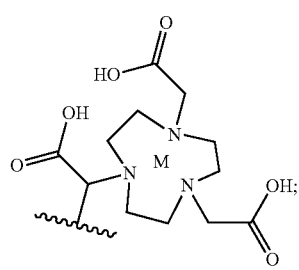

wherein each M is independently selected from Gd, $^{64}$Cu, and $^{68}$Ga. In some embodiments,

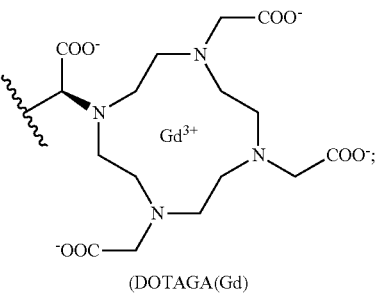

(DOTAGA(Gd))

$D^1$ is

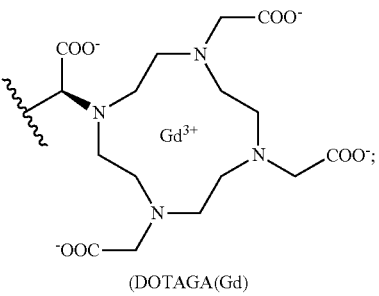

(DOTAGA(Gd))

$D^2$ is
a is 2; and
d is 2.

In some embodiments, $D^1$ is $^{68}$Ga-NODAGA; $D^2$ is $^{68}$Ga-NODAGA; a is 1; and d is 1.

In some embodiments, $D^1$ is $^{64}$Cu-NODAGA; $D^2$ is $^{64}$Ga-NODAGA; a is 1; and d is 1.

In some embodiments, each detectable agent comprises a fluorescent material. In some embodiments, each fluorescent material is independently selected from the group consisting of boron-dipyrromethene (BODIPY®), 4,4-difluoro-5,7-dimethyl-4-bora -3a,4a-diaza-s-indacene-3-propionic acid (BODIPY® FL), 6-((4,4-difluoro-1,3-dimethyl -5-(4-methoxyphenyl)-4-bora-3a,4a-diaza-s-indacene-2-propionyl)amino)hexanoic acid, Oregon Green 88, 6-(((4,4-difluoro-5-(2-pyrrolyl)-4-bora-3a,4a-diaza-s-indacene-3-yl) styryloxy)acetyl)aminohexanoic acid, 7-N,N-diethylaminocoumarin, sulforhodamine 101, VIVOTAG 680, umbelliferone, fluorescein, rhodamine, tetramethylrhodamine, dichlorotriazinylamine fluorescein, dansyl, and phycoerythrin. In some embodiments, each fluorescent material is tetramethylrhodamine.

In some embodiments, $L^1$ is selected from the group consisting of $C_{1-6}$ alkylene, $C_{2-6}$ alkenylene, $C_{2-6}$ alkynylene, $C_{1-6}$ haloalkylene, $C(=O)R^{a2}$, $C(=O)OR^{b2}$, $C(=O)NR^{c2}R^{d2}$, $NR^{c2}C(=O)R^{a2}$, $NR^{c2}C(=O)OR^{b2}$, $NR^{c2}C(=O)NR^{c2}R^{d2}$, $S(O)R^{e2}$, $S(O)_2R^{e2}$, $NR^{c2}S(O)R^{e2}$, $NR^{c2}S(O)_2R^{e2}$, $NR^{c2}S(=O)NR^{c2}R^{d2}$, and $NR^{c2}S(=O)_2NR^{c2}R^{d2}$; wherein:

each $R^{a2}$, $R^{b2}$, $R^{c2}$, $R^{d2}$, and $R^{e2}$ is independently selected from H, $C_{1-6}$ alkylene, $C_{1-6}$ haloalkylene, $C_{2-6}$ alkenylene, and $C_{2-6}$ alkynylene.

In some embodiments, $L^2$ is selected from the group consisting of $C_{1-6}$ alkylene, $C_{2-6}$ alkenylene, $C_{2-6}$ alkynylene, $C_{1-6}$ haloalkylene, $C(=O)R^{a2}$, $C(=O)OR^{b2}$, $C(=O)NR^{c2}R^{d2}$, $NR^{c2}C(=O)R^{a2}$, $NR^{c2}C(=O)OR^{b2}$, $NR^{c2}C(=O)NR^{c2}R^{d2}$, $S(O)R^{e2}$, $S(O)_2R^{e2}$, $NR^{c2}S(O)R^{e2}$, $NR^{c2}S(O)_2R^{e2}$, $NR^{c2}S(=O)NR^{c2}R^{d2}$, and $NR^{c2}S(=O)_2NR^{c2}R^{d2}$; wherein:

each $R^{a2}$, $R^{b2}$, $R^{c2}$, $R^{d2}$, and $R^{e2}$ is independently selected from H, $C_{1-6}$ alkylene, $C_{1-6}$ haloalkylene, $C_{2-6}$ alkenylene, and $C_{2-6}$ alkynylene.

In some embodiments, $L^1$ and $L^2$ are each $C(O)R^{a2}$, wherein each $R^{a2}$ is independently selected from the group consisting of $C_{1-6}$ alkylene, $C_{1-6}$ haloalkylene, $C_{2-6}$ alkenylene, and $C_{2-6}$ alkynylene. In some embodiments, $L^1$ and $L^2$ are each $C(O)R^{a2}$, wherein each $R^{a2}$ is $C_{1-6}$ alkylene. In some embodiments, each $L^1$ and $L^2$ is —$C(O)CH_2CH_2$—.

In some embodiments, the linear polypeptide comprising at least two disulfide moieties has a fibrin binding affinity of at least 25% of the fibrin binding affinity of the cyclized polypeptide. In some embodiments, the linear polypeptide comprising at least two disulfide moieties has a fibrin binding affinity of at least 10% of the fibrin binding affinity of the cyclized polypeptide. In some embodiments, the linear polypeptide comprising at least two disulfide moieties has a fibrin binding affinity of less than 1% of the fibrin binding affinity of the cyclized polypeptide.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 14A shows a radio-HPLC analysis of blood drawn 30 minutes after injection of FBP14 to a thrombotic rat.

DETAILED DESCRIPTION

Figure 1A:
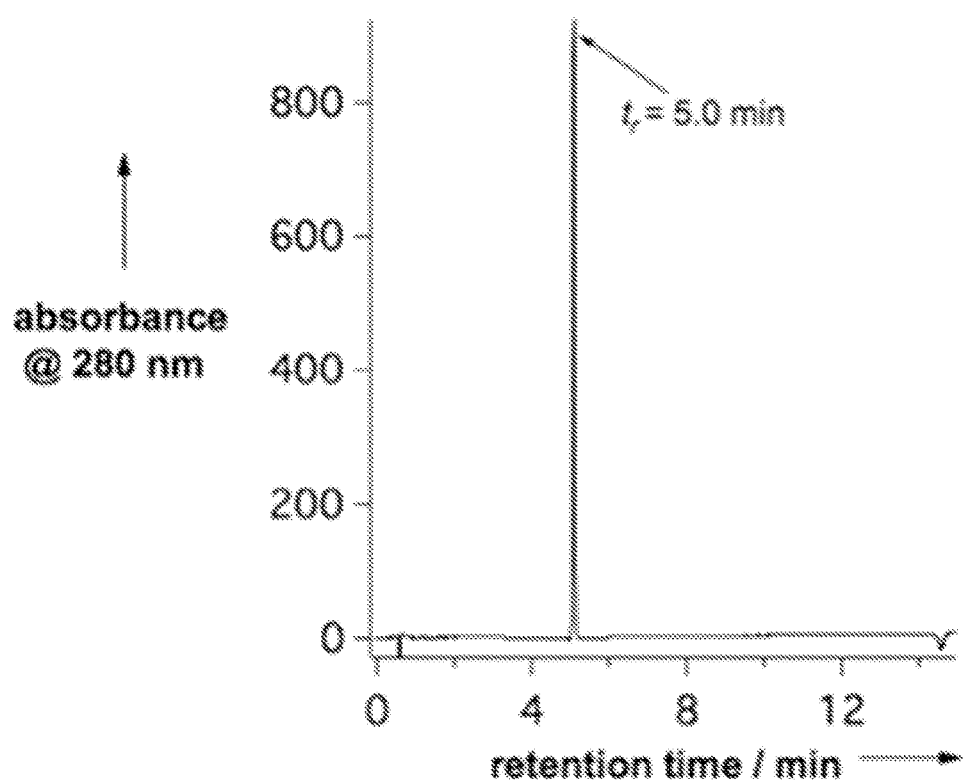
FIG. 1A shows HPLC analysis of pure Compound 1.

Protein disulfide isomerase (PDI) is a protein-folding chaperone that typically resides in the lumen of the endoplasmic reticulum. However, some extracellular sources have been reported, including on the exterior surface of platelets. Upon platelet activation, surface-associated PDI undergoes a shift in the oxidation state of active-site cysteine residues, favoring the enzymatically-active reduced form. When platelets become activated, they aggregate to form a hemostatic plug at the clot site. This aggregation process is facilitated by integrins located on the surface of activated platelets that can bind fibrinogen with high affinity only after being triggered by the enzymatic activity of PDI. Accordingly, PDI activity on the surface of activated platelets may be a useful biomarker of nascent blood clots.

Newly formed thrombi (blood clots) contain activated platelets, and, therefore, have PDI at the cell surface. Previously prepared imaging agents (e.g., EP2104-R) based on cyclized fibrin binding polypeptides were unable to distinguish between newly formed thrombi and older or mature thrombi which were no longer under active formation. Provided herein are compounds based on linear polypeptides having at least two disulfide residues which are capable of cyclizing upon exposure to PDI. Cyclization of the polypeptide activates the probe, allowing it to bind to the thrombus, and be detected using a variety of analytical methods. In the absence of PDI, the compounds having uncyclized polypeptides (i.e. linear polypeptides) do not bind to fibrin and are, therefore, not detected. Accordingly, the compounds provided herein provide methods for detecting active formation of thrombus by imaging those thrombi which contain activated platelets.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Compounds

The present application provides, inter alia, a compound of Formula (I):

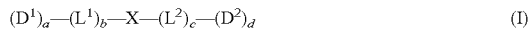

or a pharmaceutically acceptable salt thereof
wherein:
X is a linear polypeptide comprising at least two disulfide moieties, wherein upon cyclization of the at least two disulfide moieties, the resulting cyclized polypeptide is capable of binding to fibrin;
each $D^1$ is independently a detectable agent;
each $D^2$ is independently a detectable agent;
$L^1$ is a linker;
$L^2$ is a linker;
a is an integer from 0 to 4;
b is 0 or 1;
wherein if a is 0, b is 0;
c is 0 or 1;
d is an integer from 0 to 4;
wherein if d is 0, c is 0; and
wherein at least one of a and d is an integer from 1 to 4 (i.e., at least one of a or d is not 0).

X, as defined above, is a linear polypeptide comprising at least two disulfide moieties, wherein upon cyclization of the at least two disulfide moieties, the resulting cyclized polypeptide is capable of binding to fibrin. In some embodiments, X comprises two disulfide moieties.

In some embodiments, one or more of the disulfide moieties of X is a non-natural derivative of cysteine (e.g., two or more of the disulfide moieties of X are a non-natural derivative of cysteine, or the two disulfide moieties of X are both independently non-natural derivatives of cysteine). For example, in some embodiments, each disulfide moiety of X is independently a non-natural derivative of cysteine of Formula (A):

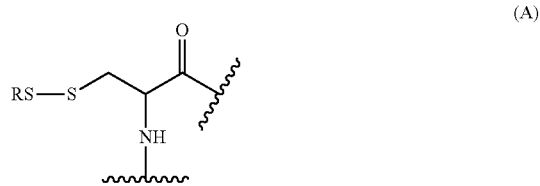

wherein each R is independently selected from the group consisting of $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-7 membered heterocycloalkyl, 4-10 membered heteroaryl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{a1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)R^{b1}$, $NR^{c1}S(=O)_2NR^{c1}R^{d1}$; wherein the $C_{1-6}$ alkyl, $C_{6-10}$ aryl, 4-7 membered heterocycloalkyl, and 4-7 membered heteroaryl are each optionally substituted with 1, 2, or 3 independently selected $R^A$ groups, wherein each $R^A$ is independently selected from the group consisting of OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino; and each $R^{a1}$, $R^{b1}$, $R^{c1}$, and $R^{d1}$ is independently selected from the group consisting of H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-7 membered heterocycloalkyl, and 4-10 membered heteroaryl.

In some embodiments, R is selected from the group consisting of a $C_{1-6}$ alkyl, $C_{2-6}$ alkenyl, and $C_{2-6}$ alkynyl, wherein each of the $C_{1-6}$ alkyl, $C_{2-6}$ alkenyl, and $C_{2-6}$ alkynyl are each optionally substituted with 1, 2, or 3 independently selected $R^A$ groups, wherein each $R^A$ is independently selected from the group consisting of OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, and $C_{1-3}$ alkylcarbonylamino. For example, R can be a $C_{1-6}$ alkyl optionally substituted with one $R^A$ group, wherein the $R^A$ is selected from the group consisting of OH, $NO_2$, CN, halo, $C_{1-3}$ alkoxy, $C_{1-3}$ haloalkoxy, amino, $C_{1-3}$ alkylamino, di($C_{1-3}$ alkyl)amino, carbamyl, and carboxy.

In some embodiments, each R is a residue of a non-natural derivative of cysteine. In some embodiments, each R is a non-natural derivative of cysteine (e.g., penicillamine). In some embodiments, each R is a $C_{6-10}$ aryl group (e.g., phenyl). In some embodiments, each R is a 4-10 membered heteroaryl group (e.g., 2-pyridine, 3-pyridine, or 4-pyridine). In some embodiments, each disulfide moiety of X is selected from the group consisting of:

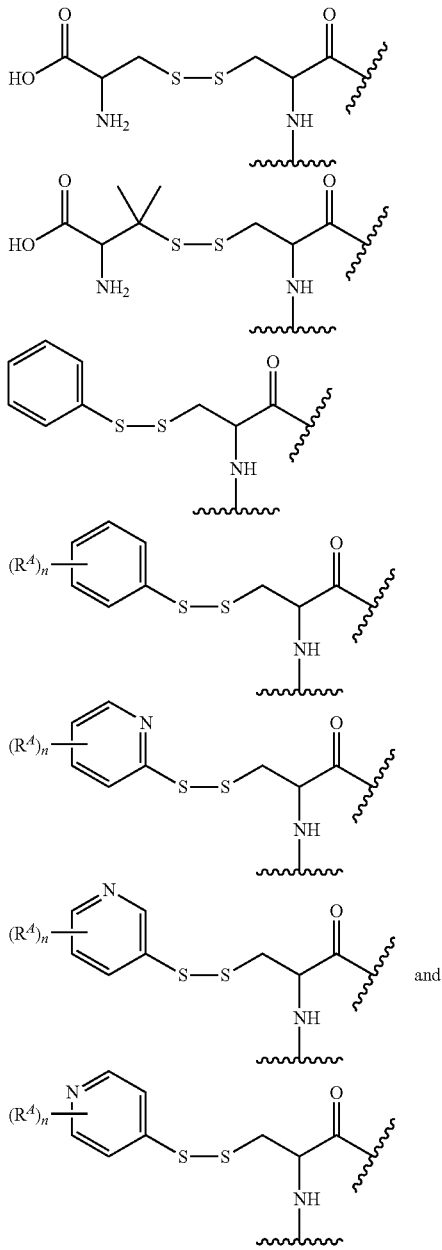

wherein n is an integer from 1 to 3. In some embodiments, n is 1. In some embodiments, n is 2. In some embodiments, n is 3.

In some embodiments, a is 1, b is 1, c is 1, and d is 1. In some embodiments, a is 2, b is 1, c is 1, and d is 1. In some embodiments, a is 3, b is 1, c is 1, and d is 1. In some embodiments, a is 4, b is 1, c is 1, and d is 1. In some embodiments, a is 2, b is 1, c is 1, and d is 2. In some embodiments, a is 3, b is 1, c is 1, and d is 2. In some embodiments, a is 4, b is 1, c is 1, and d is 2. In some embodiments, a is 3, b is 1, c is 1, and d is 2. In some embodiments, a is 4, b is 1, c is 1, and d is 2. In some embodiments, a is 2, b is 1, c is 1, and d is 3. In some embodiments, a is 3, b is 1, c is 1, and d is 3. In some embodiments, a is 3, b is 1, c is 1, and d is 4. In some embodiments, a is 4, b is 1, c is 1, and d is 4. In some embodiments, a is 1, b is 1, c is 1, and d is 2. In some embodiments, a is 1, b is 1, c is 1, and d is 3. In some embodiments, a is 1, b is 1, c is 1, and d is 4. In some embodiments, a is 1, b is 0, c is 0, and d is 1. In some embodiments, a is 1, b is 0, c is 1, and d is 1. In some embodiments, a is 2, b is 0, c is 1, and d is 1. In some embodiments, a is 3, b is 0, c is 1, and d is 1. In some embodiments, a is 4, b is 0, c is 1, and d is 1. In some embodiments, a is 2, b is 0, c is 1, and d is 2. In some embodiments, a is 3, b is 0, c is 1, and d is 2. In some embodiments, a is 4, b is 0, c is 1, and d is 2. In some embodiments, a is 3, b is 0, c is 1, and d is 2. In some embodiments, a is 4, b is 0, c is 1, and d is 2. In some embodiments, a is 2, b is 0, c is 1, and d is 3. In some embodiments, a is 3, b is 0, c is 1, and d is 3. In some embodiments, a is 3, b is 0, c is 1, and d is 4. In some embodiments, a is 4, b is 0, c is 1, and d is 4. In some embodiments, a is 1, b is 0, c is 1, and d is 2. In some embodiments, a is 1, b is 0, c is 1, and d is 3. In some embodiments, a is 1, b is 0, c is 1, and d is 4. In some embodiments, a is 1, b is 1, c is 1, and d is 1. In some embodiments, a is 2, b is 1, c is 1, and d is 1. In some embodiments, a is 3, b is 1, c is 1, and d is 1. In some embodiments, a is 4, b is 1, c is 0, and d is 1. In some embodiments, a is 2, b is 1, c is 0, and d is 2. In some embodiments, a is 3, b is 1, c is 0, and d is 2. In some embodiments, a is 4, b is 1, c is 0, and d is 2. In some embodiments, a is 3, b is 1, c is 0, and d is 2. In some embodiments, a is 4, b is 1, c is 0, and d is 2. In some embodiments, a is 2, b is 1, c is 0, and d is 3. In some embodiments, a is 3, b is 1, c is 0, and d is 3. In some embodiments, a is 3, b is 1, c is 0, and d is 4. In some embodiments, a is 4, b is 1, c is 0, and d is 4. In some embodiments, a is 1, b is 1, c is 0, and d is 2. In some embodiments, a is 1, b is 1, c is 0, and d is 3. In some embodiments, a is 1, b is 1, c is 0, and d is 4. In some embodiments, a is 0, b is 0, c is 0, and d is 1. In some embodiments, a is 0, b is 0, c is 0, and d is 2. In some embodiments, a is 0, b is 0, c is 0, and d is 3. In some embodiments, a is 0, b is 0, c is 0, and d is 4. In some embodiments, a is 0, b is 0, c is 1, and d is 1. In some embodiments, a is 0, b is 0, c is 1, and d is 2. In some embodiments, a is 0, b is 0, c is 1, and d is 3. In some embodiments, a is 0, b is 0, c is 1, and d is 4. In some embodiments, a is 1, b is 0, c is 0, and d is 0. In some embodiments, a is 2, b is 0, c is 0, and d is 0. In some embodiments, a is 3, b is 0, c is 0, and d is 0. In some embodiments, a is 4, b is 0, c is 0, and d is 0. In some embodiments, a is 1, b is 1, c is 0, and d is 0. In some embodiments, a is 2, b is 1, c is 0, and d is 0. In some embodiments, a is 3, b is 1, c is 0, and d is 0. In some embodiments, a is 4, b is 1, c is 0, and d is 0. In some embodiments, a and d are the same. In some embodiments, a and d are different.

In some embodiments, cyclic polypeptides which are known to bind to fibrin can be reduced to prepare a linear polypeptide, X as described herein. Non-limiting examples of such cyclic fibrin binding polypeptides can be found in WO 2008/071679; WO 2001/009188; U.S. Pat. No. 6,991, 775; U.S. Pat. No. 7,238,341; Starmans, L. W. E. et al., *Contrast Media & Mol. Imaging* (2013), 8: 229-237; Boros, E. et al., *Molecular Pharmaceutics* (2014), 11: 617-629; Hara, T. et al., *J. Am. Coll. Cardiol Img.* (2012) 5: 607-615; Ay, I. et al., *Circ. Cardiovasc. Imaging* (2014) 7: 697-705; Sirol, M. et al., *Atherosclerosis* (2005) 182: 79-85; Ciesienski, K. L. et al., *Molecular Pharmaceutics* (2013) 10(3): 1100-1110; and Blasi, F. et al., *J. Nucl. Med.* (2014) 55: 1-7.

In some embodiments, the binding affinity of the linear polypeptides comprising at least two disulfide moieties is about 25% of the binding affinity for the corresponding cyclized polypeptides, for example, less than about 25%, less than about 20%, less than about 15%, less than about 10%, less than about 5%, less than about 2%, or less than about 1%. In some embodiments, the linear polypeptides comprising at least two disulfide moieties do not bind to fibrin.

In some embodiments, X is a linear polypeptide comprising a sequence having at least 80% sequence identity to a sequence selected from the group consisting of:

```
                                            (SEQ ID NO: 1)
W-Q-P-C*-P-W-E-S-W-T-F-C*-W-D-P (SEQ ID NO: 2)
W-Q-P-C*-P-A-E-S-W-T-F-C*-W-D-P (SEQ ID NO: 3)
G-P-P-G-W-Q-P-C*-P-W-E-S-W-T-F-C*-W-D-P (SEQ ID NO: 4)
G-G-R-G-W-Q-P-C*-P-W-E-S-W-T-F-C*-W-D-P (SEQ ID NO: 5)
G-W-Q-P-C*-P-W-E-S-W-T-F-C*-W-D-P (SEQ ID NO: 6)
S-G-S-G-T-W-Q-P-C*-P-W-E-S-W-T-F-C*-W-D-P (SEQ ID NO: 7)
W-Q-P-C*-P-W-E-S-W-T-Cha-C*-W-D-P (SEQ ID NO: 8)
W-Q-P-C*-P-W-E-S-W-T-Ffe4-C*-W-D-P (SEQ ID NO: 9)
W-Q-P-C*-P-W-E-S-W-T-F34fe-C*-W-D-P (SEQ ID NO: 10)
R-G-W-Q-P-C*-P-W-E-S-W-T-F-C*-W-D-P (SEQ ID NO: 11)
R-W-Q-P-C*-P-W-E-S-W-T-F-C*-W-D-P (SEQ ID NO: 12)
S-G-S-G-S-G-S-G-W-Q-P-C*-P-W-E-S-W-T-F-C*-W-D-P (SEQ ID NO: 13)
K-K-G-W-Q-P-C*-P-W-E-S-W-T-F-C*-W-D-P (SEQ ID NO: 14)
K-G-K-G-K-G-W-Q-P-C*-P-W-E-S-W-T-F-C*-W-D-P (SEQ ID NO: 15)
S(Galnac)-W-Q-P-C*-P-W-E-S-W-T-F-C*-W-D-P (SEQ ID NO: 16)
Thf2ca-W-Q-P-C*-P-W-E-S-W-T-F-C*-W-D-P (SEQ ID NO: 17)
R-R-G-W-Q-P-C*-P-W-E-S-W-T-F-C*-W-D-P (SEQ ID NO: 18)
S(Galnac)-T-W-Q-P-C*-P-W-E-S-W-T-F-C*-W-D-P (SEQ ID NO: 19)
W-Q-P-C*-Hypt4-W-E-S-W-T-F-C*-W-D-P (SEQ ID NO: 20)
G-P-P-G-W-Q-P-C*-P-A-E-S-W-T-F-C*-W-D-P (SEQ ID NO: 21)
G-G-R-G-W-Q-P-C*-P-A-E-S-W-T-F-C*-W-D-P (SEQ ID NO: 22)
K-K-G-W-Q-P-C*-P-A-E-S-W-T-F-C*-W-D-P (SEQ ID NO: 23)
K-G-K-G-K-G-W-Q-P-C*-P-A-E-S-W-T-F-C*-W-D-P (SEQ ID NO: 24)
G-W-Q-P-C*-P-A-E-S-W-T-F-C*-W-D-P (SEQ ID NO: 25)
S-G-S-G-S-G-S-G-W-Q-P-C*-P-A-E-S-W-T-F-C*-W-D-P (SEQ ID NO: 26)
W-Q-P-C*-P-A-E-S-W-T-Ffe4-C*-W-D-P (SEQ ID NO: 27)
W-Q-P-C*-P-A-E-S-W-T-Cha-C*-W-D-P (SEQ ID NO: 28)
W-Q-P-C*-P-A-E-S-W-T-F34fe-C*-W-D-P (SEQ ID NO: 29)
Thf2ca-W-Q-P-C*-P-A-E-S-W-T-F-C*-W-D-P (SEQ ID NO: 30)
S-G-S-G-T-W-Q-P-C*-P-A-E-S-W-T-F-C*-W-D-P (SEQ ID NO: 31)
R-R-G-W-Q-P-C*-P-A-E-S-W-T-F-C*-W-D-P (SEQ ID NO: 32)
R-R-G-W-Q-P-C*-Hypt4-W-E-S-W-T-F-C*-W-D-P (SEQ ID NO: 33)
J-S-W-Q-P-C*-P-A-E-S-W-T-Cha-C*-W-D-P (SEQ ID NO: 34)
G-W-Q-P-C*-P-A-E-S-W-T-Cha-C*-W-D-P (SEQ ID NO: 35)
R-G-W-Q-P-C*-P-A-E-S-W-T-F-C*-W-D-P (SEQ ID NO: 36)
R-G-W-Q-P-C*-P-A-E-S-W-T-Cha-C*-W-D-P (SEQ ID NO: 37)
R-S-W-Q-P-C*-P-A-E-S-W-T-F-C*-W-D-P;
``` wherein C* is a group of Formula (A) as described above. In some embodiments, X is a linear polypeptide comprising a sequence selected from the group consisting of:

```
                                            (SEQ ID NO: 1)
W-Q-P-C*-P-W-E-S-W-T-F-C*-W-D-P (SEQ ID NO: 2)
W-Q-P-C*-P-A-E-S-W-T-F-C*-W-D-P (SEQ ID NO: 3)
G-P-P-G-W-Q-P-C*-P-W-E-S-W-T-F-C*-W-D-P (SEQ ID NO: 4)
G-G-R-G-W-Q-P-C*-P-W-E-S-W-T-F-C*-W-D-P (SEQ ID NO: 5)
G-W-Q-P-C*-P-W-E-S-W-T-F-C*-W-D-P (SEQ ID NO: 6)
S-G-S-G-T-W-Q-P-C*-P-W-E-S-W-T-F-C*-W-D-P (SEQ ID NO: 7)
W-Q-P-C*-P-W-E-S-W-T-Cha-C*-W-D-P (SEQ ID NO: 8)
W-Q-P-C*-P-W-E-S-W-T-Ffe4-C*-W-D-P (SEQ ID NO: 9)
W-Q-P-C*-P-W-E-S-W-T-F34fe-C*-W-D-P
```

```
                                             (SEQ ID NO: 10)
R-G-W-Q-P-C*-P-W-E-S-W-T-F-C*-W-D-P (SEQ ID NO: 11)
R-W-Q-P-C*-P-W-E-S-W-T-F-C*-W-D-P (SEQ ID NO: 12)
S-G-S-G-S-G-S-G-W-Q-P-C*-P-W-E-S-W-T-F-C*-W-D-P (SEQ ID NO: 13)
K-K-G-W-Q-P-C*-P-W-E-S-W-T-F-C*-W-D-P (SEQ ID NO: 14)
K-G-K-G-K-G-W-Q-P-C*-P-W-E-S-W-T-F-C*-W-D-P (SEQ ID NO: 15)
S(Galnac)-W-Q-P-C*-P-W-E-S-W-T-F-C*-W-D-P (SEQ ID NO: 16)
Thf2ca-W-Q-P-C*-P-W-E-S-W-T-F-C*-W-D-P (SEQ ID NO: 17)
R-R-G-G-W-Q-P-C*-P-W-E-S-W-T-F-C*-W-D-P (SEQ ID NO: 18)
S(Galnac)-T-W-Q-P-C*-P-W-E-S-W-T-F-C*-W-D-P (SEQ ID NO: 19)
W-Q-P-C*-Hypt4-W-E-S-W-T-F-C*-W-D-P (SEQ ID NO: 20)
G-P-P-G-W-Q-P-C*-P-A-E-S-W-T-F-C*-W-D-P (SEQ ID NO: 21)
G-G-R-G-W-Q-P-C*-P-A-E-S-W-T-F-C*-W-D-P (SEQ ID NO: 22)
K-K-G-W-Q-P-C*-P-A-E-S-W-T-F-C*-W-D-P (SEQ ID NO: 23)
K-G-K-G-K-G-W-Q-P-C*-P-A-E-S-W-T-F-C*-W-D-P (SEQ ID NO: 24)
G-W-Q-P-C*-P-A-E-S-W-T-F-C*-W-D-P (SEQ ID NO: 25)
S-G-S-G-S-G-S-G-W-Q-P-C*-P-A-E-S-W-T-F-C*-W-D-P (SEQ ID NO: 26)
W-Q-P-C*-P-A-E-S-W-T-Ffe4-C*-W-D-P (SEQ ID NO: 27)
W-Q-P-C*-P-A-E-S-W-T-Cha-C*-W-D-P (SEQ ID NO: 28)
W-Q-P-C*-P-A-E-S-W-T-F34fe-C*-W-D-P (SEQ ID NO: 29)
Thf2ca-W-Q-P-C*-P-A-E-S-W-T-F-C*-W-D-P (SEQ ID NO: 30)
S-G-S-G-T-W-Q-P-C*-P-A-E-S-W-T-F-C*-W-D-P (SEQ ID NO: 31)
R-R-G-G-W-Q-P-C*-P-A-E-S-W-T-F-C*-W-D-P (SEQ ID NO: 32)
R-R-G-G-W-Q-P-C*-Hypt4-W-E-S-W-T-F-C*-W-D-P (SEQ ID NO: 33)
J-S-W-Q-P-C*-P-A-E-S-W-T-Cha-C*-W-D-P (SEQ ID NO: 34)
G-W-Q-P-C*-P-A-E-S-W-T-Cha-C*-W-D-P (SEQ ID NO: 35)
R-G-W-Q-P-C*-P-A-E-S-W-T-F-C*-W-D-P (SEQ ID NO: 36)
R-G-W-Q-P-C*-P-A-E-S-W-T-Cha-C*-W-D-P (SEQ ID NO: 37)
R-S-W-Q-P-C*-P-A-E-S-W-T-F-C*-W-D-P;
``` wherein C* is a group of Formula (A) as described above.

In some embodiments, X is a linear polypeptide comprising a sequence having at least 80% sequence identity to a sequence:

```
                                             (SEQ ID NO: 38)
X1-X2-C*-P*-Y*-X3-L-C*-X4-X5-X6
``` wherein:

C* is a group of Formula (A) as described above;

P* is proline or a non-natural derivative thereof;

Y* is tyrosine or a non-natural derivative thereof;

$X_1$ is W, Y, F, S, Bip, Hx, Dpr, Cy, Gu, Ad, Hfe, 3-Pal, 4-Pal, DopaMe2, nY, dW, dF, F(3/4*), or Y(3*), wherein F(3/4*) is a phenylalanine substituted at either the 3 or the 4 position with a moiety such as $CH_3$, $CF_3$, $NH_2$, $CH_2NH_2$, CN, F, Cl, Br, I, Et, or Orne, and Y(3*) is a tyrosine substituted at the 3 position with a moiety such as F, Cl, Br, I, and $NO_2$;

$X_2$ is E, H, dE, S, H(Bzl), 2-Pal, Dpr, or Th;

$X_3$ is G or D;

$X_4$ is H, F, Y, or W;

$X_5$ is I, L, V, N, Bpa, Bal, Hfe, Nle, Tle, NV, Phg, Cha, Taz, Fua, Th, 4-Pal, or F(3/4*), wherein F(3/4*) is a phenylalanine substituted at either the 3 or the 4 position with a moiety such as $CF_3$, Et, iPr, or OMe; and $X_6$ is N, Q, I, L, or V, or not present.

In some embodiments, X is a linear polypeptide comprising (SEQ ID NO: 38).

In some embodiments, at least one of $X_1$, $X_2$, $X_5$, P*, and Y* is a non-natural derivative of an amino acid. For example, P* can be proline and Y* can be a non-natural derivative of tyrosine substituted at the 3 position with a moiety such as F, Cl, Br, I, or $NO_2$. Alternatively, P* can be a non-natural derivative of proline such as 4-hydroxyproline and Y* can be tyrosine.

Exemplary sequences of SEQ ID NO: 38 include:

```
                                             (SEQ ID NO: 39)
W-dE-C*-P(4-OH)-Y(3-Cl)-G-L-C*-W-I-Q (SEQ ID NO: 40)
Y-dE-C*-P(4-OH)-Y(3-Cl)-G-L-C*-Y-I-Q (SEQ ID NO: 41)
Y-dE-C*-P(4-OH)-Y(3-Cl)-G-L-C*-W-I-Q (SEQ ID NO: 42)
W-dE-C*-P(4-OH)-Y(3-Cl)-G-L-C*-Y-I-Q (SEQ ID NO: 43)
W-dE-C*-P(4-OH)-Y(3-Cl)-D-L-C*-W-I-Q (SEQ ID NO: 44)
Y-dE-C*-P(4-OH)-Y(3-Cl)-D-L-C*-Y-I-Q (SEQ ID NO: 45)
Y-dE-C*-P(4-OH)-Y(3-Cl)-D-L-C*-W-I-Q (SEQ ID NO: 46)
W-dE-C*-P(4-OH)-Y(3-Cl)-D-L-C*-Y-I-Q (SEQ ID NO: 47)
F(4-OMe)-H-C*-P(4-OH)-Y(3-Cl)-D-L-C*-H-I-L
```

```
                                                (SEQ ID NO: 48)
Y-H-C*-P(4-OH)-Y(3-Cl)-G-L-C*-W-I-Q (SEQ ID NO: 49)
W-dE-C*-P-Y(3-Cl)-G-L-C*-W-I-Q (SEQ ID NO: 50)
W-dE-C*-P(4-OH)-Y-G-L-C*-W-I-Q (SEQ ID NO: 51)
F-H-C*-P(4-OH)-Y(3-Cl)-D-L-C*-H-I-L (SEQ ID NO: 52)
F(4-OMe)-H-C*-P(4-OH)-Y(3-Cl)-D-L-C*-H-I (SEQ ID NO: 53)
F(4-OMe)-H-C*-P(4-OH)-Y(3-I)-D-L-C*-H-Bpa (SEQ ID NO: 54)
F-H-C*-P(4-OH)-Y(3-I)-D-L-C*-H-Hfe (SEQ ID NO: 55)
F-H-C*-P(4-OH)-Y(3-I)-D-L-C*-H-Bpa (SEQ ID NO: 56)
Y(3-Cl)-H-C*-P(4-OH)-Y(3-I)-D-L-C*-H-I (SEQ ID NO: 57)
F(4-OMe)-H-C*-P(4-OH)-Y(3-I)-D-L-C*-H-I-L (SEQ ID NO: 58)
F(4-OMe)-H(Bzl)-C*-P(4-OH)-Y(3-Cl)-D-L-C*-H-Bpa (SEQ ID NO: 59)
F-H-C*-P(4-OH)-Y(3-Cl)-D-L-C*-H-I (SEQ ID NO: 60)
F(4-OMe)-H-C*-P(4-OH)-Y(3-I)-D-L-C*-H-I (SEQ ID NO: 61)
3Pal-H-C*-P(4-OH)-Y(3-I)-D-L-C*-H-I (SEQ ID NO: 62)
4Pal-H-C*-P(4-OH)-Y(3-I)-D-L-C*-H-I (SEQ ID NO: 63)
F(4-F)-H-C*-P(4-OH)-Y(3-I)-D-L-C*-H-I (SEQ ID NO: 64)
Y(3-I)-H-C*-P(4-OH)-Y(3-I)-D-L-C*-H-I (SEQ ID NO: 65)
F-H-C*-P(4-OH)-Y(3-I)-D-L-C*-H-I-L (SEQ ID NO: 66)
F(4-OMe)-H-C*-P(4-OH)-Y(3-Cl)-D-L-C*-H-Bpa-L (SEQ ID NO: 67)
F(4-OMe)-H-C*-P(4-OH)-Y(3-I)-D-L-C*-H-Bpa-L (SEQ ID NO: 68)
F-H(Bzl)-C*-P(4-OH)-Y(3-Cl)-D-L-C*-H-I-L (SEQ ID NO: 69)
1Nal-H-C*-P(4-OH)-Y(3-I)-D-L-C*-H-I (SEQ ID NO: 70)
MY-H-C*-P(4-OH)-Y(3-I)-D-L-C*-H-I (SEQ ID NO: 71)
F(4-OMe)-H(Bzl)-C*-P(4-OH)-Y(3-I)-D-L-C*-H-Bpa (SEQ ID NO: 72)
F(4-OMe)-H(Bzl)-C*-P(4-OH)-Y(3-Cl)-D-L-C*-H-I (SEQ ID NO: 73)
F-H-C*-P(4-OH)-Y(3-I)-D-L-C*-3Pal-I (SEQ ID NO: 74)
F(4-I)-H-C*-P(4-OH)-Y(3-I)-D-L-C*-H-I (SEQ ID NO: 75)
F(4-Br)-H-C*-P(4-OH)-Y(3-I)-D-L-C*-H-I (SEQ ID NO: 76)
F(4-Me)-H-C*-P(4-OH)-Y(3-I)-D-L-C*-H-I (SEQ ID NO: 77)
F(4-CF3)-H-C*-P(4-OH)-Y(3-I)-D-L-C*-H-I (SEQ ID NO: 78)
F(4-CN)-H-C*-P(4-OH)-Y(3-I)-D-L-C*-H-I (SEQ ID NO: 79)
Y(3-NO2)-H-C*-P(4-OH)-Y(3-I)-D-L-C*-H-I (SEQ ID NO: 80)
Y(2-F)-H-C*-P(4-OH)-Y(3-I)-D-L-C*-H-I (SEQ ID NO: 81)
F(4-CH2NH2)-H-C*-P(4-OH)-Y(3-I)-D-L-C*-H-I (SEQ ID NO: 82)
F(4-NH2)-H-C*-P(4-OH)-Y(3-I)-D-L-C*-H-I (SEQ ID NO: 83)
F(34-F2)-H-C*-P(4-OH)-Y(3-I)-D-L-C*-H-I (SEQ ID NO: 84)
DopaMe2-H-C*-P(4-OH)-Y(3-I)-D-L-C*-H-I (SEQ ID NO: 85)
F(2-OMe)-H-C*-P(4-OH)-Y(3-I)-D-L-C*-H-I (SEQ ID NO: 86)
F(3-Me)-H-C*-P(4-OH)-Y(3-I)-D-L-C*-H-I (SEQ ID NO: 87)
F-H-C*-P(4-OH)-Y(3-I)-D-L-C*-H-I (SEQ ID NO: 88)
F-H-C*-P(4-OH)-Y(3-I)-D-L-C*-H-F(3-CF3)

(SEQ ID NO: 89)
F(3-CF3)-H-C*-P(4-OH)-Y(3-I)-D-L-C*-H-I (SEQ ID NO: 90)
F(3-OMe)-H-C*-P(4-OH)-Y(3-I)-D-L-C*-H-I (SEQ ID NO: 91)
Hfe-H-C*-P(4-OH)-Y(3-I)-D-L-C*-H-I (SEQ ID NO: 92)
nY-H-C*-P(4-OH)-Y(3-I)-D-L-C*-H-I (SEQ ID NO: 93)
W-E-C*-P(4-OH)-Y(3-Cl)-G-L-C*-W-I-Q (SEQ ID NO: 94)
F-H-C*-P(4-OH)-Y(3-I)-D-L-C*-H-I-L (SEQ ID NO: 95)
F(4-OMe)-H(Bzl)-C*-P(4-OH)-Y(3-I)-D-L-C*-H-I (SEQ ID NO: 96)
F-H-C*-P(4-OH)-Y(3-I)-D-L-C*-H-Nle (SEQ ID NO: 97)
F-H-C*-P(4-OH)-Y(3-I)-D-L-C*-H-Tle (SEQ ID NO: 98)
F-H-C*-P(4-OH)-Y(3-I)-D-L-C*-H-F(4-CF3)

(SEQ ID NO: 99)
F-H-C*-P(4-OH)-Y(3-I)-D-L-C*-H-Bip (SEQ ID NO: 100)
F-H-C*-P(4-OH)-Y(3-I)-D-L-C*-H-F(4-Et)

(SEQ ID NO: 101)
F-H-C*-P(4-OH)-Y(3-I)-D-L-C*-H-F(4-OMe)
```

```
                                                  (SEQ ID NO: 102)
F-H-C*-P(4-OH)-Y(3-I)-D-L-C*-H-F(3-OMe)

(SEQ ID NO: 103)
F(F5)-H-C*-P(4-OH)-Y(3-I)-D-L-C*-H-I (SEQ ID NO: 104)
F-H-C*-P(4-OH)-Y(3-F)-D-L-C*-H-I-L (SEQ ID NO: 105)
W-E-C*-P(4-OH)-Y(3-Cl)-G-L-C*-W-I-Q (SEQ ID NO: 106)
T-dE-C*-P(4-OH)-Y(3-Cl)-G-L-C*-W-I-Q (SEQ ID NO: 107)
F-H-C*-P-Y(3-Cl)-D-L-C*-H-I-L (SEQ ID NO: 108)
Y(26-Me)-H-C*-P(4-OH)-Y(3-I)-D-L-C*-H-I (SEQ ID NO: 109)
W-E-C*-P(4-OH)-Y(3-Cl)-G-L-C*-H-I-Q (SEQ ID NO: 110)
dF-dE-C*-P(4-OH)-Y(3-Cl)-G-L-C*-W-I-Q (SEQ ID NO: 111)
Y-E-C*-P(4-OH)-Y(3-Cl)-G-L-C*-Y-I-Q (SEQ ID NO: 112)
W-E-C*-P(4-OH)-Y(3-Cl)-G-L-C*-F-I-Q (SEQ ID NO: 113)
H-dE-C*-P(4-OH)-Y(3-Cl)-G-L-C*-W-I-Q (SEQ ID NO: 114)
F-H-C*-P(4-OH)-Y(3-I)-D-L-C*-H-I-L (SEQ ID NO: 115)
W-E-C*-P-Y-G-L-C*-W-I-Q (SEQ ID NO: 116)
F-H-C*-P(4-OH)-Y(3-I)-D-L-C*-H-nV (SEQ ID NO: 117)
F-H-C*-P(4-OH)-Y(3-I)-D-L-C*-H-Phg (SEQ ID NO: 118)
F-H-C*-P(4-OH)-Y(3-I)-D-L-C*-H-F(3-Me)

(SEQ ID NO: 119)
F-H-C*-P(4-OH)-Y(3-I)-D-L-C*-4Pal-I (SEQ ID NO: 120)
S-dE-C*-P(4-OH)-Y(3-Cl)-G-L-C*-W-I-Q (SEQ ID NO: 121)
W-E-C*-P(4-OH)-Y(3-Cl)-G-L-C*-Y-I-Q (SEQ ID NO: 122)
Y-E-C*-P(4-OH)-Y(3-Cl)-G-L-C*-W-I-Q (SEQ ID NO: 123)
F-dE-C*-P(4-OH)-Y(3-Cl)-G-L-C*-W-I-Q (SEQ ID NO: 124)
F-H-C*-P-Y-D-L-C*-H-I-L (SEQ ID NO: 125)
F-H-C*-P(4-OH)-Y(3-I)-D-L-C*-H-I-L (SEQ ID NO: 126)
F-H-C*-P(4-OH)-Y-D-L-C*-H-Bpa (SEQ ID NO: 127)
F-H-C*-P(4-OH)-Y(3-Cl)-D-L-C*-H-I-L (SEQ ID NO: 128)
S(Bzl)-H-C*-P-Y-D-L-C*-H-I-L (SEQ ID NO: 129)
H-E-C*-P(4-OH)-Y(3-Cl)-G-L-C*-H-I-Q (SEQ ID NO: 130)
F(4-OMe)-H-C*-P(4-OH)-Y-D-L-C*-H-L (SEQ ID NO: 131)
F-H-C*-P(4-OH)-Y(3-I)-D-L-C*-Bpa-I (SEQ ID NO: 132)
Ad-H-C*-P(4-OH)-Y(3-I)-D-L-C*-H-I (SEQ ID NO: 133)
F-H-C*-P(4-OH)-Y(3-Cl)-F-L-C*-H-I-L (SEQ ID NO: 134)
F-E-C*-P(4-OH)-Y(3-Cl)-G-L-C*-W-I-Q (SEQ ID NO: 135)
F-H-C*-P(4-OH)-Y(3-Cl)-2-Nal-L-C*-H-I-L (SEQ ID NO: 136)
F-H-C*-P(4-OH)-Y-D-L-C*-H-I-L (SEQ ID NO: 137)
Hfe-H-C*-P(4-OH)-Y-D-L-C*-H-I-L (SEQ ID NO: 138)
Bip-H-C*-P(4-OH)-Y-D-L-C*-H-I-L (SEQ ID NO: 139)
W-E-C*-P-Y-G-L-C*-W-I-Q (SEQ ID NO: 140)
F(4-OMe)-W-C*-P(4-OH)-Y(3-I)-D-L-C*-H-I (SEQ ID NO: 141)
F-H-C*-P(4-OH)-Y(3-I)-D-L-C*-2Pal-I (SEQ ID NO: 142)
F-H-C*-P(4-OH)-Y(3-I)-D-L-C*-Taz-I (SEQ ID NO: 143)
F-H-C*-P(4-OH)-Y(3-I)-D-L-C*-Dht-I (SEQ ID NO: 144)
Gu-H-C*-P(4-QH)-Y(3-I)-D-L-C*-H-I
```

In some embodiments, X is a linear polypeptide comprising a sequence selected from the group consisting of:

```
                                                  (SEQ ID NO: 39)
W-dE-C*-P(4-OH)-Y(3-Cl)-G-L-C*-W-I-Q (SEQ ID NO: 40)
Y-dE-C*-P(4-OH)-Y(3-Cl)-G-L-C*-Y-I-Q (SEQ ID NO: 41)
Y-dE-C*-P(4-OH)-Y(3-Cl)-G-L-C*-W-I-Q (SEQ ID NO: 42)
W-dE-C*-P(4-OH)-Y(3-Cl)-G-L-C*-Y-I-Q (SEQ ID NO: 43)
W-dE-C*-P(4-OH)-Y(3-Cl)-D-L-C*-W-I-Q (SEQ ID NO: 44)
Y-dE-C*-P(4-OH)-Y(3-Cl)-D-L-C*-Y-I-Q (SEQ ID NO: 45)
Y-dE-C*-P(4-OH)-Y(3-Cl)-D-L-C*-W-I-Q (SEQ ID NO: 46)
W-dE-C*-P(4-OH)-Y(3-Cl)-D-L-C*-Y-I-Q (SEQ ID NO: 47)
F(4-OMe)-H-C*-P(4-OH)-Y(3-Cl)-D-L-C*-H-I-L
```

-continued

Y-H-C*-P(4-OH)-Y(3-Cl)-G-L-C*-W-I-Q (SEQ ID NO: 48)

W-dE-C*-P-Y(3-Cl)-G-L-C*-W-I-Q (SEQ ID NO: 49)

W-dE-C*-P(4-OH)-Y-G-L-C*-W-I-Q (SEQ ID NO: 50)

F-H-C*-P(4-OH)-Y(3-Cl)-D-L-C*-H-I-L (SEQ ID NO: 51)

F(4-OMe)-H-C*-P(4-OH)-Y(3-Cl)-D-L-C*-H-I (SEQ ID NO: 52)

F(4-OMe)-H-C*-P(4-OH)-Y(3-I)-D-L-C*-H-Bpa (SEQ ID NO: 53)

F-H-C*-P(4-OH)-Y(3-I)-D-L-C*-H-Hfe (SEQ ID NO: 54)

F-H-C*-P(4-OH)-Y(3-I)-D-L-C*-H-Bpa (SEQ ID NO: 55)

Y(3-Cl)-H-C*-P(4-OH)-Y(3-I)-D-L-C*-H-I (SEQ ID NO: 56)

F(4-OMe)-H-C*-P(4-OH)-Y(3-I)-D-L-C*-H-I-L (SEQ ID NO: 57)

F(4-OMe)-H(Bzl)-C*-P(4-OH)-Y(3-Cl)-D-L-C*-H-Bpa (SEQ ID NO: 58)

F-H-C*-P(4-OH)-Y(3-Cl)-D-L-C*-H-I (SEQ ID NO: 59)

F(4-OMe)-H-C*-P(4-OH)-Y(3-I)-D-L-C*-H-I (SEQ ID NO: 60)

3Pal-H-C*-P(4-OH)-Y(3-I)-D-L-C*-H-I (SEQ ID NO: 61)

4Pal-H-C*-P(4-OH)-Y(3-I)-D-L-C*-H-I (SEQ ID NO: 62)

F(4-F)-H-C*-P(4-OH)-Y(3-I)-D-L-C*-H-I (SEQ ID NO: 63)

Y(3-I)-H-C*-P(4-OH)-Y(3-I)-D-L-C*-H-I (SEQ ID NO: 64)

F-H-C*-P(4-OH)-Y(3-I)-D-L-C*-H-I-L (SEQ ID NO: 65)

F(4-OMe)-H-C*-P(4-OH)-Y(3-Cl)-D-L-C*-H-Bpa-L (SEQ ID NO: 66)

F(4-OMe)-H-C*-P(4-OH)-Y(3-I)-D-L-C*-H-Bpa-L (SEQ ID NO: 67)

F-H(Bzl)-C*-P(4-OH)-Y(3-Cl)-D-L-C*-H-I-L (SEQ ID NO: 68)

1Nal-H-C*-P(4-OH)-Y(3-I)-D-L-C*-H-I (SEQ ID NO: 69)

MY-H-C*-P(4-OH)-Y(3-I)-D-L-C*-H-I (SEQ ID NO: 70)

F(4-OMe)-H(Bzl)-C*-P(4-OH)-Y(3-I)-D-L-C*-H-Bpa (SEQ ID NO: 71)

F(4-OMe)-H(Bzl)-C*-P(4-OH)-Y(3-Cl)-D-L-C*-H-I (SEQ ID NO: 72)

F-H-C*-P(4-OH)-Y(3-I)-D-L-C*-3Pal-I (SEQ ID NO: 73)

F(4-I)-H-C*-P(4-OH)-Y(3-I)-D-L-C*-H-I (SEQ ID NO: 74)

F(4-Br)-H-C*-P(4-OH)-Y(3-I)-D-L-C*-H-I (SEQ ID NO: 75)

F(4-Me)-H-C*-P(4-OH)-Y(3-I)-D-L-C*-H-I (SEQ ID NO: 76)

F(4-CF3)-H-C*-P(4-OH)-Y(3-I)-D-L-C*-H-I (SEQ ID NO: 77)

F(4-CN)-H-C*-P(4-OH)-Y(3-I)-D-L-C*-H-I (SEQ ID NO: 78)

Y(3-NO2)-H-C*-P(4-OH)-Y(3-I)-D-L-C*-H-I (SEQ ID NO: 79)

Y(2-F)-H-C*-P(4-OH)-Y(3-I)-D-L-C*-H-I (SEQ ID NO: 80)

F(4-CH2NH2)-H-C*-P(4-OH)-Y(3-I)-D-L-C*-H-I (SEQ ID NO: 81)

F(4-NH2)-H-C*-P(4-OH)-Y(3-I)-D-L-C*-H-I (SEQ ID NO: 82)

F(34-F2)-H-C*-P(4-OH)-Y(3-I)-D-L-C*-H-I (SEQ ID NO: 83)

DopaMe2-H-C*-P(4-OH)-Y(3-I)-D-L-C*-H-I (SEQ ID NO: 84)

F(2-OMe)-H-C*-P(4-OH)-Y(3-I)-D-L-C*-H-I (SEQ ID NO: 85)

F(3-Me)-H-C*-P(4-OH)-Y(3-I)-D-L-C*-H-I (SEQ ID NO: 86)

F-H-C*-P(4-OH)-Y(3-I)-D-L-C*-H-I (SEQ ID NO: 87)

F-H-C*-P(4-OH)-Y(3-I)-D-L-C*-H-F(3-CF3) (SEQ ID NO: 88)

F(3-CF3)-H-C*-P(4-OH)-Y(3-I)-D-L-C*-H-I (SEQ ID NO: 89)

F(3-OMe)-H-C*-P(4-OH)-Y(3-I)-D-L-C*-H-I (SEQ ID NO: 90)

Hfe-H-C*-P(4-OH)-Y(3-I)-D-L-C*-H-I (SEQ ID NO: 91)

nY-H-C*-P(4-OH)-Y(3-I)-D-L-C*-H-I (SEQ ID NO: 92)

W-E-C*-P(4-OH)-Y(3-Cl)-G-L-C*-W-I-Q (SEQ ID NO: 93)

F-H-C*-P(4-OH)-Y(3-I)-D-L-C*-H-I-L (SEQ ID NO: 94)

F(4-OMe)-H(Bzl)-C*-P(4-OH)-Y(3-I)-D-L-C*-H-I (SEQ ID NO: 95)

F-H-C*-P(4-OH)-Y(3-I)-D-L-C*-H-Nle (SEQ ID NO: 96)

F-H-C*-P(4-OH)-Y(3-I)-D-L-C*-H-Tle (SEQ ID NO: 97)

F-H-C*-P(4-OH)-Y(3-I)-D-L-C*-H-F(4-CF3) (SEQ ID NO: 98)

F-H-C*-P(4-OH)-Y(3-I)-D-L-C*-H-Bip (SEQ ID NO: 99)

F-H-C*-P(4-OH)-Y(3-I)-D-L-C*-H-F(4-Et) (SEQ ID NO: 100)

F-H-C*-P(4-OH)-Y(3-I)-D-L-C*-H-F(4-OMe) (SEQ ID NO: 101)

-continued

F-H-C*-P(4-OH)-Y(3-I)-D-L-C*-H-F(3-OMe) (SEQ ID NO: 102)

F(F5)-H-C*-P(4-OH)-Y(3-I)-D-L-C*-H-I (SEQ ID NO: 103)

F-H-C*-P(4-OH)-Y(3-F)-D-L-C*-H-I-L (SEQ ID NO: 104)

W-E-C*-P(4-OH)-Y(3-Cl)-G-L-C*-W-I-Q (SEQ ID NO: 105)

T-dE-C*-P(4-OH)-Y(3-Cl)-G-L-C*-W-I-Q (SEQ ID NO: 106)

F-H-C*-P-Y(3-Cl)-D-L-C*-H-I-L (SEQ ID NO: 107)

Y(26-Me)-H-C*-P(4-OH)-Y(3-I)-D-L-C*-H-I (SEQ ID NO: 108)

W-E-C*-P(4-OH)-Y(3-Cl)-G-L-C*-H-I-Q (SEQ ID NO: 109)

dF-dE-C*-P(4-OH)-Y(3-Cl)-G-L-C*-W-I-Q (SEQ ID NO: 110)

Y-E-C*-P(4-OH)-Y(3-Cl)-G-L-C*-Y-I-Q (SEQ ID NO: 111)

W-E-C*-P(4-OH)-Y(3-Cl)-G-L-C*-F-I-Q (SEQ ID NO: 112)

H-dE-C*-P(4-OH)-Y(3-Cl)-G-L-C*-W-I-Q (SEQ ID NO: 113)

F-H-C*-P(4-OH)-Y(3-I)-D-L-C*-H-I-L (SEQ ID NO: 114)

W-E-C*-P-Y-G-L-C*-W-I-Q (SEQ ID NO: 115)

F-H-C*-P(4-OH)-Y(3-I)-D-L-C*-H-nV (SEQ ID NO: 116)

F-H-C*-P(4-OH)-Y(3-I)-D-L-C*-H-Phg (SEQ ID NO: 117)

F-H-C*-P(4-OH)-Y(3-I)-D-L-C*-H-F(3-Me) (SEQ ID NO: 118)

F-H-C*-P(4-OH)-Y(3-I)-D-L-C*-4Pal-I (SEQ ID NO: 119)

S-dE-C*-P(4-OH)-Y(3-Cl)-G-L-C*-W-I-Q (SEQ ID NO: 120)

W-E-C*-P(4-OH)-Y(3-Cl)-G-L-C*-Y-I-Q (SEQ ID NO: 121)

Y-E-C*-P(4-OH)-Y(3-Cl)-G-L-C*-W-I-Q (SEQ ID NO: 122)

F-dE-C*-P(4-OH)-Y(3-Cl)-G-L-C*-W-I-Q (SEQ ID NO: 123)

F-H-C*-P-Y-D-L-C*-H-I-L (SEQ ID NO: 124)

F-H-C*-P(4-OH)-Y(3-I)-D-L-C*-H-I-L (SEQ ID NO: 125)

F-H-C*-P(4-OH)-Y-D-L-C*-H-Bpa (SEQ ID NO: 126)

F-H-C*-P(4-OH)-Y(3-Cl)-G-L-C*-H-I-L (SEQ ID NO: 127)

S(Bzl)-H-C*-P-Y-D-L-C*-H-I-L (SEQ ID NO: 128)

H-E-C*-P(4-OH)-Y(3-Cl)-G-L-C*-H-I-Q (SEQ ID NO: 129)

F(4-OMe)-H-C*-P(4-OH)-Y-D-L-C*-H-I-L (SEQ ID NO: 130)

F-H-C*-P(4-OH)-Y(3-I)-D-L-C*-Bpa-I (SEQ ID NO: 131)

Ad-H-C*-P(4-OH)-Y(3-I)-D-L-C*-H-I (SEQ ID NO: 132)

F-H-C*-P(4-OH)-Y(3-Cl)-F-L-C*-H-I-L (SEQ ID NO: 133)

F-E-C*-P(4-OH)-Y(3-Cl)-G-L-C*-W-I-Q (SEQ ID NO: 134)

F-H-C*-P(4-OH)-Y(3-Cl)-2-Nal-L-C*-H-I-L (SEQ ID NO: 135)

F-H-C*-P(4-OH)-Y-D-L-C*-H-I-L (SEQ ID NO: 136)

Hfe-H-C*-P(4-OH)-Y-D-L-C*-H-I-L (SEQ ID NO: 137)

Bip-H-C*-P(4-OH)-Y-D-L-C*-H-I-L (SEQ ID NO: 138)

W-E-C*-P-Y-G-L-C*-W-I-Q (SEQ ID NO: 139)

F(4-OMe)-W-C*-P(4-OH)-Y(3-I)-D-L-C*-H-I (SEQ ID NO: 140)

FH-C*-P(4-OH)-Y(3-I)-D-L-C*-2Pal-I (SEQ ID NO: 141)

F-H-C*-P(4-OH)-Y(3-I)-D-L-C*-Taz-I (SEQ ID NO: 142)

F-H-C*-P(4-OH)-Y(3-I)-D-L-C*-Dht-I (SEQ ID NO: 143)

Gu-H-C*-P(4-OH)-Y(3-I)-D-L-C*-H-I. (SEQ ID NO: 144)

In some embodiments, X is a linear polypeptide comprising a sequence having at least 80% sequence identity to a sequence:

C*-P*-Y*-$X_1$-L-C* (SEQ ID NO: 145)

wherein $X_1$ is G or D

C* is a group of Formula (A) as described above;

P* is proline or its non-natural derivative 4-hydroxyproline; and

Y* is tyrosine or a non-natural derivative of tyrosine substituted at the 3 position with a moiety selected from the group consisting of F, Cl, Br, I, and $NO_2$;

provided that at least one of P* or y* is a non-natural derivative of the respective amino acid.

In some embodiments, X is a linear polypeptide comprising (SEQ ID NO: 145).

In some embodiments, X is a linear polypeptide comprising a sequence having at least 80% sequence identity to a sequence:

C*-D-Y-Y-G-T-C*-$X_{10}$ (SEQ ID NO: 146)

wherein:

C* is a group of Formula (A) as described above;

X$_{10}$ is selected from the group consisting of n(decyl)G, n(4-PhBu)G, MeL, Bpa, Bip, Me-Bip, F(4*), F(3-Me), F(3,4-difluoro), Amh, Hfe, Y(3,5-di-iodo), Pff, lNal, dlNal, and MeL, wherein F(4*) is a phenylalanine substituted at the 4 position with a moiety selected from the group consisting of Et, CF$_3$, I, and iPr.

In some embodiments, X is a linear polypeptide comprising (SEQ ID NO: 146).

In some embodiments, X is a linear polypeptide comprising a sequence having at least 80% sequence identity to a sequence:

```
                                        (SEQ ID NO: 147)
X1-P*-C*-D-Y-Y-G-T-C*-X10-X11
``` wherein X$_1$ is any natural or non-natural amino acid,

C* is a group of Formula (A) as described above;

P* is proline or a non-natural derivative thereof, and wherein X$_{11}$ is selected from the group consisting of D, dD, βD, Inp, Nip, Me-D, dC, Cop, and Cmp.

In some embodiments, X is a linear polypeptide comprising (SEQ ID NO: 147).

Exemplary sequences of SEQ ID NO: 147 include:

```
                                        (SEQ ID NO: 148)
L-P-C*-D-Y-Y-G-T-C*-n(Decyl)G-dD (SEQ ID NO: 149)
L-P-C*-D-Y-Y-G-T-C*-n(Decyl)G-D (SEQ ID NO: 150)
L-P-C*-D-Y-Y-G-T-C*-Bip-D (SEQ ID NO: 151)
L-P-C*-D-Y-Y-G-T-C*-Bip-dD (SEQ ID NO: 152)
L-P-C*-D-Y-Y-G-T-C*-MeL-Inp (SEQ ID NO: 153)
L-P-C*-D-Y-Y-G-T-C*-MeL-Cmp (SEQ ID NO: 154)
L-P-C*-D-Y-Y-G-T-C*-MeBip-D (SEQ ID NO: 155)
L-P*-C*-D-Y-Y-G-T-C*-n(Decyl)G-dD (SEQ ID NO: 156)
L-P*-C*-D-Y-Y-G-T-C*-n(Decyl)G-D (SEQ ID NO: 157)
L-P*-C*-D-Y-Y-G-T-C*-MeL-Inp (SEQ ID NO: 158)
L-P*-C*-D-Y-Y-G-T-C*-Bip-D (SEQ ID NO: 159)
L-P*-C*-D-Y-Y-G-T-C*-Bip-dD (SEQ ID NO: 160)
L-P*-C*-D-Y-Y-G-T-C*-Me-Bip-D (SEQ ID NO: 161)
L-P*-C*-D-Y-Y-G-T-C*-MeL-Cmp (SEQ ID NO: 162)
L-P*-C*-D-Y-Y-G-T-C*-L-D (SEQ ID NO: 163)
Cha-P*-C*-D-Y-Y-G-T-C*-Bip-D.
```

In some embodiments, X is a linear polypeptide comprising a sequence selected from the group consisting of:

```
                                        (SEQ ID NO: 148)
L-P-C*-D-Y-Y-G-T-C*-n(Decyl)G-dD (SEQ ID NO: 149)
L-P-C*-D-Y-Y-G-T-C*-n(Decyl)G-D (SEQ ID NO: 150)
L-P-C*-D-Y-Y-G-T-C*-Bip-D (SEQ ID NO: 151)
L-P-C*-D-Y-Y-G-T-C*-Bip-dD (SEQ ID NO: 152)
L-P-C*-D-Y-Y-G-T-C*-MeL-Inp (SEQ ID NO: 153)
L-P-C*-D-Y-Y-G-T-C*-MeL-Cmp (SEQ ID NO: 154)
L-P-C*-D-Y-Y-G-T-C*-MeBip-D (SEQ ID NO: 155)
L-P*-C*-D-Y-Y-G-T-C*-n(Decyl)G-dD (SEQ ID NO: 156)
L-P*-C*-D-Y-Y-G-T-C*-n(Decyl)G-D (SEQ ID NO: 157)
L-P*-C*-D-Y-Y-G-T-C*-MeL-Inp (SEQ ID NO: 158)
L-P*-C*-D-Y-Y-G-T-C*-Bip-D (SEQ ID NO: 159)
L-P*-C*-D-Y-Y-G-T-C*-Bip-dD (SEQ ID NO: 160)
L-P*-C*-D-Y-Y-G-T-C*-Me-Bip-D (SEQ ID NO: 161)
L-P*-C*-D-Y-Y-G-T-C*-MeL-Cmp (SEQ ID NO: 162)
L-P*-C*-D-Y-Y-G-T-C*-L-D (SEQ ID NO: 163)
Cha-P*-C*-D-Y-Y-G-T-C*-Bip-D.
```

In some embodiments, X is a linear polypeptide comprising a sequence having at least 80% sequence identity to a sequence selected from the group consisting of:

```
                                        (SEQ ID NO: 164)
Y-dE-C*-P(4-OH)-3C-L-Y-G-L-C*-Y-I-Q (SEQ ID NO: 165)
R-W-Q-P-C*-P-A-E-S-W-T-Cha-C*-W-D-P (SEQ ID NO: 166)
R-W-Q-P-C*-P-A-E-S-W-T-Cha-C*-W-D-P-G-G-G-K.
```

In some embodiments, X is a linear polypeptide comprising a sequence selected from the group consisting of:

```
                                        (SEQ ID NO: 164)
Y-dE-C*-P(4-OH)-3C-L-Y-G-L-C*-Y-I-Q (SEQ ID NO: 165)
R-W-Q-P-C*-P-A-E-S-W-T-Cha-C*-W-D-P (SEQ ID NO: 166)
R-W-Q-P-C*-P-A-E-S-W-T-Cha-C*-W-D-P-G-G-G-K.
```

In some embodiments, X is a linear polypeptide comprising a sequence having at least 80% sequence identity to a sequence:

$$C^*-X_2-X_3-Y-X_5-X_6-C^* \quad \text{(SEQ ID NO: 167)}$$

wherein:

C* is a group of Formula (A) as described above;

$X_2$ is A, E, F, G, Ile, K, L, M, R, T, V, Y, N, D, Gln, H, S, or Tφ;

$X_3$ is S, F, A, or Y;

$X_5$ is G, A, or dA; and $X_6$ is T, V, or S.

For example, a sequence of SEQ ID NO: 167 can be $$C^*-X_2-X_3-Y-G-T-C^* \quad \text{(SEQ ID NO: 168)}$$

wherein C*, $X_2$, and $X_3$ are as defined above.

In some embodiments, X is a linear polypeptide comprising (SEQ ID NO: 167).

In some embodiments, X is a linear polypeptide comprising (SEQ ID NO: 168).

In some embodiments, X is a linear polypeptide comprising a sequence having at least 80% sequence identity to a sequence:

$$X_1 X_2-C^*-X_4-X_5-Y-X_7-X_8-C^*-X_{10}-X_{11} \quad \text{(SEQ ID NO: 169)}$$

wherein:

C* is a group of Formula (A) as described above;

$X_1$ is R, D, H, L, or F;

$X_2$ is A, D, G, P, or S;

$X_4$ is A, E, F, G, Ile, K, L, M, R, T, V, Y, N, D, Gln, H, S, or Tφ;

$X_5$ is A, Y, F, or S;

$X_7$ is G, A, or dA;

$X_8$ is T, V, or S;

$X_{10}$ is H, L, or F; and $X_{11}$ is R, D, or H.

In some embodiments, X is a linear polypeptide comprising (SEQ ID NO: 169).

In some embodiments, X is a linear polypeptide comprising a sequence having at least 80% sequence identity to a sequence:

$$C^*-Y-X_3-S-Y-X_6-X_7-X_8-X_9-C^* \quad \text{(SEQ ID NO: 170)}$$

wherein:

C* is a group of Formula (A) as described above;

$X_3$ is N or D;

$X_6$ is G or Y;

$X_7$ is H or V;

$X_8$ is P or Tφ; and and $X_9$ is Tφ or Y.

In some embodiments, X is a linear polypeptide comprising (SEQ ID NO: 170).

In some embodiments, X is a linear polypeptide comprising a sequence having at least 80% sequence identity to a sequence:

$$X_1-X_2-X_3-C^*-Y-X_6-S-Y-X_9-X_{10}-X_{11}-X_{12}-C^*-X_{14}-X_{15}-X_{16} \quad \text{(SEQ ID NO: 171)}$$

Wherein:

$X_1$ is N or R;

$X_2$ is H or F;

$X_3$ is G or L;

C* is a group of Formula (A) as described above;

$X_6$ is N or D;

$X_9$ is G or Y;

$X_{10}$ is V or H;

$X_{11}$ is P or Tφ;

$X_{12}$ is Y or Tφ;

$X_{14}$ is D or S;

$X_{15}$ is Y or H;

and $X_{16}$ is S or H.

In some embodiments, X is a linear polypeptide comprising (SEQ ID NO: 171).

In some embodiments, X is a linear polypeptide comprising a sequence having at least 80% sequence identity to a sequence:

$$X_1-X_2-C^*-P-Y-X_6-L-C^*-X_9-X_{10}-X_{11} \quad \text{(SEQ ID NO: 172)}$$

wherein $X_1$ is Tφ, F, H, or Y;

$X_2$ is H, D, or E;

C* is a group of Formula (A) as described above;

$X_6$ is D, G, or A;

$X_9$ is H, F, Y, or Tφ;

$X_{10}$ is Ile, L, or V; and $X_{11}$ is N, Gln, He, L, or V.

In some embodiments, X is a linear polypeptide comprising (SEQ ID NO: 172).

In some embodiments, X is a linear polypeptide comprising a sequence having at least 80% sequence identity to a sequence selected from the group consisting of:

$$R-S-C^*-N-Y-Y-G-T-C^*-L-H \quad \text{(SEQ ID NO: 173)}$$

$$H-D-C^*-Q-Y-Y-G-T-C^*-L-H \quad \text{(SEQ ID NO: 174)}$$

$$F-A-C^*-H-Y-Y-G-T-C^*-L-H \quad \text{(SEQ ID NO: 175)}$$

$$R-P-C^*-D-Y-Y-G-T-C^*-F-D \quad \text{(SEQ ID NO: 176)}$$

$$L-P-C^*-D-Y-Y-G-T-C^*-L-D \quad \text{(SEQ ID NO: 177)}$$

$$F-S-C^*-Tφ-Y-S-L-H-C^*-H-R \quad \text{(SEQ ID NO: 178)}$$

$$D-P-C^*-S-Y-Y-G-T-C^*-L-H \quad \text{(SEQ ID NO: 179)}$$

$$L-P-C^*-S-Y-Y-G-T-C^*-L-H \quad \text{(SEQ ID NO: 180)}$$

$$L-S-C^*-D-Y-Y-G-T-C^*-L-R \quad \text{(SEQ ID NO: 181)}$$

$$L-A-C^*-H-Y-Y-G-T-C^*-L-H \quad \text{(SEQ ID NO: 182)}$$

$$D-G-C^*-H-Y-Y-G-T-C^*-L-H \quad \text{(SEQ ID NO: 183)}$$

$$R-P-C^*-N-Y-Y-G-T-C^*-L-H \quad \text{(SEQ ID NO: 184)}$$

$$N-H-G-C^*-Y-N-S-Y-G-V-P-Y-C^*-D-Y-S \quad \text{(SEQ ID NO: 185)}$$

-continued

R-F-L-C*-Y-D-S-Y-Y-H-Tφ-Tφ-C*-S-H-H (SEQ ID NO: 186)

Tφ-F-H-C*-P-Y-D-L-C*-H-I-L (SEQ ID NO: 187)

Q-W-E-C*-P-Y-G-L-C*-Tφ-I-Q (SEQ ID NO: 188)

G-F-H-C*-P-Y-D-L-C*-H-I-L (SEQ ID NO: 189)

F-H-C*-P-Y-D-L-C*-H-I-L (SEQ ID NO: 190)

H-C*-P-Y-D-L-C*-H-I-L (SEQ ID NO: 191)

F-H-C*-P-Y-D-L-C*-H-I (SEQ ID NO: 192)

Tφ-E-C*-P-Y-G-L-C*-Tφ-I-Q (SEQ ID NO: 193)

E-C*-P-Y-G-L-C*-Tφ-I-Q (SEQ ID NO: 194)

Tφ-E-C*-P-Y-G-L-C*-Tφ-I (SEQ ID NO: 195)

P-C*-D-Y-Y-G-T-C*-L (SEQ ID NO: 196)

C*-D-Y-Y-G-T-C*-L (SEQ ID NO: 197)

C*-D-Y-Y-G-T-C* (SEQ ID NO: 198)

L-P-C*-D-Y-Y-D-A-T-C*-L-D (SEQ ID NO: 199)

L-A-C*-D-Y-Y-G-T-C*-L-D (SEQ ID NO: 200)

L-P-C*-A-Y-Y-G-T-C*-L-D (SEQ ID NO: 201)

L-P-C*-D-A-Y-G-T-C*-L-D (SEQ ID NO: 202)

L-P-C*-D-Y-A-G-T-C*-L-D (SEQ ID NO: 203)

L-P-C*-D-Y-Y-A-T-C*-L-D (SEQ ID NO: 204)

L-P-C*-D-Y-Y-G-A-C*-L-D (SEQ ID NO: 205)

L-P-C*-D-Y-Y-G-T-C*-A-D (SEQ ID NO: 206)

L-P-C*-D-Y-Y-G-S-C*-L-D (SEQ ID NO: 207)

L-P-C*-D-Y-Y-G-V-C*-A-D (SEQ ID NO: 208)

G-F-H-C*-P-Y-D-L-C*-H-I-L (SEQ ID NO: 209)

F-H-C*-P-Y-D-L-C*-H-I-L (SEQ ID NO: 210)

H-C*-P-Y-D-L-C*-H-I-L (SEQ ID NO: 211)

F-H-C*-P-Y-D-L-C*-H-I (SEQ ID NO: 212)

W-E-C*-P-Y-G-L-C*-Tφ-I-Q (SEQ ID NO: 213)

E-C*-P-Y-G-L-C*-Tφ-I-Q (SEQ ID NO: 214)

and

W-E-C*-P-Y-G-L-C*-Tφ-I; (SEQ ID NO: 215)

wherein C* is a group of Formula (A) as described above. In some embodiments, X is a linear polypeptide comprising a sequence selected from the group consisting of:

R-S-C*-N-Y-Y-G-T-C*-L-H (SEQ ID NO: 173)

H-D-C*-Q-Y-Y-G-T-C*-L-H (SEQ ID NO: 174)

F-A-C*-H-Y-Y-G-T-C*-L-H (SEQ ID NO: 175)

R-P-C*-D-Y-Y-G-T-C*-F-D (SEQ ID NO: 176)

L-P-C*-D-Y-Y-G-T-C*-L-D (SEQ ID NO: 177)

F-S-C*-Tφ-Y-S-L-H-C*-H-R (SEQ ID NO: 178)

D-P-C*-S-Y-Y-G-T-C*-L-H (SEQ ID NO: 179)

L-P-C*-S-Y-Y-G-T-C*-L-H (SEQ ID NO: 180)

L-S-C*-D-Y-Y-G-T-C*-L-R (SEQ ID NO: 181)

L-A-C*-H-Y-Y-G-T-C*-L-H (SEQ ID NO: 182)

D-G-C*-H-Y-Y-G-T-C*-L-H (SEQ ID NO: 183)

R-P-C*-N-Y-Y-G-T-C*-L-H (SEQ ID NO: 184)

N-H-G-C*-Y-N-S-Y-G-V-P-Y-C*-D-Y-S (SEQ ID NO: 185)

R-F-L-C*-Y-D-S-Y-Y-H-Tφ-Tφ-C*-S-H-H (SEQ ID NO: 186)

Tφ-F-H-C*-P-Y-D-L-C*-H-I-L (SEQ ID NO: 187)

Q-W-E-C*-P-Y-G-L-C*-Tφ-I-Q (SEQ ID NO: 188)

G-F-H-C*-P-Y-D-L-C*-H-I-L (SEQ ID NO: 189)

F-H-C*-P-Y-D-L-C*-H-I-L (SEQ ID NO: 190)

H-C*-P-Y-D-L-C*-H-I-L (SEQ ID NO: 191)

F-H-C*-P-Y-D-L-C*-H-I (SEQ ID NO: 192)

Tφ-E-C*-P-Y-G-L-C*-Tφ-I-Q (SEQ ID NO: 193)

E-C*-P-Y-G-L-C*-Tφ-I-Q (SEQ ID NO: 194)

```
Tφ-E-C*-P-Y-G-L-C*-Tφ-I                    (SEQ ID NO: 195)

P-C*-D-Y-Y-G-T-C*-L                        (SEQ ID NO: 196)

C*-D-Y-Y-G-T-C*-L                          (SEQ ID NO: 197)

C*-D-Y-Y-G-T-C*                            (SEQ ID NO: 198)

L-P-C*-D-Y-Y-D-A-T-C*-L-D                  (SEQ ID NO: 199)

L-A-C*-D-Y-Y-G-T-C*-L-D                    (SEQ ID NO: 200)

L-P-C*-A-Y-Y-G-T-C*-L-D                    (SEQ ID NO: 201)

L-P-C*-D-A-Y-G-T-C*-L-D                    (SEQ ID NO: 202)

L-P-C*-D-Y-A-G-T-C*-L-D                    (SEQ ID NO: 203)

L-P-C*-D-Y-Y-A-T-C*-L-D                    (SEQ ID NO: 204)

L-P-C*-D-Y-Y-G-A-C*-L-D                    (SEQ ID NO: 205)

L-P-C*-D-Y-Y-G-T-C*-A-D                    (SEQ ID NO: 206)

L-P-C*-D-Y-Y-G-S-C*-L-D                    (SEQ ID NO: 207)

L-P-C*-D-Y-Y-G-V-C*-A-D                    (SEQ ID NO: 208)

G-F-H-C*-P-Y-D-L-C*-H-I-L                  (SEQ ID NO: 209)

F-H-C*-P-Y-D-L-C*-H-I-L                    (SEQ ID NO: 210)

H-C*-P-Y-D-L-C*-H-I-L                      (SEQ ID NO: 211)

F-H-C*-P-Y-D-L-C*-H-I                      (SEQ ID NO: 212)

W-E-C*-P-Y-G-L-C*-Tφ-I-Q                   (SEQ ID NO: 213)

E-C*-P-Y-G-L-C*-Tφ-I-Q
and                                        (SEQ ID NO: 214)

W-E-C*-P-Y-G-L-C*-Tφ-I;                    (SEQ ID NO: 215)
``` wherein C* is a group of Formula (A) as described above.

In some embodiments, X is a linear polypeptide comprising a sequence having at least 80% sequence identity to a sequence selected from the group consisting of:

```
F-H-C*-P(4-OH)-Y(3-Cl)-D-L-C*-H-I-Q        (SEQ ID NO: 216)

Y-D-E-C*-P(4-OH)-Y(3-Cl)-G-L-C*-Y-I-Q      (SEQ ID NO: 217)

Q-W-E-C*-P-Y-G-L-C*-W-I-Q,                 (SEQ ID NO: 218)
``` wherein C* is a group of Formula (A), as defined above.

In some embodiments, X is a linear polypeptide comprising a sequence selected from the group consisting of:

```
F-H-C*-P(4-OH)-Y(3-Cl)-D-L-C*-H-I-Q        (SEQ ID NO: 216)

Y-D-E-C*-P(4-OH)-Y(3-Cl)-G-L-C*-Y-I-Q      (SEQ ID NO: 217)

Q-W-E-C*-P-Y-G-L-C*-W-I-Q,                 (SEQ ID NO: 218)
``` wherein C* is a group of Formula (A), as defined above.

As used herein, the expression "having at least 80% sequence identity" refers to a polypeptide having a sequence identity of from at least about 80% to at least about 99% compared to a reference sequence. For example, a sequence having at least 80% sequence identity may have at least about 80%, at least about 85%, at least about 90%, at least about 91%, at least about 92%, at least about 93%, at least about 94%, at least about 95%, at least about 96%, at least about 97%, at least about 98%, or at least about 99% sequence identity compared to a reference sequence.

As used herein, the term "polypeptide", used alone or in combination with other terms, refers to a compound of two or more natural or non-natural amino acids bonded through the main chain by a peptide amide bond (e.g., —C(=O)NH—).

In some embodiments, the polypeptides provided herein are between 6 to 75 amino acids in length (e.g., 3 to 50, 1 to 50, 10 to 50, 10 to 30, 3 to 30, 3 to 20, 3 to 15, 5 to 30, 3 to 25, 16 to 17, 5 to 25, 5 to 20, 5 to 15, 11 to 25, 11 to 50, 11 to 40, 10 to 12, 8 to 30, 8 to 20, or 8 to 15 amino acids in length). For example, the polypeptides can be between 10 to 25 amino acids in length, between 10 to 24 amino acids in length, between 10 to 23 amino acids in length, between 10 to 22 amino acids in length, between 10 to 21 amino acids in length, between 10 to 20 amino acids in length, between 10 to 19 amino acids in length, between 10 to 18 amino acids in length, between 10 to 17 amino acids in length, between 10 to 16 amino acids in length, between 10 to 15 amino acids in length, between 10 to 14 amino acids in length, between 10 to 13 amino acids in length, between 10 to 12 amino acids in length, or between 10 to 11 amino acids in length. In some embodiments, the polypeptides are 10 amino acids in length. In some embodiments, the polypeptides are 11 amino acids in length. In some embodiments, the polypeptides are 12 amino acids in length. In some embodiments, the polypeptides are 13 amino acids in length. In some embodiments, the polypeptides are 14 amino acids in length. In some embodiments, the polypeptides are 15 amino acids in length. In some embodiments, the polypeptides are 16 amino acids in length. In some embodiments, the polypeptides are 17 amino acids in length. In some embodiments, the polypeptides are 18 amino acids in length. In some embodiments, the polypeptides are 19 amino acids in length. In some embodiments, the polypeptides are 20 amino acids in length. In some embodiments, the polypeptides are 21 amino acids in length. In some embodiments, the polypeptides are 22 amino acids in length. In some embodiments, the polypeptides are 23 amino acids in length. In some embodiments, the polypeptides are 24 amino acids in length. In some embodiments, the polypeptides are 25 amino acids in length.

As used herein, the term "natural" or "naturally occurring" amino acid refers to one of the twenty most common occurring amino acids. Natural amino acids modified to provide a label for detection purposes (e.g., radioactive labels, optical labels, or dyes) are considered to be natural amino acids. Natural amino acids are referred to by their standard one- or three-letter abbreviations.

The term "non-natural amino acid" or "non-natural" refers to any derivative of a natural amino acid including D forms, and β and γ amino acid derivatives. It is noted that certain amino acids, e.g., hydroxyproline, that are classified as a non-natural amino acid herein, may be found in nature within a certain organism or a particular protein. Non-limiting examples of non-natural amino acids include those described in WO 2008/071679 (see, e.g., Table 3); WO 2001/009188; and U.S. Pat. No. 6,991,775 (see, e.g., FIG. 1).

The term "binding to fibrin", used along or together with other terms, refers to a moiety capable of forming a complex with a clot, soluble or insoluble fibrin, or a soluble or insoluble fragment of fibrin (e.g., fibrin-derived polypeptides) having a structure or characteristic exhibited by fibrin but not fibrinogen.

The term "binding" refers to the determination by standard assays, including those described herein, that a binding moiety recognizes and binds reversibly to a given target. Such standard assays include equilibrium dialysis, gel filtration, and the monitoring of spectroscopic changes that result from binding.

The term "detectable agent" refers a functional group that physically or chemically interacts with its environment to produce a signal or product that can be detected by analytical and/or imaging methods. Example methods include, but are not limited to, visible, UV-, IR-, NIR-light, X-Ray, MR, and NMR-based imaging methods, enzymatic assays, and UV-, IR-, NMR-, X-ray-, and mass spectrometry-based analytics.

In some embodiments, each detectable agent independently comprises one or more groups independently selected from organic small molecules, inorganic compounds, nanoparticles, enzymes or enzyme substrates, fluorescent materials, luminescent materials, bioluminescent materials, chemiluminescent materials, magnetic materials, radioactive isotopes, and contrast agents.

Examples of suitable enzymes include, but are not limited to, horseradish peroxidase, alkaline phosphatase, beta-galactosidase, or acetylcholinesterase.

Examples of suitable fluorescent materials include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMIA (5-Carboxytetranethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO -TAGTM CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy F1-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C -phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrohodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor -Ruby; FluorX; FM 1-43™; FM 4-46; Fura Red™; Fura Red™/Fluo-3; Fura-2; Fura -2/BCECF; Genacryl Brilliant Red B; Genacryl Brilliant Yellow 1OGF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, WV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo -1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™488; Oregon Green™500; Oregon Green™514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); Tetramethyl-RodamineIsoThioCyanate (TRITC); True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. An example of a luminescent material includes luminol; Examples of bioluminescent materials include, but are not limited to, luciferase, luciferin, and aequorin.

As used herein the term "radioactive isotope" or "radioisotope" refers to one or more atoms having an atomic mass or mass number different from the atomic mass or mass number typically found in nature (i.e., naturally occurring). It is understood that a "radio-labeled" or "labeled compound" is a compound that has incorporated at least one radioisotope.

As used herein, the term "Ci", used alone or in combination with other terms, refers to "Curie", which is a unit of radioactivity.

Examples of suitable radioisotopes include, but are not limited to, $^{11}C$, $^{14}C$, $^{13}N$, $^{15}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, $^{131}I$, $^{99m}Tc$, $^{51}Cr$, $Al^{-18}F$, $^{67}Ga$, $^{68}Ga$, $^{44}Sc$, $^{47}Sc$, $^{167}Tm$, $^{141}Ce$, $^{111}In$, $^{113}In$, $^{168}Yb$, $^{175}Yb$, $^{140}La$, $^{90}Y$, $^{86}Y$, $^{153}Sm$, $^{166}Ho$, $^{165}Dy$, $^{166}Dy$, $^{61}Cu$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$, $^{111}Ag$, $^{199}Au$, $^{51}Mn$, $^{52m}Mn$, $^{52g}Mn$, $^{52}Fe$, $^{60}Cu$, $^{72}As$, $^{94m}Tc$, $^{110}In$, $^{142}Pr$, $^{153}Gd$, $^{159}Gd$, or other radioisotopes detectable by direct counting of radio emission or by scintillation counting.

Example contrast agents include, but are not limited to, gold (e.g., gold nanoparticles), gadolinium (e.g., chelated Gd), iron oxides (e.g., superparamagnetic iron oxide (SPIO), monocrystalline iron oxide nanoparticles (MIONs), ultrasmall superparamagnetic iron oxide (USPIO)), manganese chelates (e.g., Mn-DPDP), barium sulfate, iodinated contrast media (iohexol), microbubbles, and perfluorocarbons. Contrast agents may be used, for example, as contrast agents for MRI or NMR (e.g., PET or SPECT), for X-ray CT, Raman imaging, optical coherence tomography, absorption imaging, ultrasound imaging, or thermal imaging.

In some embodiments, each detectable agent independently comprises one or more groups independently selected from the group consisting of a radioactive isotope, a fluorescent material, a contrast agent, a luminescent material, and bioluminescent material. In some embodiments, each detectable agent independently comprises one or more groups independently selected from the group consisting of a radioactive isotope, a fluorescent material, a contrast agent, or a mixture thereof. In some embodiments, each detectable agent independently comprises one or more groups independently selected from the group consisting of a radioactive isotope, a fluorescent material, and a contrast agent. In some embodiments, each detectable agent comprises a radioactive isotope. In some embodiments, each radioactive isotope is independently selected from the group consisting of $Al^{-18}F$, $^{64}Cu$, $^{99m}Tc$, $^{68}Ga$, and $^{111}In$. In some embodiments, each radioactive isotope is $Al^{-18}F$. In some embodiments, each radioactive isotope is $^{64}Cu$. In some embodiments, each radioactive isotope is $^{99m}Tc$. In some embodiments, each radioactive isotope is $^{68}Ga$. In some embodiments, each radioactive isotope is $^{111}In$. In some embodiments, each detectable agent comprises a contrast agent. In some embodiments, the contrast agent comprises $Gd^{3+}$. In some embodiments, each detectable agent comprises a fluorescent material. In some embodiments, each fluorescent material is independently selected from the group consisting of boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene -2-propionyl)amino)hexanoic acid, Oregon Green 88, 6-(((4,4-difluoro-5-(2-pyrrolyl)-4 -bora-3a,4a-diaza-s-indacene-3-yl)styryloxy)acetyl)aminohexanoic acid, 7-N,N -diethylaminocoumarin, sulforhodamine 101, VIVOTAG 680 (an amine-reactive near -infra-red fluorochrome, from VisEn Medical), umbelliferone, fluorescein, rhodamine, tetramethylrhodamine, dichlorotriazinylamine fluorescein, dansyl, and phycoerythrin. In some embodiments, each fluorescent material is tetramethylrhodamine.

In some embodiments, each detectable agent further comprises a chelating group. Example chelating agents include, but are not limited to, acids with methylene phosphonic acid groups, methylene carbohydroxamine acid groups, carboxyethylidene groups, carboxymethylene groups, diethylenetriaminepentaacetic acid (DTPA); 1,4,7,10-tetraazacyclotetradecane-1,4,7,10-tetraacetic acid (DOTA); ethylenediaminetetraacetic acid (EDTA); 1,4,8,11-tetraazacyclotetradecane-1,4,8,11-tetraacetic acid (TETA); ethylenebis-(Z-hydroxyphenylglycine) (EHPG) and derivatives thereof including 5-CI -EHPG, 5Br-EHPG, 5-Me-EHPG, 5t-Bu-EHPG, and 5sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-Z (hydroxybenzyl)-ethylene-diaminediacetic acid (HBED) and derivatives thereof; benzo-DOTA, dibenzo-DOTA, and benzo-NOTA, where NOTA is 1,4,7 -triazacyclononane; N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA); triethylenetetraaminehexaacetic acid (TTHA); derivatives of 1,5,10-N,N',N"-tris(Z,3-dihydroxybenzoyl)-tricatecholate (UCAM) and 1,3,5-N,N',N"-tris(Z,3-dihydroxybenzoyl)aminomethylbenzene (MECAM). Additional chelating agents may be found in WO 2008/071679, WO 01/09188, WO 98/18496, WO 86/06605, WO 91/03200, WO 95/28179, WO 96/23526, WO 97/36619, PCT/US98/01473, PCT/US98/20182, and U.S. Pat. No. 4,899,755.

In some embodiments, each detectable agent further comprises a chelating group independently selected from the group consisting of CB-TE2A, CB-TE1A1P, DiAmSar, DTPA, DOTA, DOTAGA, DOTMA, EDTA, EHPG, HBED, LICAM, MECAM, NOTA, NODAGA, PCTA, PDTA, TETA, TETMA, TTHA, CDTA, HBET, and CP256. In some embodiments, each detectable agent further comprises a chelating group independently selected from the group consisting of NODAGA and DOTAGA. In some embodiments, each $D^1$ and $D^2$ are each independently selected from the group consisting of:

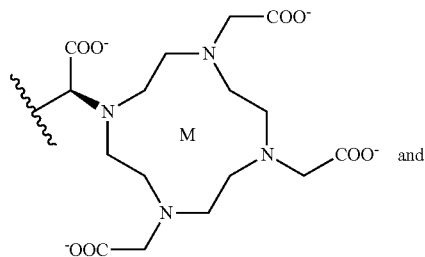

wherein each M is independently selected from Gd, $^{64}$Cu, and $^{68}$Ga. In some embodiments, $D^1$ is

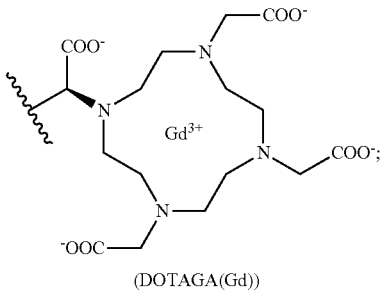

(DOTAGA(Gd))

$D^2$ is

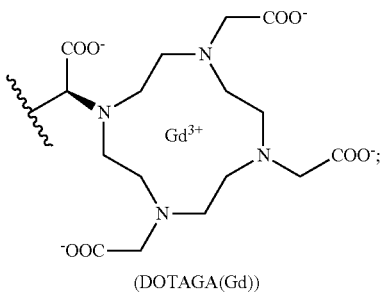

(DOTAGA(Gd))

(DOTAGA(Gd)); a is 2; and d is 2. In some embodiments, $D^1$ is $^{68}$Ga-NODAGA; $D^2$ is $^{68}$Ga-NODAGA; a is 1; and d is 1. In some embodiments, $D^1$ is $^{64}$Cu-NODAGA; $D^2$ is $^{64}$Cu-NODAGA; a is 1; and d is 1.

In some embodiments, $L^1$ is selected from the group consisting of $C_{1-6}$ alkylene, $C_{2-6}$ alkenylene, $C_{2-6}$ alkynylene, $C_{1-6}$ haloalkylene, $C(=O)R^{a2}$, $C(=O)OR^{b2}$, $C(=O)NR^{c2}R^{d2}$, $NR^{c2}C(=O)R^{a2}$, $NR^{c2}C(=O)OR^{b2}$, $NR^{c2}C(=O)NR^{c2}R^{d2}$, $S(O)R^{e2}$, $S(O)_2R^{e2}$, $NR^{c2}S(O)R^{e2}$, $NR^{c2}S(O)_2R^{e2}$, $NR^{c2}S(=O)NR^{c2}R^{d2}$, and $NR^{c2}S(=O)_2NR^{c2}R^{d2}$, wherein each $R^{a2}$, $R^{b2}$, $R^{c2}$, $R^{d2}$, and $R^{e2}$ is independently selected from H, $C_{1-6}$ alkylene, $C_{1-6}$ haloalkylene, $C_{2-6}$ alkenylene, and $C_{2-6}$ alkynylene.

In some embodiments, $L^2$ is selected from the group consisting of $C_{1-6}$ alkylene, $C_{2-6}$ alkenylene, $C_{2-6}$ alkynylene, $C_{1-6}$ haloalkylene, $C(=O)R^{a2}$, $C(=O)OR^{b2}$, $C(=O)NR^{c2}R^{d2}$, $NR^{c2}C(=O)R^{a2}$, $NR^{c2}C(=O)OR^{b2}$, $NR^{c2}C(=O)NR^{c2}R^{d2}$, $S(O)R^{e2}$, $S(O)_2R^{e2}$, $NR^{c2}S(O)R^{e2}$, $NR^{c2}S(O)_2R^{e2}$, $NR^{c2}S(=O)NR^{c2}R^{d2}$, and $NR^{c2}S(=O)_2NR^{c2}R^{d2}$, wherein each $R^{a2}$, $R^{b2}$, $R^{c2}$, $R^{d2}$, and $R^{e2}$ is independently selected from H, $C_{1-6}$ alkylene, $C_{1-6}$ haloalkylene, $C_{2-6}$ alkenylene, and $C_{2-6}$ alkynylene.

In some embodiments, $L^1$ and $L^2$ are each $C(O)R^{a2}$, wherein each $R^{a2}$ is independently selected from the group consisting of $C_{1-6}$ alkylene, $C_{1-6}$ haloalkylene, $C_{2-6}$ alkenylene, and $C_{2-6}$ alkynylene. In some embodiments, $L^1$ and $L^2$ are each $C(O)R^{a2}$, wherein each $R^{a2}$ is $C_{1-6}$ alkylene. In some embodiments, $L^1$ and $L^2$ are each $—C(O)CH_2CH_2—$.

In some embodiments, the compound of Formula (I) is a compound of Formula

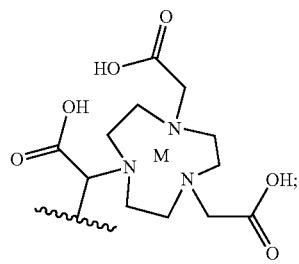

(Ia):

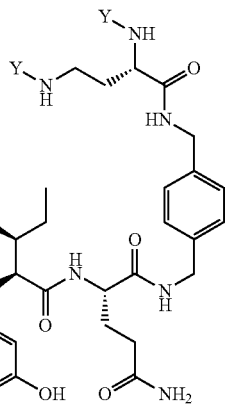
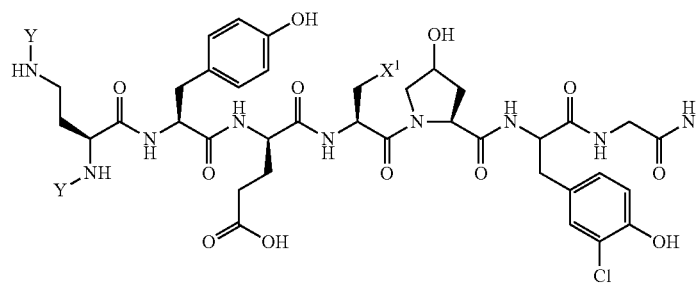

wherein each of $X^1$ and $X^2$ is —S—S—CH$_2$CH$_2$—NH$_2$; and
each Y is

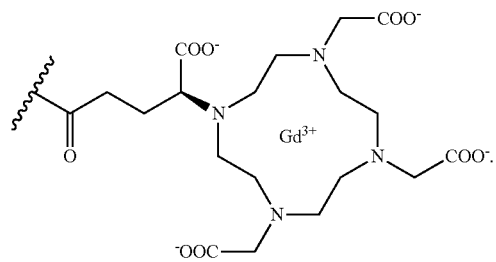

In some embodiments, the compound of Formula (I) is a compound of Formula (Ib):

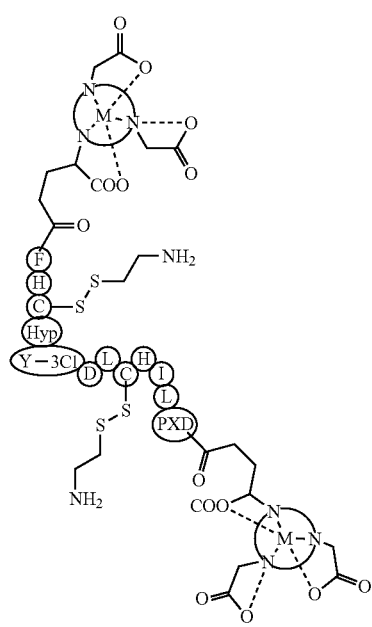

wherein each M is independently selected from $^{64}$Cu and $^{68}$Ga. In some embodiments, each M is $^{64}$Cu. In some embodiments, each M is $^{68}$Ga.

The present application further provides, inter alia, compounds of Formula (II):

$$(D^1)_a—(L^1)_b—X^A—(L^2)_c—(D^2)_d \qquad (II)$$

or a pharmaceutically acceptable salt thereof wherein $X^A$ is a cyclic polypeptide comprising a disulfide bridge and is capable of binding to fibrin; and variables $D^1$, $D^2$, $L^1$, $L^2$, a, b, c, and d are defined according to the definitions described herein for compounds of Formula (I).

In some embodiments, cyclic polypeptide $X^A$ is a cyclized form of linear polypeptide X, which is defined according to the definitions described herein for compounds of Formula (I). In some embodiments, $X^A$ is cyclized through the formation of a disulfide bond between at least two of the at least two disulfide moieties of X. In some embodiments, $X^A$ is cyclized though the formation of a disulfide between at least two of the C* residues. In some embodiments, the compound of Formula (II) is a reaction product of the reaction between a compound of Formula (I) and protein disulfide isomerase.

In some embodiments, the compound of Formula (II) is a compound of Formula (IIa)

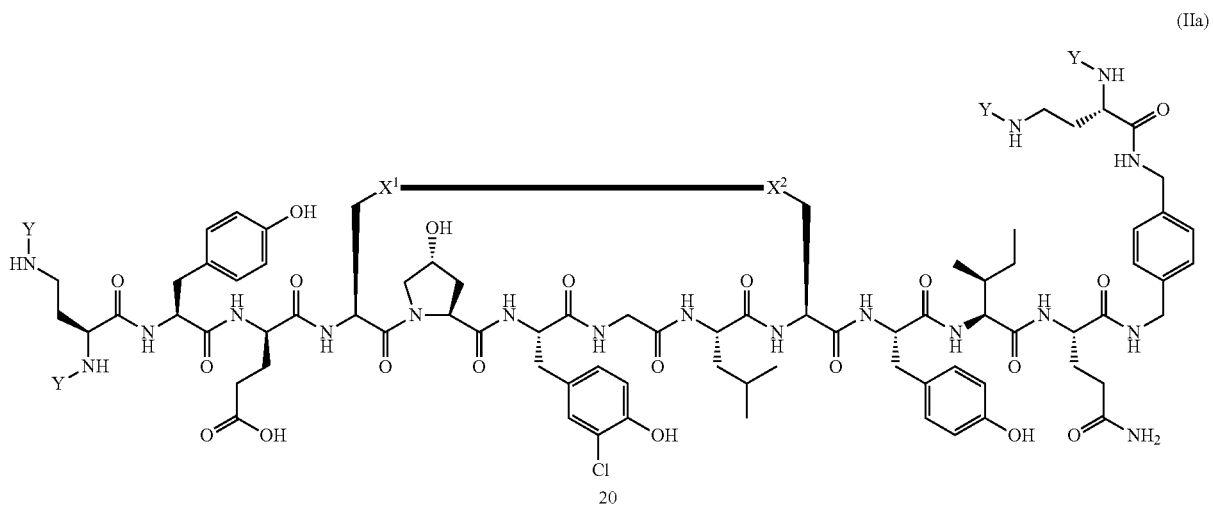

wherein:
$X^1$ is S;
$X^2$ is S; and
each Y is

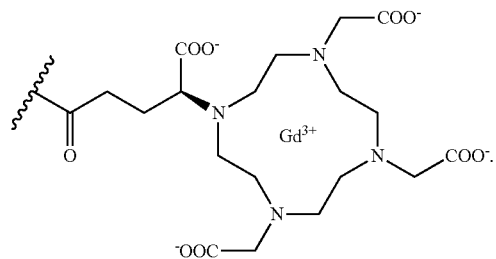

In some embodiments, the compound of Formula (IIa) is a reaction product of a reaction between a compound of Formula (Ia) and protein disulfide isomerase.

In some embodiments, the compound of Formula (II) is a compound of Formula (IIb):

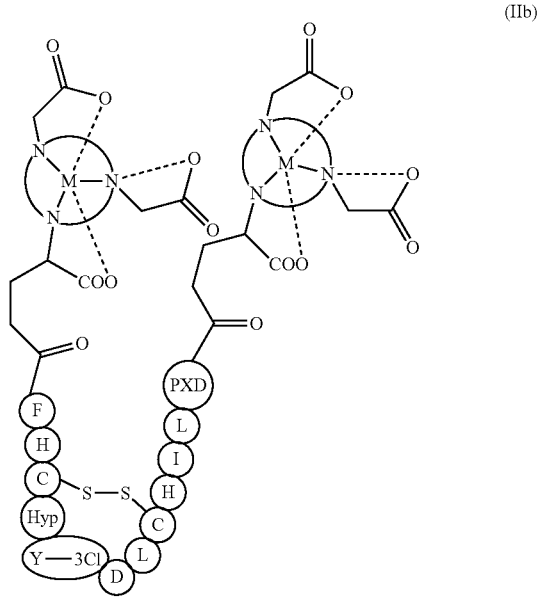

wherein each M is independently selected from $^{64}Cu$ and $^{68}Ga$. In some embodiments, each M is $^{64}Cu$. In some embodiments, each M is $^{68}Ga$. In some embodiments, the compound of Formula (IIb) is a reaction product of a reaction between a compound of Formula (Ib) and protein disulfide isomerase.

Additional non-limiting examples of compounds of Formula (II) can be found in WO 2008/071679; WO 2001/009188; U.S. Pat. No. 6,991,775; U.S. Pat. No. 7,238,341; Starmans, L. W. E. et al., *Contrast Media & Mol. Imaging* (2013), 8: 229-237; Boros, E. et al., *Molecular Pharmaceutics* (2014), 11: 617-629; Hara, T. et al., *J. Am. Coll. Cardiol Img.* (2012) 5: 607-615; Ay, I. et al., *Circ. Cardiovasc. Imaging* (2014) 7: 697-705; Sirol, M. et al., *Atherosclerosis* (2005) 182: 79-85; Ciesienski, K. L. et al., *Molecular Pharmaceutics* (2013) 10(3): 1100-1110; and Blasi, F. et al., *J. Nucl. Med.* (2014) 55: 1-7. In some embodiments, the examples provided by the references cited herein can be prepared by reacting a corresponding compound of Formula (I) in the presence of a protein disulfide isomerase.

Synthesis

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999).

At various places in the present specification, divalent linking substituents are described. It is specifically intended that each divalent linking substituent include both the forward and backward forms of the linking substituent. For example, $-NR(CR'R'')_n-$ includes both $-NR(CR'R'')_n-$ and —(CR'R")$_n$NR—. Where the structure clearly requires a linking group, the Markush variables listed for that group are understood to be linking groups.

Direct synthesis of the polypeptides provided herein may be accomplished using conventional techniques, including solid-phase peptide synthesis, solution-phase synthesis, etc. Solid-phase synthesis is preferred. In solid-phase synthesis, for example, a suitably protected amino acid residue is attached through its carboxyl group to a derivatized, insoluble polymeric support, such as cross-linked polystyrene or polyamide resin.

As used herein, the term "suitably protected" refers to the presence of protecting groups on both the a-amino group of the amino acid, and on any side chain functional groups. Side chain protecting groups are generally stable to the solvents, reagents and reaction conditions used throughout the synthesis and are removable under conditions which do not affect the final peptide product. Stepwise synthesis of the polypeptide is carried out by the removal of the N-protecting group from the initial amino acid, and coupling thereto of the carboxyl end of the next amino acid in the sequence of the polypeptide. This amino acid is also suitably protected. The carboxyl of the incoming amino acid can be activated to react with the N-terminus of the bound amino acid by formation into a reactive group such as formation into a carbodiimide, a symmetric acid anhydride or an "active ester" group such as hydroxybenzotriazole or pentafluorophenyl esters. The preferred solid-phase peptide synthesis methods include the BOC method which utilizes tert-butyloxycarbonyl as the a-amino protecting group, and the FMOC method which utilizes 9-fluorenylmethloxycarbonyl to protect the a-amino of the amino acid residues, both methods of which are well-known by those of skill in the art. See, Stewart et al., *Solid-Phase Peptide Synthesis* (1989), W. H. Freeman Co., San Francisco; Merrifield, *J. Am. Chem. Soc.*, 85:2149-2154 (1963); Bodanszky and Bodanszky, *The Practice of Peptide Synthesis* (Springer-Verlag, New York 1984).

Also provided are isolated or purified polypeptide sequences that have at least 85% sequence identity (e.g., at least 90%, 95%, or 99% sequence identity) to one of the specific sequences disclosed herein. In calculating percent sequence identity, two sequences are aligned and the number of identical matches of amino acid residues between the two sequences is determined. The number of identical matches is divided by the length of the aligned region (i.e., the number of aligned amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer. The alignment of two or more sequences to determine percent sequence identity is performed using the algorithm described by Altschul et al. (1997, *Nucleic Acids Res.*, 25:3389-3402) as incorporated into BLAST (basic local alignment search tool) programs, available at ncbi.nlm.nih.gov on the World Wide Web). BLAST searches can be performed to determine percent sequence identity between a sequence having the activity described herein (e.g., fibrin binding) and any other sequence or portion thereof aligned using the Altschul et al. algorithm. BLASTP is the program used to align and compare the identity between amino acid sequences. When utilizing BLAST programs to calculate the percent identity between a sequence of the invention and another sequence, the default parameters of the respective programs are used.

Polypeptides provided herein also may be produced using recombinant DNA techniques, utilizing nucleic acids (polynucleotides) encoding the polypeptides provided herein and then expressing them recombinantly, i.e., by manipulating host cells by introduction of exogenous nucleic acid molecules in known ways to cause such host cells to produce the desired fibrin binding polypeptides. Recombinant production of short peptides such as those described herein may not be practical in comparison to direct synthesis, however recombinant means of production may be advantageous where a fibrin binding motif provided herein is desired to be incorporated in a hybrid polypeptide or fusion protein.

In some embodiments, the polypeptides provided herein are provided in an isolated form. In some embodiments, the polypeptides are purified to homogeneity. As used herein, the term "homogeneity" is considered to be a preparation which results in at least about 95% of the input material obtained in a single peak on an HPLC column, for example about 95%, about 95.5%, about 96%, about 96.5%, about 97%, about 97.5%, about 98%, about 98.5%, about 99%, or about 99.5%. In some embodiments, at least about 99.5% of the input material is obtained in a single peak on an HPLC column.

As used herein, the term "DD(E)" refers to a fibrin subcomponent typically generated by proteolytic degradation of fibrin with plasmin or trypsin. Specifically, DD(E) refers to a complex of DD with the central E domain of fibrin, and approximately includes includes α(111-197), β(134-461), γ(88-406), α(17-78), β(15-122) and γ(1-62) in the human fibrinogen sequence. The term "DD" refers to the glutaminase crosslinked D domains of adjacent fibrin monomers. It is appreciated that "DD(E)" and "DD" are products of proteolysis of fibrin, therefore their composition may exhibit heterogeneity depending on the mode of protease digestion and subsequent isolation (see Olexa et al., *Biochemistry*, 20: 6139-6145 (1981); Moskowitz and Budzynski, *Biochemistry*, 33: 12937-12944 (1994); Spraggon et al., *Nature*, 389: 455-462 (1997); and references therein).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl;

higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "cyano-$C_{1-3}$ alkyl" refers to a group of formula —($C_{1-3}$ alkylene)—CN.

As used herein, the term "HO-$C_{1-3}$ alkyl" refers to a group of formula —($C_{1-3}$ alkylene)—OH.

As used herein, the term "$C_{1-3}$ alkoxy-$C_{1-3}$ alkyl" refers to a group of formula —($C_{1-3}$ alkylene)—O($C_{1-3}$ alkyl).

As used herein, the term "$C_{1-4}$ alkoxy-$C_{1-4}$ alkyl" refers to a group of formula —($C_{1-4}$ alkylene)—O($C_{1-4}$ alkyl).

As used herein, the term "$C_{1-4}$ haloalkoxy-$C_{1-4}$ alkyl" refers to a group of formula —($C_{1-4}$ alkylene)—O($C_{1-4}$ haloalkyl).

As used herein, the term "carboxy" refers to a group of formula —C(O)OH.

As used herein, the term "di($C_{n-m}$ alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$ alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, the halo group is F or Cl.

As used herein, "Cn-m haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)).

Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is cyclohexyl or adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring -forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membereted heteroaryl ring. A five-membered heteroaryl ring is a heteroaryl with a ring having five ring atoms wherein one or more (e.g., 1, 2, or 3) ring atoms are independently selected from N, O, and S. Exemplary five- membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H -imidazole, 1H-, 2H- and 4H-1,2,4-triazole, 1H- and 2H-isoindole, and 1H- and 2H -pyrazole. Tautomeric forms can be in equilibrium or sterically locked into one form by appropriate substitution.

Unless indicated otherwise, compounds provided herein can also include all isotopes of atoms occurring in the intermediates or final compounds. Isotopes include those atoms having the same atomic number but different mass numbers. For example, isotopes of hydrogen include tritium and deuterium.

All compounds, and pharmaceutically acceptable salts thereof, can be found together with other substances such as water and solvents (e.g. hydrates and solvates) or can be isolated.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977).

Compounds of Formula (I) may be prepared, for example, from the corresponding cyclic dipeptide by reduction of the disulfide bond with any suitable reducing agent.

Non-limiting examples include dithiothreitol (DTT), dithioerythritol (DTE), tris(2-carboxyethyl)phosphine (TCEP), 2-mercaptoethanol (BME), 2-mercaptoethylamine-HCl, and cysteine-HCl. Reduction of thet disulfide bond is followed by conversion to a mixed disulfide in the presence of an amino-alkylene-thiol (e.g., mercaptoethylamine), as illustrated below in Scheme I.

Scheme I
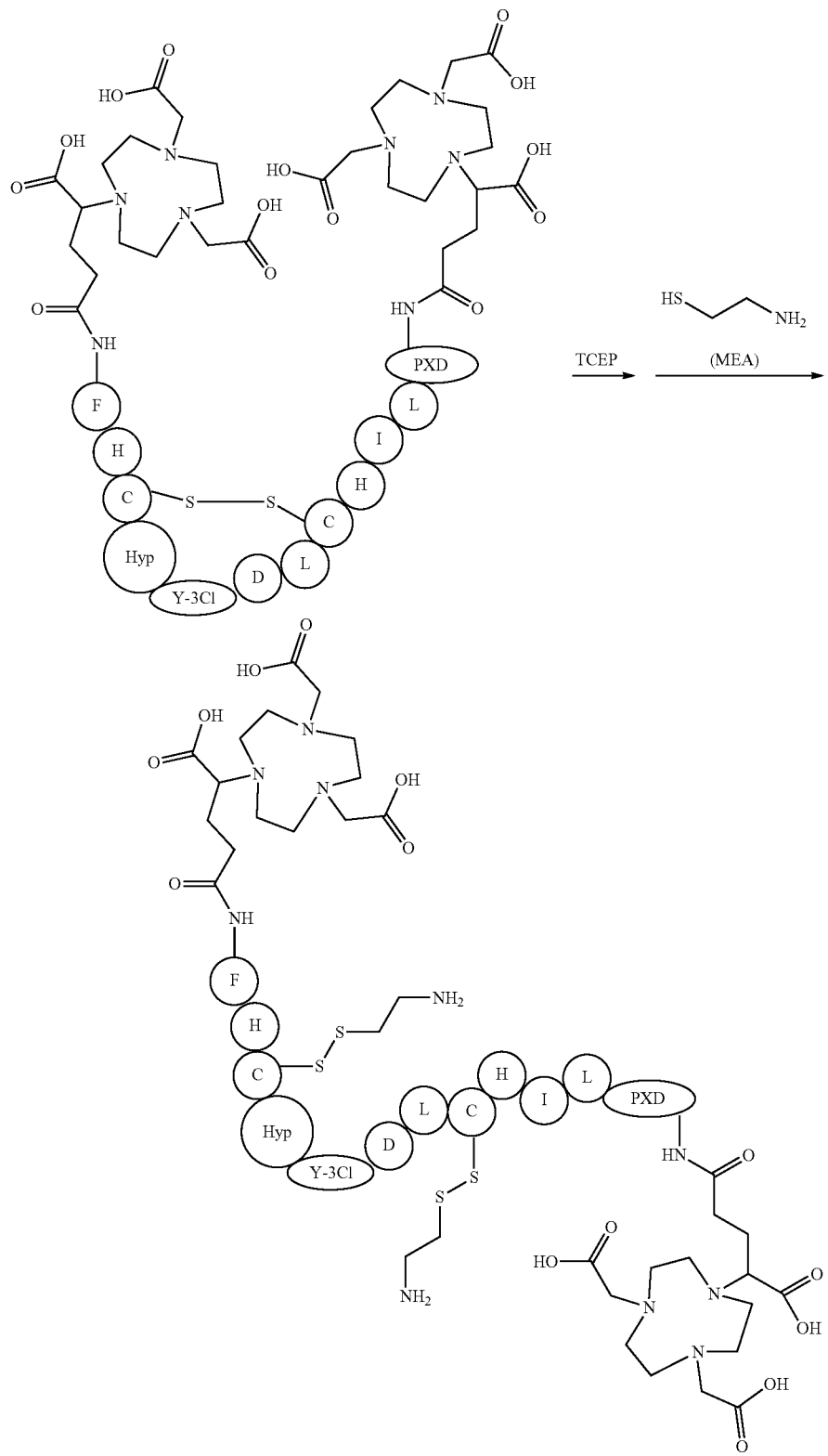
Newly formed thrombi (blood clots) contain activated platelets, which transport the enzyme protein disulfide isomerase (PDI) to the cell surface. In the absence of PDI, the linear compounds of Formula (I) do not bind to fibrin. However, in the presence of PDI an intramolecular cyclization reaction occurs, resulting in new disulfide bridge formation (i.e., formation of a compound of Formula (II)) between the cysteine residues and results in activation of the probe, as shown below in Scheme II.

Scheme II

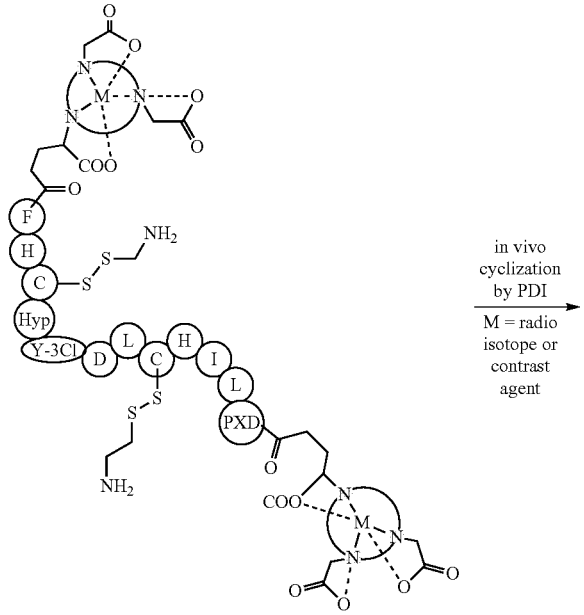

in vivo cyclization by PDI
M = radio isotope or contrast agent

The present application also provides synthetic methods for preparing a compound of Formula (II) from a compound of Formula (I), as shown in Scheme III. In the presence of PDI, a compound of Formula (I) undergoes intramolecular cyclization, resulting in new disulfide bridge formation (i.e., group $X^4$ of Formula (II)).

Scheme III

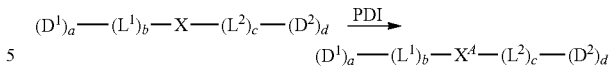

In some embodiments, $X^A$ is a cyclic polypeptide comprising a disulfide bridge. In some embodiments, the compound of Formula (II) is capable of binding to fibrin. In some embodiments, the reaction of a compound of Formula (I) and PDI is an in vivo o intramolecular cyclization reaction.

The present application further provides synthetic methods for incorporating radioisotopes into the compounds provided herein.

Methods

Thrombus Imaging

The compounds provided herein may be used for creating visually readable images of thrombi, to aid in the diagnosis, monitoring and treatment of thrombus associated disorders. The compounds provided herein (e.g., linear polypeptides comprising at least two disulfide moieties) may be converted to probes for detecting thrombi upon cyclization of at least two disulfide moieties. In some embodiments, the binding affinity of the linear polypeptides comprising at least two disulfide moieties is about 25% of the binding affinity for the corresponding cyclized polypeptides, for example, less than about 25%, less than about 20%, less than about 15%, less than about 10%, less than about 5%, less than about 2%, or less than about 1%. In some embodiments, the linear polypeptides comprising at least two disulfide moieties do not bind to fibrin.

In some embodiments, a determination of the affinity of the fibrin binding moiety for fibrin relative to fibrinogen is a useful measure, and is referred to as specificity for fibrin. Standard assays for quantitating binding and determining affinity include equilibrium dialysis, equilibrium binding, gel filtration, or the monitoring of numerous spectroscopic changes (such as fluorescence) that may result from the interaction of the binding moiety and its target. These techniques measure the concentration of bound and free ligand as a function of ligand (or protein) concentration. The concentration of bound polypeptide ([Bound]) is related to the concentration of free polypeptide ([Free]) and the concentration of binding sites for the polypeptide, i.e., on fibrin, (N), as described in the following equation:

[Bound]=N×[Free]/((1/Ka+[Free])).

A solution of the data to this equation yields the association constant, $K_a$, a quantitative measure of the binding affinity. The association constant, $K_a$ is the reciprocal of the dissociation constant, $K_d$. The $K_d$ is more frequently reported in measurements of affinity. A peptide having a $K_d$ 1.5 times higher for fibrinogen than for fibrin would be considered as a weak fibrin binder. A peptide having a $K_d$ 10 times greater for fibrinogen than fibrin would be a moderate fibrin binder, and a peptide having a $K_d$ 100 times or more greater for fibrinogen than for fibrin would be termed highly specific for fibrin. In some embodiments, the polypeptides and detectable agent provided herein have a $K_d$ at least 1.5 times higher for fibrinogen than for fibrin, for example, about 1.5 times higher, at least 2 times higher, at least 5 times higher, at least 10 times higher, at least 20 times higher, at least 40 times higher, at least 60 times higher, at least 80 times higher, at least 100 times higher, at least 250 times higher, at least 500 times higher, at least 750 times higher, or at least 1000 times higher. Preferred fibrin binding polypeptides have a $K_d$ for fibrin in the range of about 1 nanomolar (nM) to about 100 micromolar (µM), for example, at least 10 nM, at least 20 nM, at least 40 nM, at

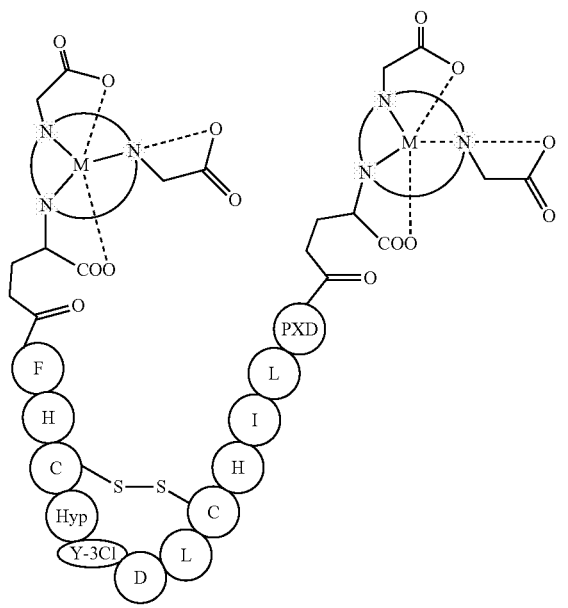

least 60 nM, at least 80 nM, at least 1 µM, at least 5 µM, at least 10 µM, at least 20 µM, at least 40 µM, at least 60 µM, at least 80 µM, at least 90 µM, or at least 100 µM.

The foregoing assay of fibrin affinity can be adapted to a microtiter plate format for evaluating large numbers of polypeptides. Single point concentrations can be used to quickly differentiate molecules of high fibrin specificity or binding affinity from those with low fibrin specificity or binding affinity.

An alternative, empirical approach for measuring fibrin affinity is to form a clot in tubing of a small diameter (e.g., 3 mm), then perfuse the clot with buffer or plasma containing the test polypeptide(s). The concentration of the peptide in the solution as it elutes from the clot is monitored by standard methods (e.g., HPLC separation followed by mass spectrometric detection or fluorescence labeling). Polypeptides that are well retained in the clot are identified as good binders to fibrin clots and as having a useful degree of specificity for fibrin over fibrinogen.

In some embodiments, a peptide exhibiting much greater specificity for fibrin than for fibrinogen is conjugated or linked to a label or detectable agent appropriate for the detection methodology to be employed. For example, the fibrin binder may be conjugated with a contrast agent for magnetic resonance imaging (MRI), with a radioisotope suitable for x-ray imaging, with an ultrasound microsphere or liposome suitable for ultrasound detection, or with an optical imaging dye (e.g., fluorescent material).

When the compound comprising a detectable agent is administered to a patient suspected of having a thrombus, the high affinity of the compound of Formula (I) for fibrin in a thrombus causes the compound to bind to the thrombus and accumulate label at the site of the thrombus. Sufficient time is allowed for the labeled polypeptide to localize at the site of the thrombus. The signal generated by the labeled polypeptide is detected by a scanning device which will vary according to the type of label used, and the signal is then converted to an image of the thrombus.

Accordingly, provided herein are methods for determining the presence or absence of active thrombus formation in a subject, the method comprising:

a) administering to the subject an effective amount of a compound of Formula (I):

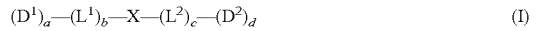

$$(D^1)_a-(L^1)_b-X-(L^2)_c-(D^2)_d \qquad (I)$$

or a pharmaceutically acceptable salt thereof, and b) detecting the reaction product of the compound of Formula (I) and a protein disulfide isomerase, wherein the reaction product is bound to the thrombus if active thrombus formation is present in the subject, wherein variables $D^1$, $D^2$, $L^1$, $L^2$, X, a, b, c, and d are defined according to the definitions described herein for compounds of Formula (I).

Further provided are methods for imaging a thrombus containing activated platelets in a subject, the method comprising:

a) administering to the subject an effective amount of a compound of Formula (I):

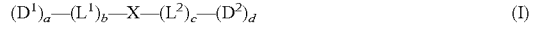

$$(D^1)_a-(L^1)_b-X-(L^2)_c-(D^2)_d \qquad (I)$$

or a pharmaceutically acceptable salt thereof, and b) imaging the reaction product of the compound of Formula (I) and a protein disulfide isomerase, wherein the reaction product is bound to the thrombus, wherein variables $D^1$, $D^2$, $L^1$, $L^2$, X, a, b, c, and d are defined according to the definitions described herein for compounds of Formula (I).

Magnetic Resonance Imaging

The compounds provided herein may be conjugated with a contrast agent as described herein for use in magnetic resonance imaging (MRI). In some embodiments, the compounds provided herein are conjugated with more than one contrast agent. In some embodiments, the contrast agent is chelated to a chelating agent.

The polypeptides provided herein can be bound directly or covalently to a metal chelator (or other detectable agent), or it may be coupled or conjugated to the metal chelator using a linker (e.g., $L^1$ and/or $L^2$ as defined herein). Additional linkers include, but are not limited to disulfide, lactone, imine, phosphoryl, phosphodiester linkages; linear, branched, or cyclic amino acid chains of a single amino acid or different amino acids (e.g., extensions of the N- or C-terminus of polypeptide); derivatized or underivatized polyethylene glycol, polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic, caproic, and pimelic; and other polymeric linkers known in the art (see, e.g., WO 98/18497 and WO 98/118496).

In some embodiments, the linker is a biodegradable linker. As used herein, a "biodegradable linker" is a linker that degrades in vivo to provide efficient routes of excretion for the imaging reagents provided here. Depending on the location within the linker, example biodegradable functionalities include, for example, ester, double ester, amide, phospho ester, ether, acetal, and ketal functionalities.

Optical and Radioisotope Imaging

Various optical parameters may be employed to determine the location of fibrin with in vivo light imaging after injection of the subject with an optically-labeled fibrin binding moiety. Optical parameters to be detected in the preparation of an image may include transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650-1000 nm. NIR radiation can penetrate tissue up to several centimeters, permitting the use of the fibrin binding moieties provided herein for optical imaging of fibrin in vivo.

The polypeptides described herein may be conjugated with photolabels, such as optical dyes, including organic chromophores or fluorophores (e.g., fluorescent materials as defined herein), having extensive delocalized ring systems and having absorption or emission maxima in the range of 400-1500 nm. The polypeptide may alternatively be derivatized with a bioluminescent molecule. The preferred range of absorption maxima for photo labels is between 600 and 1000 nm to minimize interference with the signal from hemoglobin. Preferably, photoabsorption labels have large molar absorptivities, e.g. $>10^5$ cm$^{-1}$ M$^{-1}$ while fluorescent optical dyes will have high quantum yields. Additional fluorescent materials may be found in WO 98/18497, WO 98/18496, WO 98/18495, WO 98/18498, WO 98/53857, WO 96/17628, WO 97/18841, WO 96/23524, WO 98/47538, and references cited therein.

After injection of the optically-labeled linear polypeptides, the patient is scanned with one or more light sources (e.g., a laser) in the wavelength range appropriate for the photo label employed in the agent. The light used may be monochromatic or polychromatic and continuous or pulsed. Transmitted, scattered, or reflected light is detected via a photo detector tuned to one or multiple wavelengths to determine the location of fibrin in the subject. Changes in the optical parameter may be monitored over time to detect accumulation of the optically-labeled reagent at the site of the thrombus. Standard image processing and detecting devices may be used in conjunction with the optical imaging reagents provided herein. The fluorescent materials described herein may also be used for acousto-optical or sonoluminescent imaging performed with optically-labeled imaging agents (see, U.S. Pat. No. 5,171,298, WO 98/57666, and references therein).

Additionally, the compounds provided herein may be conjugated with a radioisotope, as defined herein, for use in scintigraphy, SPECT, or positron emission tomography (PET) imaging. In some embodiments, the compounds provided herein are useful for determining the presence or absence of active thrombus formation in a subject using PET imaging.

Pharmaceutical Compositions

When employed as pharmaceuticals, the compounds provided herein can be administered in the form of pharmaceutical compositions. These compositions can be prepared in a manner well known in the pharmaceutical art, and can be administered by a variety of routes.

Administration may be oral or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the amount a composition administered is sufficient to enhance an MR signal at the site of a thrombus by at least 10%, for example, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Also provided are pharmaceutical compositions which contain, as the active ingredient, a compound of Formula (I), or a pharmaceutically acceptable salt thereof, in combination with one or more pharmaceutically acceptable carriers (excipients). In some embodiments, the composition is suitable for intravenous administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, suspensions, emulsions, solutions, syrups, soft and hard gelatin capsules, suppositories, and sterile injectable solutions.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

The amount of compound or composition administered to a patient will vary depending upon what is being administered, the purpose of the administration, such as prophylaxis or therapy, the state of the patient, the manner of administration, and the like. Effective doses will depend on variety of considerations including the judgment of the attending clinician depending upon factors such as the age, weight and general condition of the patient, and the like.

Methods of Treatment and Combination Therapies

Further provided are methods of treating a subject, comprising:

a) administering to the subject an effective amount of a compound of Formula (I) as defined herein;

b) detecting the presence of the reaction product of the compound of Formula (I) and a protein disulfide isomerase, wherein the presence of the reaction product indicates the presence of active thrombus formation in the subject;

c) identifying a subject who has active thrombus formation; and d) selecting for the identified subject a treatment comprising an anti- thrombotic.

As used herein, the term "anti-thrombotic" refers to a procedure (e.g., a surgical procedure) or a therapeutic agent that reduces the formation of a blood clot (i.e., a thrombus). In some embodiments, the anti-thrombotic reduces the formation of a blood from about 5% to about 99%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%.

In some embodiments, the anti-thrombotic treatment comprises surgical intervention or administration of a therapeutic agent selected from the group consisting of an anti-coagulant or coagulation inhibitory agent, an anti-platelet or platelet inhibitory agent, a thrombin inhibitor, a thrombolytic or fibrinolytic agent, or an anti-inflammatory or NSAID agent.

Example anticoagulant or coagulation inhibitory agents include, but are not limited to, heparin, acenocoumarl, phenprocoumon, sodium crystalline clathrate, warfarin, rivaroxaban, apixaban, and edoxaban. In some embodiments, the anti- coagulant or coagulation inhibitory agent is selected from the group consisting of heparin, sodium crystalline clathrate, and warfarin.

Example anti-platelet or platelet inhibitory agents include, but are not limited to, aspirin, triflusal, clopidogrel, prasugrel, ticagrelor, ticlopidine, cilostazol, vorapaxar, abciximab, eptifibatide, tirofiban, adenosine reuptake inhibitors, dipyridamole, thromboxane inhibitors, thromboxane synthase inhibitors, thromboxane receptor antagonists, and terutroban. In some embodiments, the anti-platelet or platelet inhibitory agent is selected from the group consisting of asprin, piroxicam, and ticlopidine.

Example thrombin inhibitors include, but are not limited to, boropeptides, hirudin, argatroban, bivalirudin, lepirudin, desirudin, melagatran, ximelagatran, and dabigatran. In some embodiments, the thrombin inhibitor is selected from the group consisting of a boropeptide, hirudin, and argatroban.

Example thrombolytic or fibrinolytic agents include, but are not limited to plasminogen activators (e.g., tissue plasminogen activator (t-PA)), anistreplase, urokinase, streptokinase, alteplase, reteplase, and tenecteplase. In some embodiments, the thrombolytic or fibrinolytic agent is selected from the group consisting of a plasminogen activator, anistreplase, urokinase, and streptokinase.

Example anti-inflammatory or NSAID agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib. In some embodiments, the anti-inflammatory or NSAID agent is aspirin or ibuprofen.

One or more additional pharmaceutical agents such as, for example, chemotherapeutics, steroids, immunosuppressants, or other agents such as therapeutic antibodies, can be used in combination with the anti-thrombotic treatment provided herein. The one or more additional pharmaceutical agents can be administered to a patient simultaneously or sequentially.

Example antibodies for use in combination therapy include but are not limited to trastuzumab (e.g. anti-HER2), ranibizumab (e.g. anti-VEGF-A), bevacizumab (e.g. anti -VEGF), panitumumab (e.g. anti-EGFR), cetuximab (e.g. anti-EGFR), rituxan (anti -CD20) and antibodies directed to c-MET.

Example chemotherapeutics include, but are not limited to, proteosome inhibitors (e.g., bortezomib), thalidomide, revlimid, and DNA-damaging agents such as melphalan, doxorubicin, cyclophosphamide, vincristine, paclitaxel, etoposide, and carmustine.

Example steroids include, but are not limited to, corticosteroids such as cortisone, dexamethasone, hydrocortisone, methylprednisolone, prednisolone, and prednisone.

Example immunosuppressants include, but are not limited to, azathioprine, chlorambucil, cyclophosphamide, cyclosporine, daclizumab, infliximab, methotrexate, and tacrolimus.

One or more of the following agents may be used in combination with the anti- thrombolytic treatments provided herein, and are presented as a non-limiting list: a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, SCH 66336, R115777, L778,123, BMS 214662, gefitinib, erlotinib hydrochloride, antibodies to EGFR, imatinib mesylate, intron, ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, vinorelbine, porfimer, erbitux, liposomal, thiotepa, altretamine, melphalan, trastuzumab, fulvestrant, exemestane, ifosfamide, rituximab, C225, alemtuzumab, clofarabine, cladribine, aphidicolin, sunitinib, dasatinib, tezacitabine, Smit, triapine, didox, trimidox, amidox, 3-AP, MDL-101,731, bendamustine, ofatumumab, and GS-1101 (also known as CAL-101).

EXAMPLES

General Methods

Preparative HPLC purifications described herein were performed using a Luna® 10 μm C18(A) LC Column (250×21.2 mm) from Phenomenex with a Dynamax HPLC system.

Compounds provided herein were characterized using analytical HPLC-ESI-MS using an Agilent 1100 series HPLC system equipped with a Luna® 5 μm C18(2) LC Column (100×2 mm) from Phenomenex.

LC-MS analysis provided herein was performed using an Agilent 1100 series HPLC equipped with a 4.6×100 mm Kinetex C18-column (2.6 μm) from Phenomenex. Compound 2 was synthesized as described by Uppal et al., *Invest Radiol.* 2012; 47:553-8.

Yields provided herein were determined by quantitative ICP-MS analysis. Concentrations were determined using either an Agilent 7500a or 8800-QQQ ICP-MS system. All samples were diluted with 0.1% Triton X-100 in 5% nitric acid containing 20 ppb of Lu (as internal standard). The ratio of analyte ion (e.g. Gd (157) to Lu (174.97) was used to quantify the manganese concentration. A linear calibration curve ranging from 0.1 ppb to 200 ppb was generated daily for the quantification.

Relaxation times ($T_1$) were calculated using a Bruker 60 MHz minispec. Longitudinal ($T_1$) relaxation was acquired via an inversion recovery experiment using 10 inversion times of duration ranging between $0.05 \times T_1$ and $5 \times T_1$; tranverse ($T_2$) relaxation was measured using a Carl-Purcell-Meiboom-Gill spin-echo experiment. Relaxivity ($r_{1,2}$) was determined from the slope of a plot of $1/T_{1,2}$ vs. [Metal ion].

Example 1. Synthesis of Compound 1

A solution of EP-2104R (100 mg, 0.023 mmol, see Overoye-Cha, et al., *J. Am. Chem. Soc.*, 2008, 130, 6025) was prepared in tris-buffered saline (2.4 mL, pH 7.4) and stirred at room temperature as Tris[2-carboxyethyl] phosphine hydrochloride (TCEP -HCl) was added (14 mg, 0.048 mmol). The reaction was allowed to proceed for 1 h before the reduced intermediate was isolated by preparative HPLC using the following conditions:

Solvents: A) water with 50 mM ammonium acetate and B) 9:1 v/v acetonitrile/water 50 mM ammonium acetate (pH 6.8). Gradient elution method: 5% B (0 to 6 min), 5% to 95% B (6 min to 29 min), 95% B (29 min to 34 min), 95% to 5% B (34 min to 35 min), 5% B (35 min to 40 min). Flow rate: 15 mL/min.

The fractions containing the desired intermediate were combined and lyophilized overnight. Next, the intermediate was redissolved in deionized water (5 mL) and added quickly to 4 mL of a 2 M solution of cystamine hydrochloride. The reaction was mixed thoroughly and allowed to stand at room temperature for 45 min. LC-MS analysis of the crude reaction mixture revealed that roughly 20% of the starting material was re-oxidized back to EP-2104R. No workup was required to stop the reaction. The desired product 1 was isolated by preparative HPLC using the following conditions:

Solvents: A) water with 50 mM ammonium acetate and B) 9:1 v/v acetonitrile/water 50 mM ammonium acetate (pH 6.8). Gradient elution method: 10% B (0 to 5 min), 10% to 20% B (5 min to 6 min), 20% to 30% B (6 min to 29 min), 30% to 95% B (29 min to 30 min), 95% B (30 min to 34 min), 95% to 10% B (34 min to 35 min), 10% (35 min to 40 min). Flow rate: 15 mL/min.

Figure 1B:
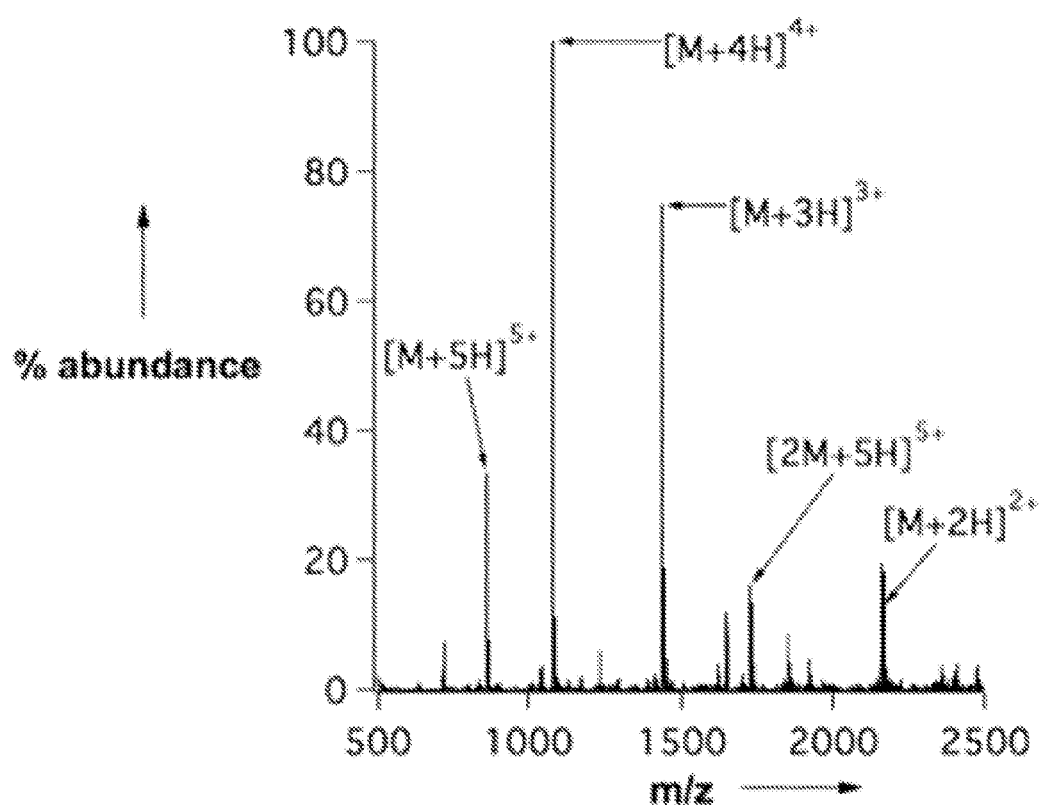
FIG. 1B shows HPLC-ESI-MS analysis of pure Compound 1.

The fractions containing the desired intermediate were combined and lyophilized to give a white solid (Yield: 46%, two steps). The purified product was characterized by analytical HPLC-ESI-MS, as shown in FIG. 1A and FIG. 1B. Retention time: $t_r$=5.0 min. ESI-MS: m/z calc'd for $[C_{158}H_{229}ClGd_4N_{36}O_{56}S_4+2H]^{2+}$ 2161.6, found 2161.6; calc'd for $[C_{158}H_{229}ClGd_4N_{36}O_{56}S_4+3H]^{3+}$ 1441.4, found 1441.6; calc'd for $[C_{158}H_{229}ClGd_4N_{36}O_{56}S_4+4H]^{4+}$ 1081.3, found 1081.6; calc'd for $[C_{158}H_{229}ClGd_4N_{36}O_{56}S_4+5H]^{5+}$ 865.2, found 865.1.

Example 2. Conversion of Compound 1 to EP-2104R

Figure 2:
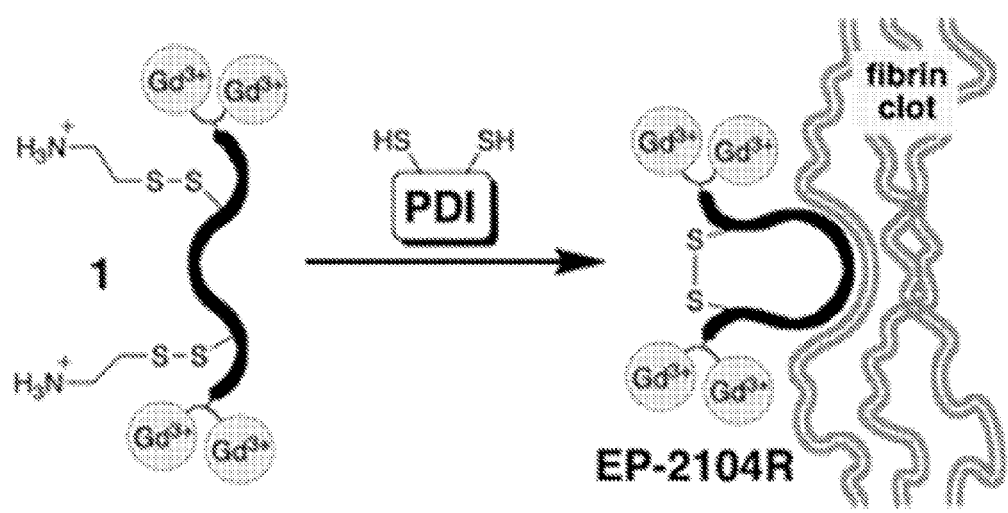
FIG. 2 shows that the mechanism of action for the compounds provided herein is probe activation and retention at a clotting site. PDI activity expressed on the surface of activated platelets in newly formed thrombi catalyzes the conversion of Compound 1 to EP-2104R, which then binds neighboring fibrin with high affinity.

EP-2104R contains a disulfide bond between cysteine residues that is necessary for fibrin binding. Previous studies have demonstrated that any modifications to EP-EP-2104R that prevent disulfide formation between these two cysteine residues blocks binding to fibrin. The compounds described herein include non-natural cysteine derivatives having cystamine groups bound to both of the cysteine side chains to prevent cyclization until the probe encounters PDI, as shown in FIG. 2. In this way, the compound is converted by platelet PDI to EP-2104R, which then is selectively retained in the clot by binding to fibrin. Older clots that no longer possess high PDI activity will not show retention of the probe.

The conversion of Compound 1 to EP-2104R was tested by HPLC using four sets of reactions conditions. All reactions were performed at room temperature in Tris buffer (50 mM Tris, 100 mM NaCl, pH 7.4). In each test, the initial concentration of Compound 1 was 40.0 µM. Stock solutions of PDI (20 mg/L in water), DTT (1000 µM in TBS buffer), and Compound 1 (1000 µM in TBS buffer) were prepared prior to the start of these experiments and stored on ice. Each reaction was allowed to proceed for 15 minutes. The reactions were prepared as follows:

Condition A (untreated): Added 8.0 µL of compound 1 (1000 µM) to 192.0 µL of TBS buffer and mixed.

Condition B (PDI only): Added 8.0 µL of compound 1 (1000 µM) and 40.0 µL of PDI (20 mg/L) to 152.0 µL of TBS buffer and mixed.

Condition C (DTT only): Added 8.0 µL of compound 1 (1000 µM) and 8.0 µL of DTT (1000 µM) to 184.0 µL of TBS buffer and mixed.

Condition D (PDI+DTT): Added 8.0 µL of compound 1 (1000 µM) and 40.0 µL of PDI (20 mg/L) and 8.0 µL of DTT (1000 µL) to 144 µL of TBS buffer and mixed.

Figure 3:
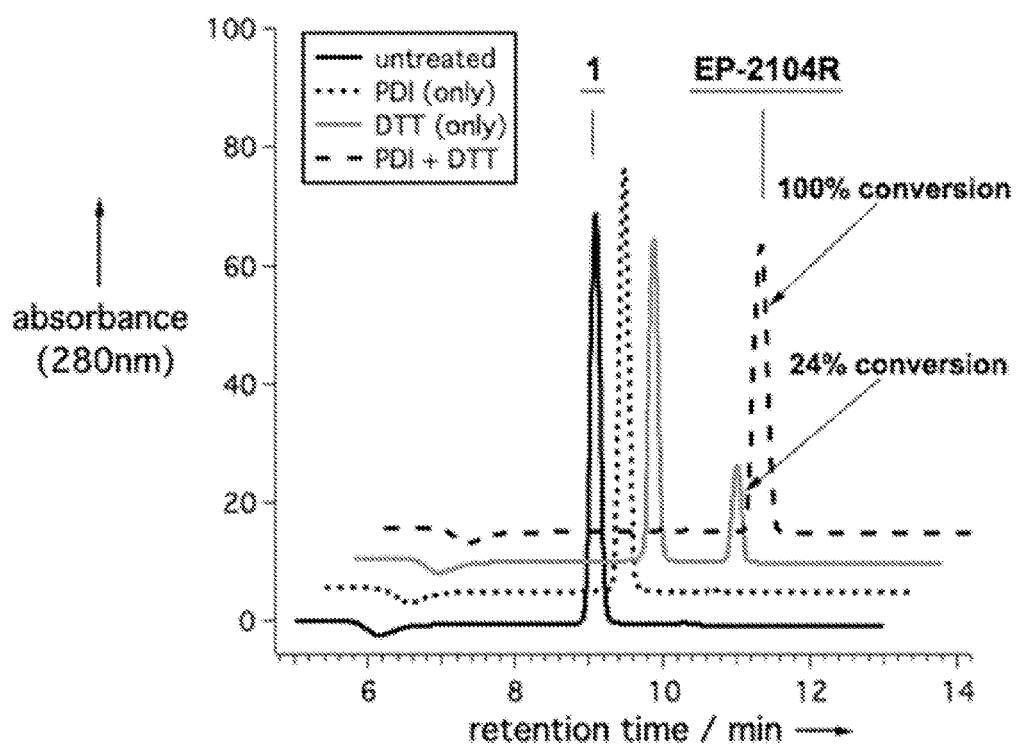
FIG. 3 shows HPLC traces showing the extent of conversion of Compound 1 (40 µM) to EP-2104R after 15 minutes under four different reaction conditions: untreated (no enzyme or DTT added); with PDI (4 mg/L); with DTT (40 µM); and with both PDI (4 mg/L) and DTT (40 µM).

LC-MS analysis was performed using the following conditions:

Solvents: A) water with 10 mM ammonium formate and B) 9:1 v/v acetonitrile/water 10 mM ammonium formate (pH 6.8). Gradient elution method: 5% B (0 to 3 min), 5% to 15% B (3 mM to 3.5 min), 15% to 30% B (3.5 mM to 13.5 min), 30% to 95% B (13.5 min to 14 min), 95% B (14 min to 16.5 min), 95% to 5% B (16.5 min to 17 min), 5% (17 mM to 20 min). Flow rate: 0.8 mL/min. Results of the LC-MS analysis are shown in FIG. 3. Retention Times: 9.0 min (Compound 1) and 10.2 mM (EP-2104R).

Example 3. DD(E) Binding Assay

The fibrin-binding affinities of EP-2104R and Compound 1 were assessed using a previously reported competitive displacement assay (see Ciesienski, et. al., *Mol. Pharm.* 2013, 10, 1100; Kolodziej, et. al., *Bioconjug. Chem.* 2012, 23, 548.) The fluorescent peptide TRITC-Tn6 (structure shown below), which is structurally similar to EP-2104R, is mixed with a soluble protein fragment of fibrin (DD(E)). This fluorescent peptide binds to the same discrete site on DD(E) that EP-2104R is known to bind. If EP-2104R is present at sufficiently high concentrations, then it will displace the fluorescent peptide from the protein causing a decrease in the observed fluorescence anisotropy. Since the dissociation constant of the TRITC-Tn6 probe is known ($K_d$=0.51 µM) this method can be used to determine the dissociation constant of EP-2104R as well as the dissociation constants of other compounds that compete for the same binding site.

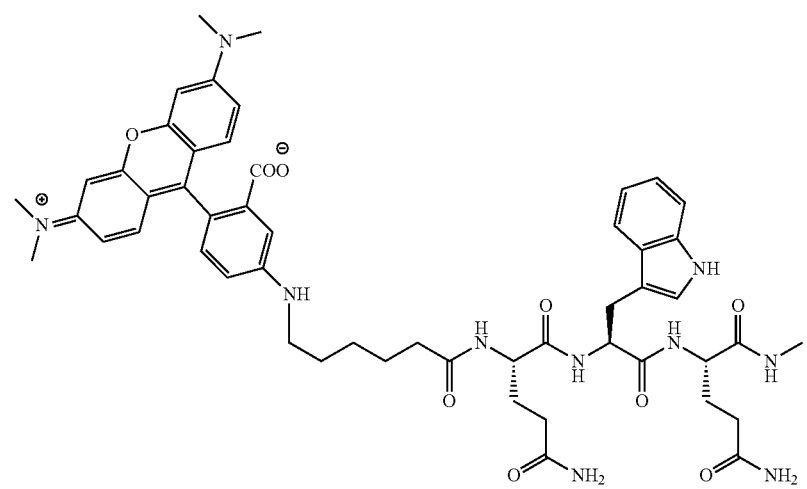

-continued

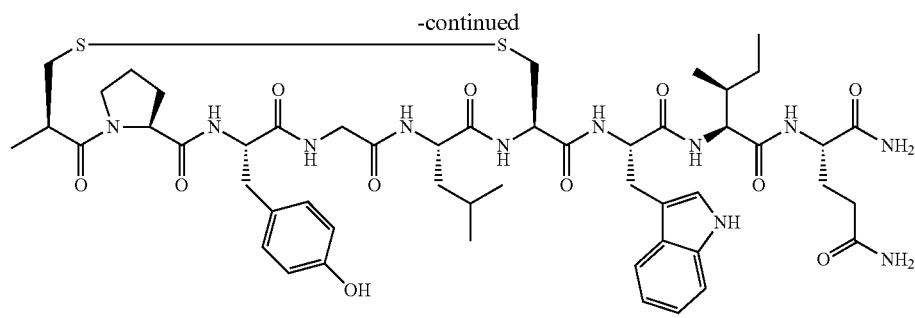

TRITC-Tn6 peptide

Figure 4:
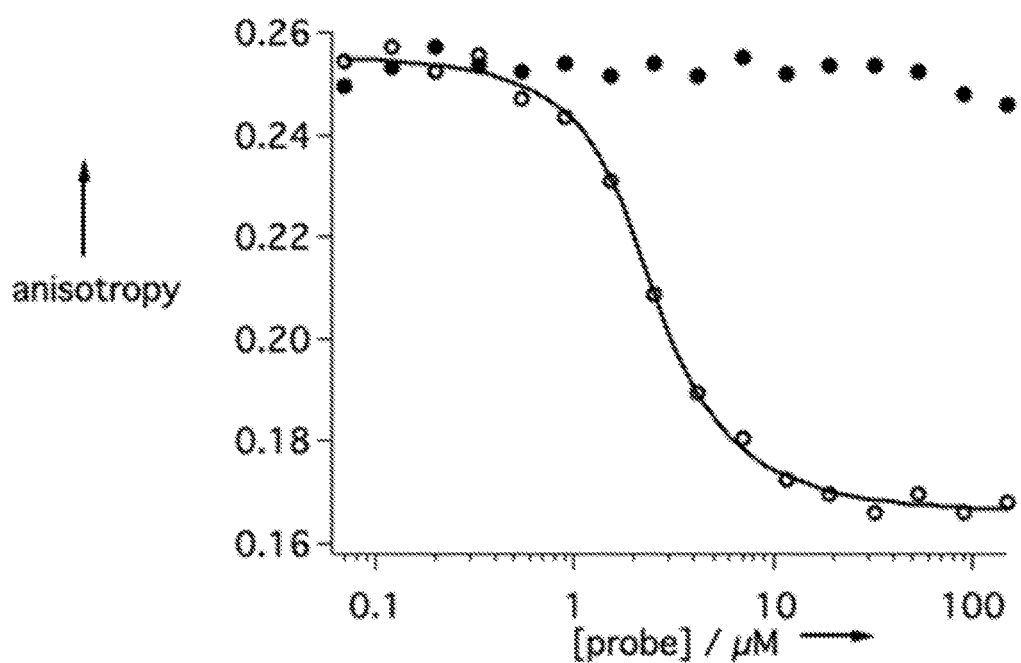
FIG. 4 shows the binding of probes to DD(E) (2 µM) detected by measuring the decrease in fluorescence anisotropy that occurs upon competitive displacement of the TRITC-Tn6 probe (0.1 µM).

A series of dilutions of EP-2104R and Compound 1 were prepared in assay buffer with their concentrations ranging from 200 μM down to 0.09 μM. Both series consisted of 16 tubes with a dilution factor of 0.6 between consecutive tubes. The assay buffer composition was 50 mM Tris, 100 mM NaCl, 2 mM $CaCl_2$, and 0.01% Triton X-100 (pH 7.8). The serial dilutions of the two compounds were then each mixed 3:1 with a solution containing both the TRITC-Tn6 peptide (0.4 μM) and the DD(E) protein (8.0 μM) also in assay buffer. The final concentration range for the two serial dilutions was 150 μM to 0.07 μM and the final concentrations for the TRITC-Tn6 peptide and DD(E) were 0.1 μM and 2 μM, respectively. After the contents of each tube were mixed they were then transferred to a 384-well small-volume microplate from Greiner Bio-One (#784900). Each well of the microplate received 10 μL and each tube of the two serial dilutions was measured in triplicate. The plate was then read at room temperature by a Tecan Infinity® F200 Pro plate reader equipped with a filter set for the tetramethyl-rhodamine dye (ex 535 nm, em 590). The observed anisotropy values measured for each solution were then plotted as a function of competitor concentration. The dissociation constant for EP-2104R ($K_d$=0.16 μM) was determined by least-squares regression. The $K_d$ of Compound 1 could not be accurately measured due to the lack of displacement observed over the selected concentration range. Results of the DD(E) binding assay are shown in FIG. 4.

Example 4. Real-time Kinetics for Converting Compound 1 to EP-2104R

Fluorescence Polarization Assay of Enzyme Kinetics

The catalytic conversion of Compound 1 to EP-2104R by PDI was monitored in real-time by observing the gradual displacement of the fluorescent TRITC-Tn6 peptide from DD(E) as EP-2104R was generated. For these experiments, the reactions were each performed in the presence of 2.0 μM DD(E) and 0.1 μM TRITC-Tn6 with an initial concentration of Compound 1 at 10.0 μM. The reaction was performed under four different sets of reaction conditions to demonstrate the catalytic effect of PDI.

Stock solutions of PDI (20 mg/L in water), DTT (100 μM in assay buffer), and Compound 1 (100 μM in assay buffer) were prepared prior to the start of these experiments and stored on ice. The composition of the assay buffer is described in the table caption above (Table S2). Additionally, a 4x solution containing both the TRITC -Tn6 peptide (0.4 μM) and DD(E) (8.0 μM) was also prepared. All reactions were performed at room temperature in assay buffer (50 mM Tris, 100 mM NaCl, 2 mM $CaCl_2$, 0.01% Triton X-100, pH 7.8). In each case the initial concentration compound 1 was 10.0 μM. The reactions were assembled as follows:

Condition A (untreated): Added 20.0 μL of compound 1 (100 μM) and 50.0 μL of 4x TRITC-Tn6/DD(E) solution to 130.0 μL of assay buffer and mixed.

Condition B (PDI only): Added 20.0 μL of compound 1 (100 μM) and 10.0 μL of PDI (20 mg/L) and 50.0 μL of 4x TRITC-Tn6/DD(E) solution to 120.0 μL of assay buffer and mixed.

Condition C (DTT only): Added 20.0 μL of compound 1 (100 μM) and 20.0 μL of DTT (100 μM) and 50.0 μL of 4x TRITC-Tn6/DD(E) solution to 110.0 μL of assay buffer and mixed.

Condition D (PDI +DTT): Added 20.0 μL of compound 1 (100 μM) and 10.0 μL of PDI (20 mg/L) and 20.0 μL of DTT (100 μL) and 50.0 μL of 4x TRITC-Tn6/DD(E) solution to 100.0 μL of assay buffer and mixed.

Figure 5:
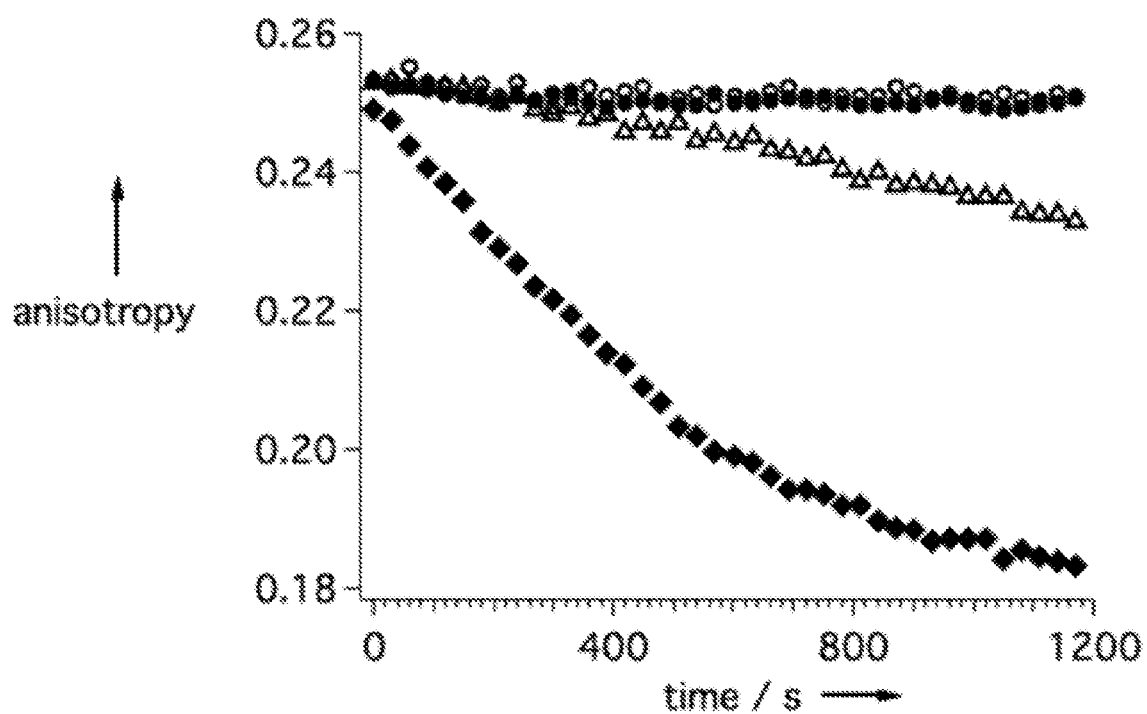
FIG. 5 shows real-time conversion of Compound 1 to EP-2104R by measuring the decrease in fluorescence anisotropy that occurs upon competitive displacement of the TRITC-Tn6 probe from DD(E) under four different reaction conditions: untreated (○); 1 mg/L PDI (●); 10 µM DTT (Δ); and 10 µM DTT plus 1 mg/L PDI (♦).

Immediately after mixing, samples of each of the reactions were transferred to a 384-well small-volume microplate from Greiner Bio-One (#784900). Each well of the microplate received 10 μL and six replicates were performed for each of the four reaction conditions. Replicate wells were averaged together. The plate was then read at room temperature using a Tecan Infinity® F200 Pro plate reader equipped with a filter set for the tetramethylrhodamine dye (ex 535 nm, em 590). The read intervals were space 30 seconds apart over the duration of 20 minutes. The observed anisotropy values for each solution were plotted as a function of time and are shown in FIG. 5.

Relaxation Assay of Enzyme Kinetics

The catalytic conversion of Compound 1 to EP-2104R by PDI was also followed in real-time by measuring the change in $T_1$ that occurs when the reaction was performed in the presence of a high concentration of DD(E). Upon binding to DD(E), the rotational correlation time of EP-2104R increased resulting in an increase in its observed relaxivity. The reaction was run under four different conditions in order to illustrate catalytic effects of PDI.

Stock solutions of PDI (20 mg/L in water), DD(E) (40.7 μM in assay buffer), DTT (100 μM in assay buffer), and Compound 1 (100 μM in assay buffer) were prepared prior to the start of these experiments and preheated to 37° C. All reactions were performed in the presence of 12.0 μM DD(E) at 37° C. in assay buffer (50 mM Tris, 100 mM NaCl, 2 mM $CaCl_2$, 0.01% Triton X-100, pH 7.8). In each case the initial concentration Compound 1 was 10.0 μM. The reactions were assembled in glass inserts (Agilent #5181-3377) as follows:

Condition A (untreated): Added 20.0 μl of compound 1 (100 μM) and 59.0 μL of DD(E) solution (40.7 μM) to 121.0 μL of assay buffer and mixed.

Condition B (PDI only): Added 20.0 µL of compound 1 (100 µM) and 59.0 µL of DD(E) solution (40.7 µM) and 30.0 µl of PDI (20 mg/L) to 91.0 µL of assay buffer and mixed.

Condition C (DTT only): Added 20.0 µL of compound 1 (100 µM) and 59.0 µl of DD(E) solution (40.7 µM) and 20.0 µL of DTT (100 µM) to 101.0 µL of assay buffer and mixed.

Condition D (PDI+DTT): Added 20.0 µL of compound 1 (100 µM) and 59.0 µL of DD(E) solution (40.7 µM) and 30.0 µL of PDI (20 mg/L) and 20.0 µL of DTT (100 µL) to 71.0 µl of assay buffer and mixed.

Figure 6:
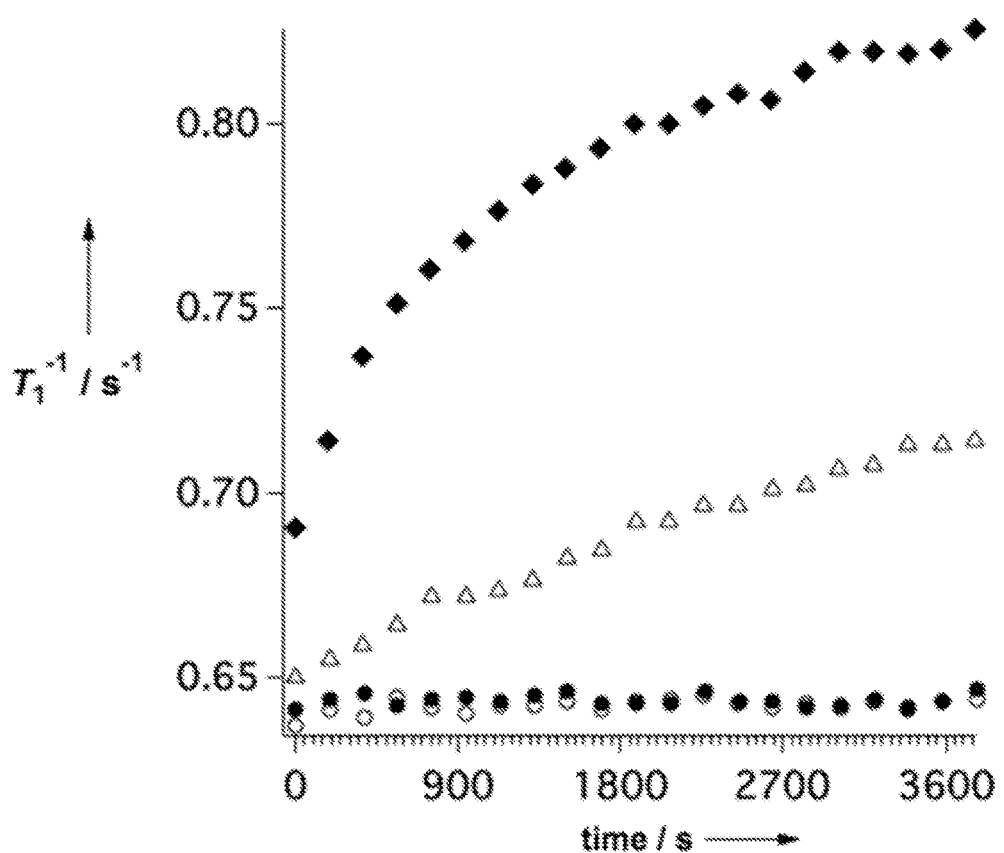
FIG. 6 shows real time conversion of Compound 1 to EP-2104R by measuring the increase in $1/T_1$ that occurs as a result of EP-2104R binding to DD(E). The concentration of DD(E) was 12.0 µM for these experiments. The reaction was performed under four different conditions: untreated (●), 3 mg/L PDI (○), 10 µM DTT (Δ), and 3 mg/L PDI plus 10.0 µM DTT (♦).

The relaxation time $T_1$ was monitored for each reaction over the course of 1 h at 37° C. in a 60 MHz minispec from Bruker. The inverse of the $T_1$ values were then plotted as a function of time as shown in FIG. 6. The rate of conversion of 1 to EP-2104R was most rapid for the reaction performed under condition D in which both PDI and DTT were present simultaneously. The presence of DTT alone (condition C) also promotes the conversion of compound 1 but at a much slower rate.

Relaxivity Measurements

Figure 7A:
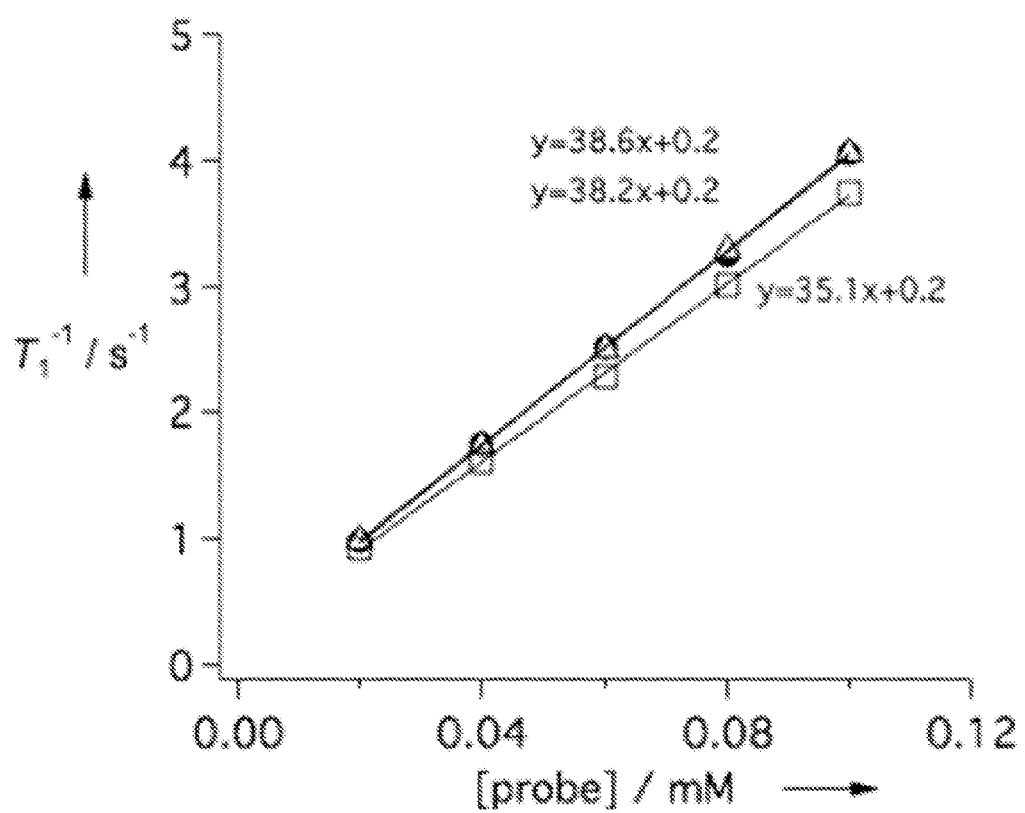
FIG. 7 shows the inverse of the $T_1$ values for each solution plotted as a function of probe concentration. The slope of each line represents the relaxivity of the specified compound under the indicated conditions. Values were measured in the absence of DD(E). Values associated with Compound 1 are indicated with open triangles, those associated with Compound 2 are indicated with open squares and those associated with EP-2104R are represented with closed circles.
FIG. 7B shows the inverse of the $T_1$ values for each solution plotted as a function of probe concentration. The slope of each line represents the relaxivity of the specified compound under the indicated conditions. Values were measured in the presence of 30.5 µM DD(E). Compound 1 (open triangles), Compound 2 (open squares) and EP-2104R (closed circles).
Figure 7B:
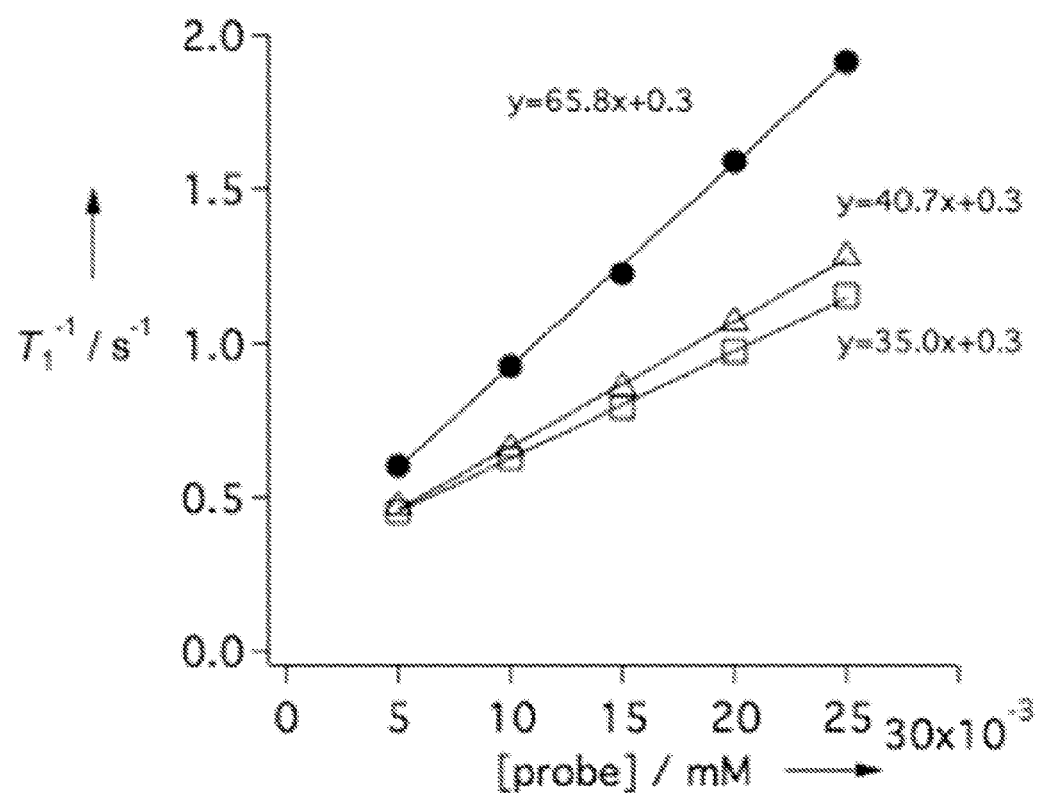

The relaxivities of Compounds 1, 2, and EP-2104R were measured in both the presence an absence of DD(E) at 37° C. These experiments were performed in assay buffer (50 mM Tris, 100 mM NaCl, 2 mM $CaCl_2$, 0.01% Triton X-100, pH 7.8). A series of five dilutions for each probe was prepared (20 µM, 40 µM, 60 µM, 80 µM, and 100 µM). A second series of dilutions for each probe each containing 30.5 µM DD(E) was also prepared (5 µM, 10 µM, 15 µM, 20 µM, and 25 µM). The $T_1$ of each of these solutions was then measured at 37° C. using a 60 MHz minispec from Bruker. The relaxivity of each compound under the defined conditions was calculated based on the slopes of the lines plotted in FIG. 7A and FIG. 7B.

Example 5. Phantom Imaging

A series of three phantoms with glass inserts containing Compounds 1, 2, and EP -2104R were imaged to demonstrate how the catalytic activity of PDI under reducing conditions results in the conversion of Compound 1 to EP-2104R, which then binds fibrin allowing the clot to be visualized. The EP-2104R probe and Compound 2 were included in this experiment to serve as positive and negative controls for fibrin binding, respectively. The final probe concentration in each of these inserts was 10 µM. The first insert on the far left of each phantom contained a solution of fibrinogen only (12.4 µM) with no probe added. This insert served as a background reference from which the signals of the other inserts were compared. The probe solutions of phantom 1 all contained fibrinogen (12.4 µM) where as those of phantoms 2 and 3 contained clotted fibrin (12.4 µM). The inserts of phantom 3 were furthermore subjected to a high-speed spin to pellet the fibrin.

Materials

Many of the solutions used in this experiment were prepared in platelet wash buffer (PWB): 10 mM $Na_3$(citrate), 80 mM NaCl, 20 mM $Na_2PO_4$, 1% w/v glucose, pH 7.4. Prior to the experiment, a solution of human fibrinogen (EMD Milipore #341576) was prepared and dialyzed in PWB. The concentration of this fibrinogen stock was 18.5 µM. The solution was then sterile filtered by passing through a 0.2 µm filter. Stock solutions (1 mM each) of DTT, 1, 2, and EP-2104R were also prepared in PWB. These were then stored on ice along with thawed stocks of PDI (20 mg/L in water), thrombin (100 U/mL in water), and $CaCl_2$ (1 M).

Procedure

The following two solutions were prepared for each of the three probes (1, 2, and EP-2104R):

| Solution 1 (With PDI & DTT) | Solution 2 (Without PDI and DTT) |
|---|---|
| 30 µL probe solution (1 mM) | 30 µL probe solution (1 mM) |
| 30 µL DTT solution (1 mM) | 775 µL PWB |
| 150 µL PDI (20 mg/L) | 150 µL $H_2O$ |
| 745 µL PWB | |

Both solutions were then incubated for 30 minutes at room temperature in order to allow the solutions containing the enzyme time to react. The two solutions were then split equally into two aliquots (477.5 µL each). One set received 22.5 µL of a solution of $CaCl_2$ (1 M) followed by 7.16 µL of thrombin (100 U/mL) while the other received 22.5 µL of $H_2O$.

Next, 100 µL of each probe solution was mixed with 200 µL of the filtered fibrinogen solution (18.5 µM) in a glass insert (Agilent #5181-3377). These samples were then allowed to stand at room temperature for 1 hr to allow those containing thrombin enough time to fully clot. The inserts that did not receive thrombin were used for phantom 1 while the inserts that did were used for phantoms 2 and 3. Additionally, the tubes for phantom 3 were spun at high speed in a bench top microfuge in order to pellet the fibrin clots.

Figure 8:
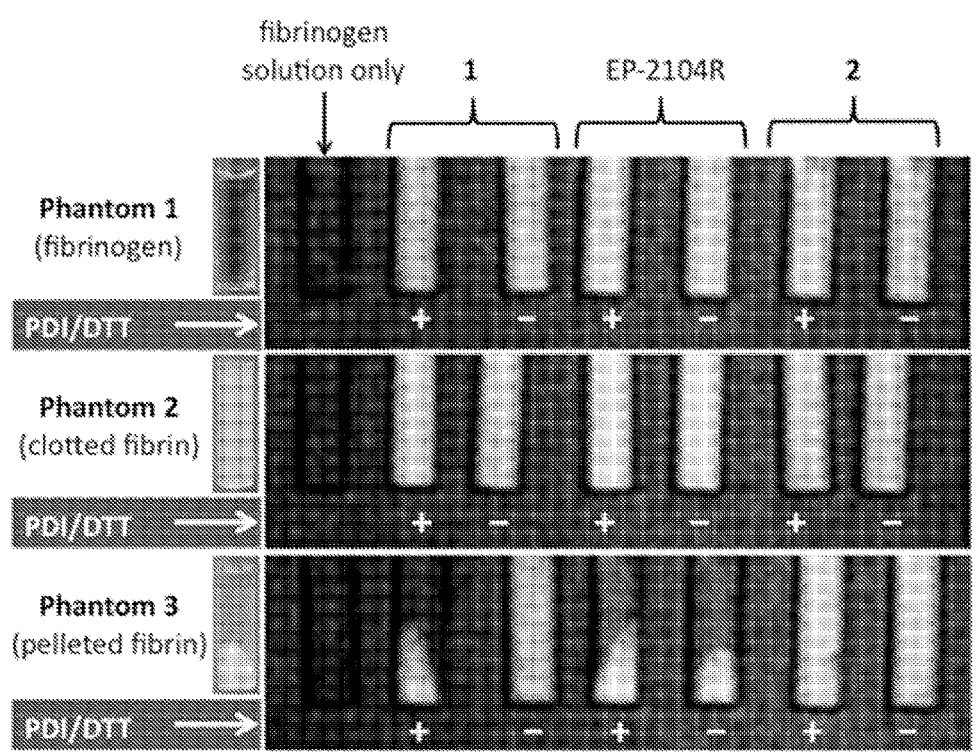
FIG. 8 shows T1-weighted MR images of phantoms 1-3 obtained at 1.5T. Solutions of 1, EP-2104R, and 2 treated with both PDI and DTT (+) are paired with solutions that were not treated (−). The probe-containing solutions of phantoms 2 and 3 were treated with thrombin and $CaCl_2$ to clot the fibrinogen. The inserts of phantom 3 were centrifuged to pellet the clots.
Figure 9A:
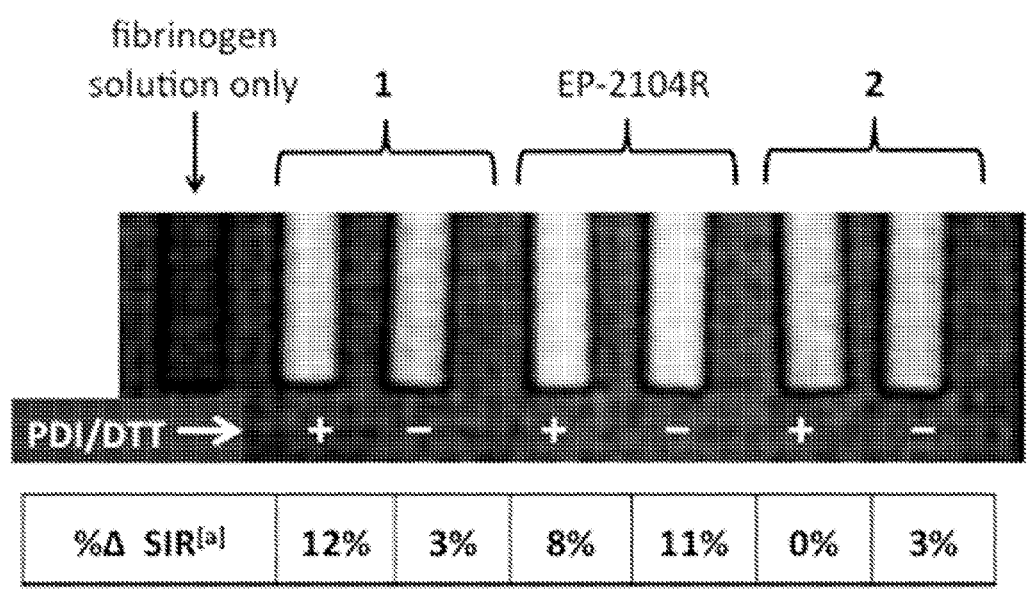
FIG. 9A shows percent change in signal-intensity-ratio (SIR) observed when comparing phantom 2 to phantom 1. The signal-intensity-ratio (SIR) for each insert was calculated by dividing the averaged signal intensity measured over each insert by the averaged signal intensity measured over the fibrinogen solution on the left.
Figure 9B:
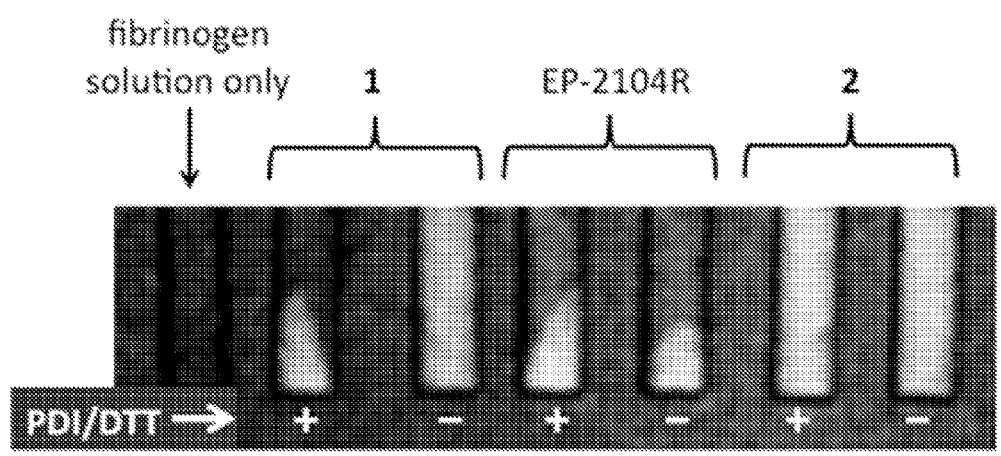
FIG. 9B shows a comparison of signal-intensity-ratios of phantom 3 to phantom 1.

Each phantom was constructed from a 50 mL polypropylene Falcon tube with a series of holes drilled into the side through which the glass inserts were inserted. The Falcon tubes were filled with deionized water and capped before imaging at room temperature in a 1.5T MRI. Imaging was performed on a Siemens 1.5T Avanto using an inversion recovery prepared turbo spin echo sequence (IR-TSE). The repetition time, echo time, and inversion time was 4000, 16, and 2500 ms respectively. The slice thickness was 4 mm, matrix size was 128×64 for an in-plane resolution of 0.55× 0.55 mm. Eight averages were performed. TI-weighted MR images of phantoms 1-3 obtained at 1.5T are shown in FIG. 8. Details regarding the data analysis are shown in FIG. 9A and FIG. 9B.

Example 6. Synthesis of FBP14 and FBP15

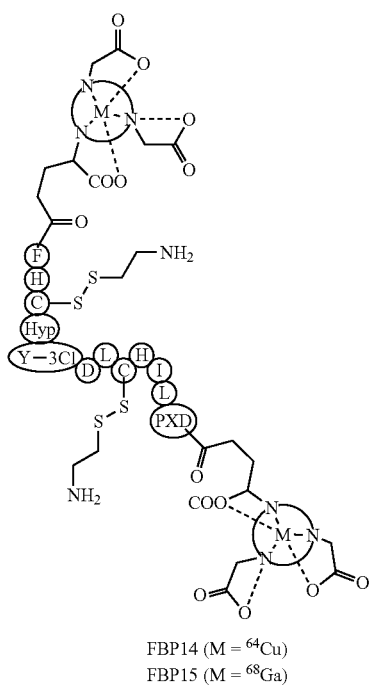

FBP14 (M = $^{64}$Cu)
FBP15 (M = $^{68}$Ga)

A solution of (NODAGA)2-peptide (0.6 mg, 267 nmol) was dissolved in tris-buffered saline (1 mL, pH 7.4) and 500 μL of immobilized Tris[2-carboxyethyl] phosphine (TCEP) was added (Thermo Scientific). The reaction was allowed to proceed for 24 h at room temperature before the reduced intermediate was separated from the gel by filtration. Next, 213 μL of a 1 M solution of mercaptoethylamine (MEA, 213 μmol) was added and the reaction mixture allowed to stand at room temperature for more 18 h. The desired product (NODAGA)2-MEA-peptide was isolated by preparative HPLC using the following conditions:

Solvents: A) H$_2$O with 0.1% trifluoroacetic acid (TFA) and B) CH$_3$CN with 0.1% TFA. Gradient elution method: 0-35 min, 5 to 55% B; 35-39 min, 55 to 95% B; 40-42 min, 95% B; 42-42.1 min, 95 to 5% B; 42.1-47.1 min, 5% B.

Figure 10:
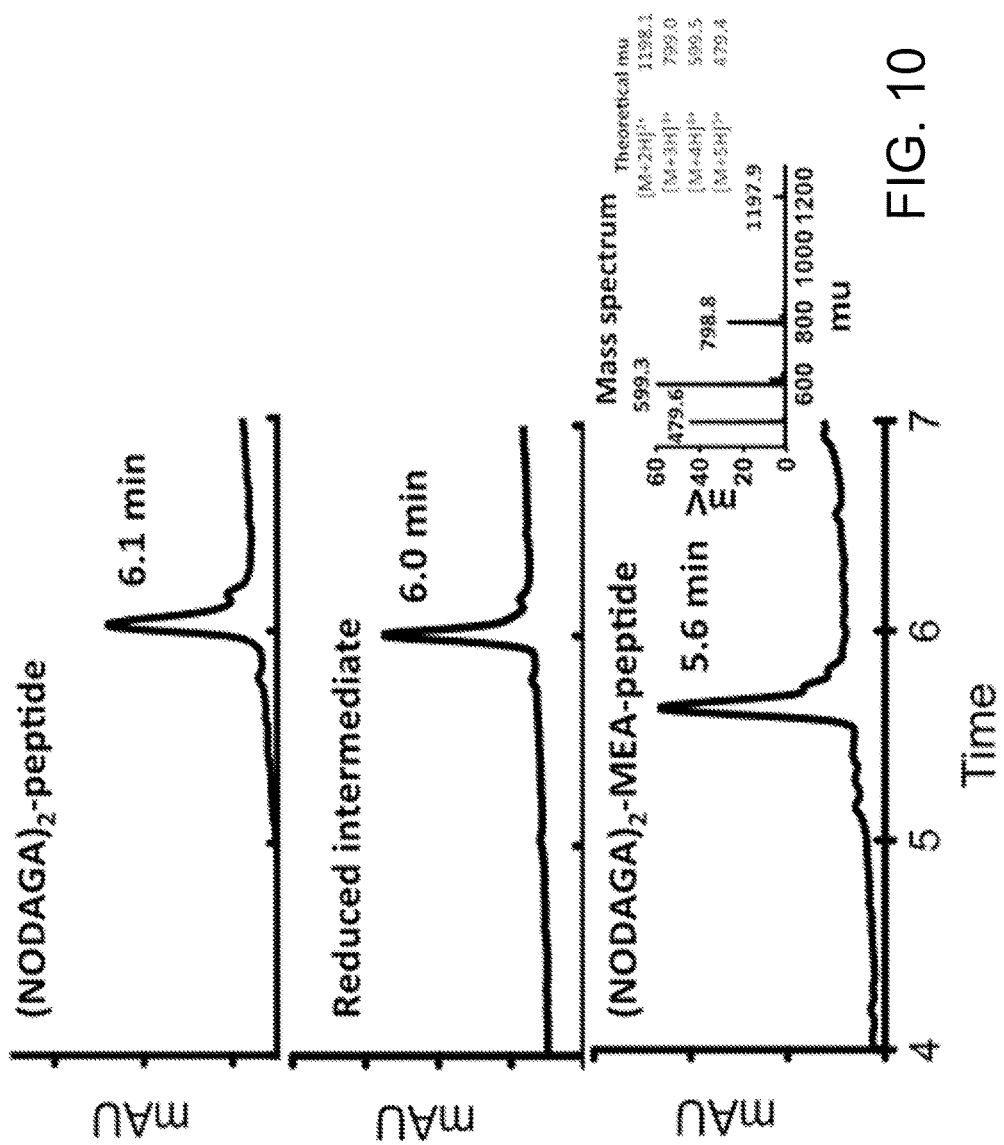
FIG. 10 shows HPLC-ES-MS analysis of $(NODAGA)_2$-MEA-peptide and HPLC chromatograms of the respective intermediates.

The purified product was characterized by analytical HPLC-ESI-MS using the following conditions:

Solvents: A) H$_2$O with 0.1% trifluoroacetic acid (TFA) and B) CH$_3$CN with 0.1% TFA. Elution method: 5% to 95% B (in 10 min), 95% B (10 min to 12 min), 95% to 5% B (12 min to 12.1 min), 5% B (12.5 min to 15 min). Flow rate: 0.8 mL/min. The retention time for (NODAGA)$_2$-MEA-peptide was t$_r$=5.6 min. The identity of the final product was confirmed by ESI-MS (m/z calc'd for [C$_{105}$H$_{154}$ClN$_{25}$O$_{29}$S$_2$+2H]$^{2+}$1198.1, found 1197.9). Chemical purities of intermediates and final compound were >97% determined by analytical HPLC analysis. Results of the HPLC analysis and retention times are shown in FIG. 10.

FBP14 and FBP15 were obtained with yields ≥99% by reaction of (NODAGA)$_2$-MEA-peptide with 1 mCi of $^{64}$CuCl$_2$ or $^{68}$GaCl$_3$ (30 min at 50° C., 4.5×10$^{-5}$M peptide), respectively.

Example 7. In Vivo Rat Model

General Procedure

In vivo studies were performed in a rat model of arterial thrombosis induced by ferric chloride application (see Kurz, et al., *Thrombosis Research*, 1990, 60, 269-280).[1] Briefly, adult male Sprague-Dawley rats (250-300 g, Charles River Laboratories) were anesthetized with isoflurane (4% induction, 2-2.5% maintenance, in medical air), and a midline neck incision was performed to expose the right common carotid artery. A small piece of filter paper (Whatman #1; size: 2×1 mm) was soaked for 1 min in a solution of ferric chloride (Sigma, 25% w/v, in sterile saline), and then applied on the vessel for 5 min to induce thrombosis. At the end of the procedure, the surgical site was rinsed with sterile saline to remove the excess of ferric chloride, and the formation of the clot was confirmed by visual inspection. Femoral artery and vein catheterization was performed to collect blood samples and to deliver the probe, respectively. Approximately 15-30 min after the induction of thrombosis, the animals were injected with the molecular probe FBP14.

Biodistribution

Figure 11:
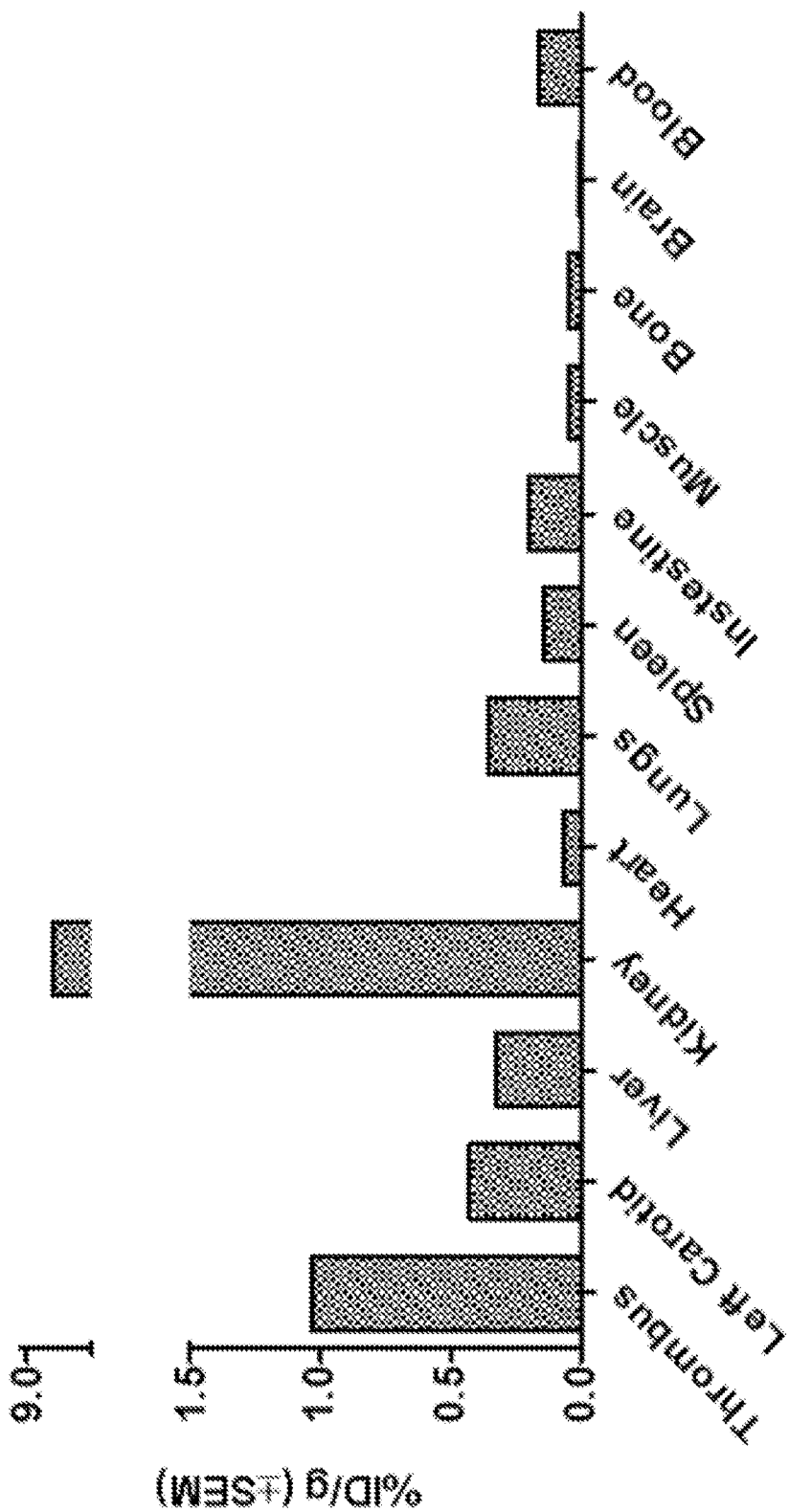
FIG. 11 shows the biodistribution for FBP14 at 60 minutes post-injection showing high uptake in the thrombus.

Biodistribution studies showed a high uptake of FBP14 in the thrombus (1.03% ID/g), which is 2-fold higher than the uptake found in the contralateral vessel. At 60 min post-injection the thrombus is the tissue with the second highest uptake, just after the kidneys. These results suggest that the non-binding fibrin precursor FBP14 is converted in vivo to FBP8 (shown below), which selectively binds fibrin with high affinity. The biodistribution of FBP14 at 60 min post-injection is shown in FIG. 11.

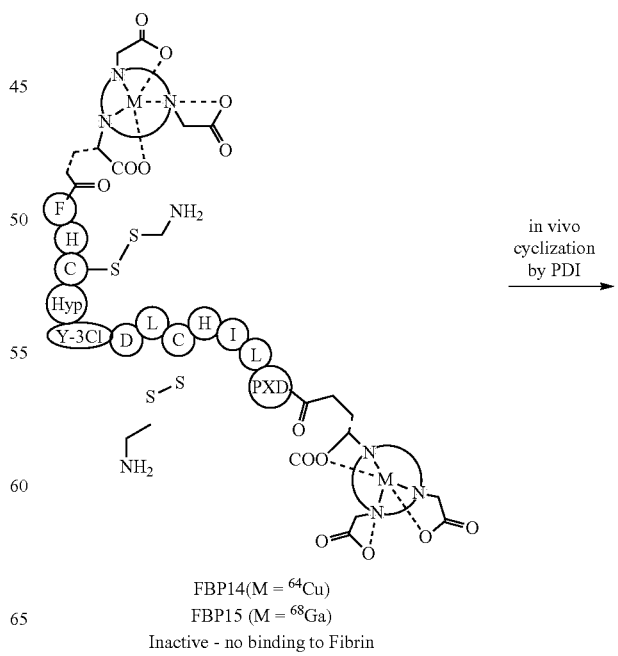

FBP14(M = $^{64}$Cu)
FBP15 (M = $^{68}$Ga)
Inactive - no binding to Fibrin in vivo cyclization by PDI →

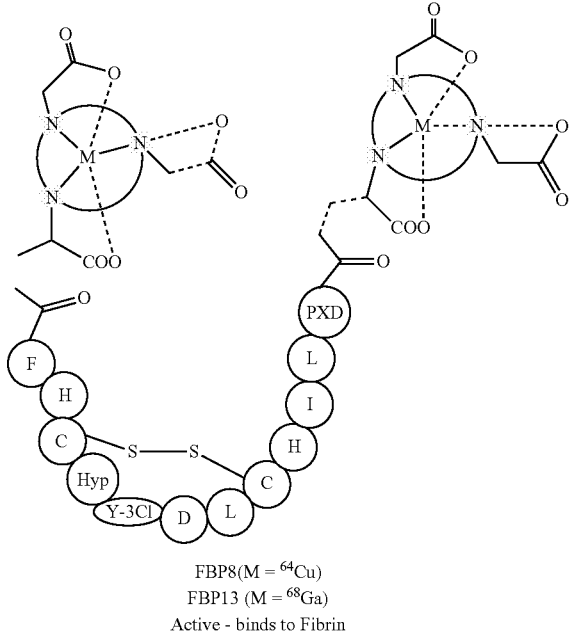

FBP8(M = $^{64}$Cu)
FBP13 (M = $^{68}$Ga)
Active - binds to Fibrin

Ex Vivo Autoradiography

Figure 12:
FIG. 12 shows results of an ex vivo autoradiography assay.
Figure 12:
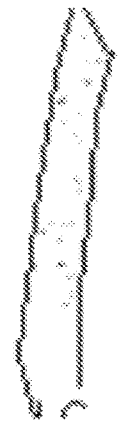

Ex vivo autoradiography confirmed the results obtained from biodistribution. A hyperintense region was detected in the right carotid (RC) segment corresponding to the location where the clot was induced, but not in the contralateral vessel (LC). As shown in FIG. 12, the activity in the RC (containing the thrombus) was over 5-fold higher than activity in the LC.

Clearance and In Vivo Stability of Probe

Figure 13:
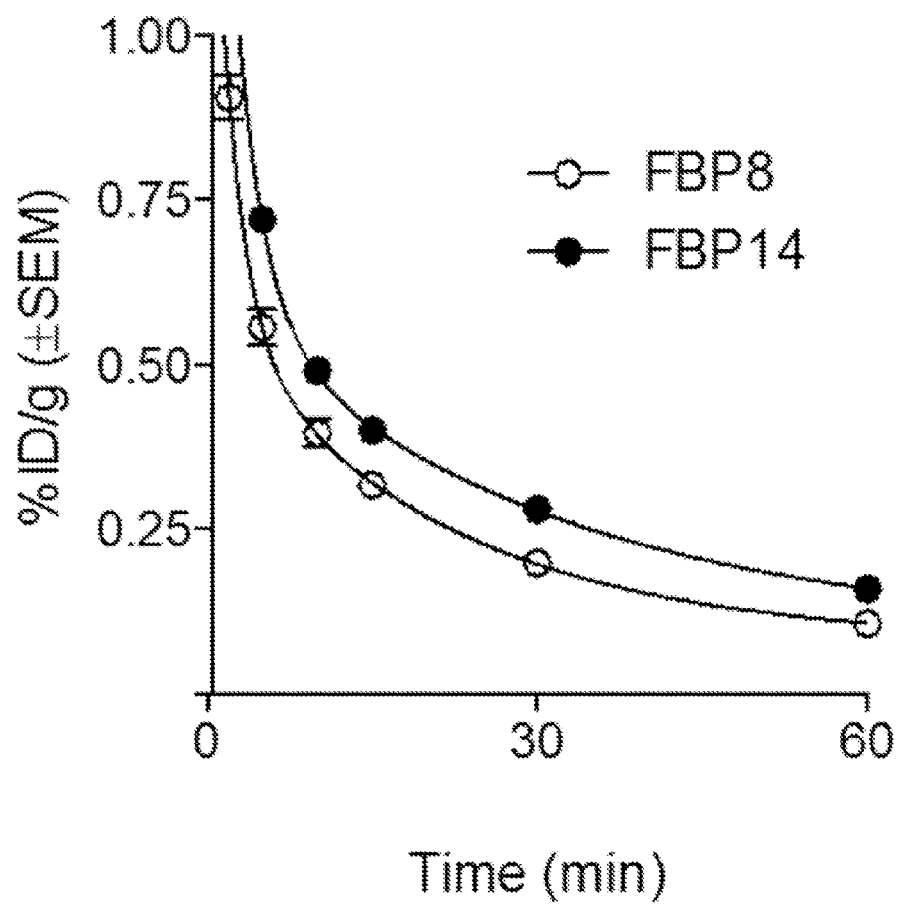
FIG. 13 shows pharmacokinetic data from ex vivo blood analyses for FBP8 and FBP14.

Serial blood draws were collected up to 60 min post-injection to determine the clearance of activity from the blood and the in vivo stability of the probe. These results showed that FBP14 has a rapid elimination from circulation, which is very similar to that observed for FBP8 (FIG. 13).

Post-Injection HPLC Analysis

Figure 14B:
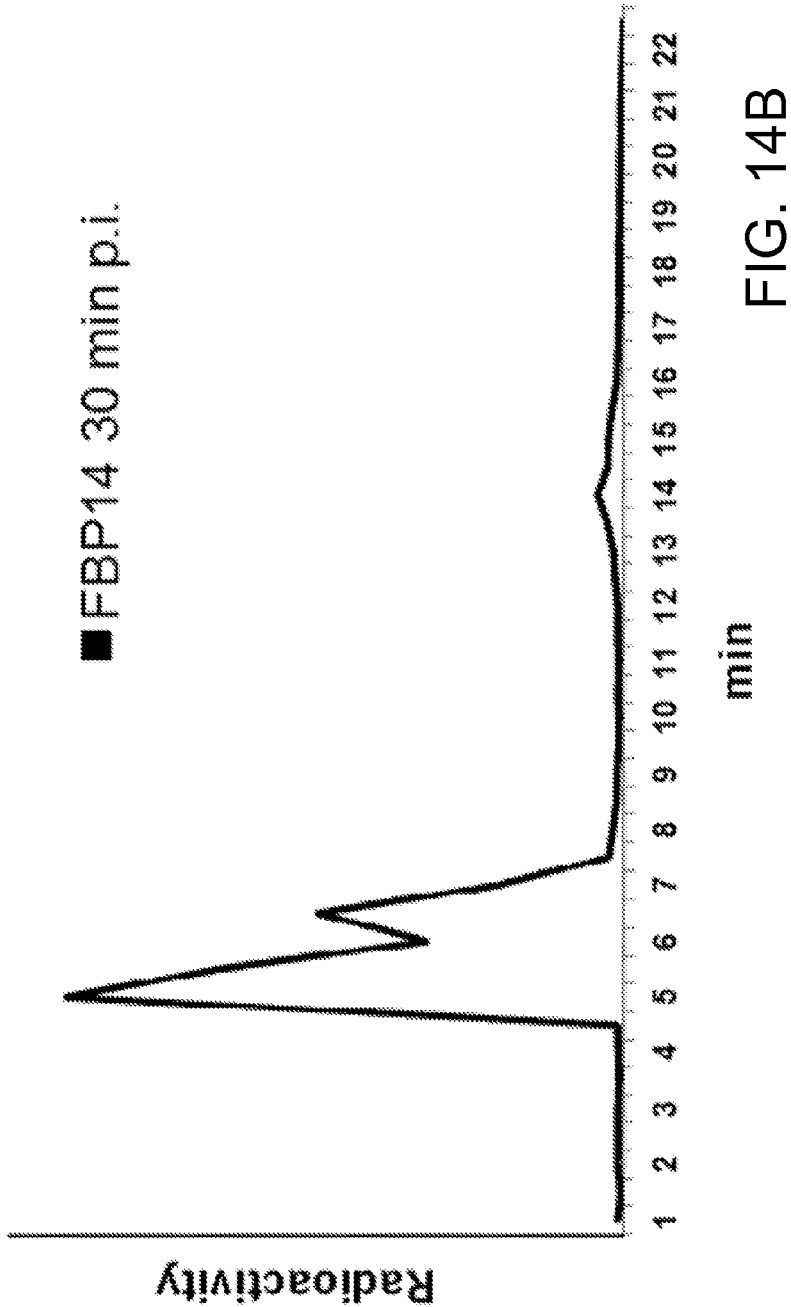
FIG. 14B shows a radio-HPLC analysis of blood drawn 30 minutes after injection of FBP14 to a control rat (non-thrombotic rat).

HPLC analysis of blood plasma taken 30 min post-injection in a thrombotic rat showed the presence of a single peak with the same retention time of FBP8, supporting the hypothesis that FBP14 is cyclized in vivo to the active probe FBP8 (FIG. 14A). The same studies performed with FBP14 in a control rat showed a different trend. In this case, 30 min after injection we observed a complete degradation of FBP14 (FIG. 14B). This result suggests that in a healthy animal (no clot induced) the linear probe is not converted to FBP8 and rapidly metabolized.

Example 8. Synthesis of Mixed Disulfide Fluorescent Activatable Probe

An optical probe was designed based on the peptide sequence TRITCAha -QWECPYGLCWIQ-NH$_2$. Here, the N-terminus of the peptide was modified with a tetramethylrhodamine dye (TRITC) connected via a 6-aminohexanoic acid linker and the two cysteine residues were covalently protected as mixed disulfides with cystamine groups to prevent uncatalyzed cyclization. This was done by mixing a 0.5 µg/mL solution the reduced form of the peptide in DMSO (1 mL) with a 2 M solution of cystamine in 1:1 DMSO/water (2 mL). The reaction was allowed to proceed for 45 minutes before isolating the desired product by preparative HPLC.

Example 9. Conversion of Mixed Disulfide Fluorescent Probe to Cyclized Form

LC-MS Analysis

Figure 15A:
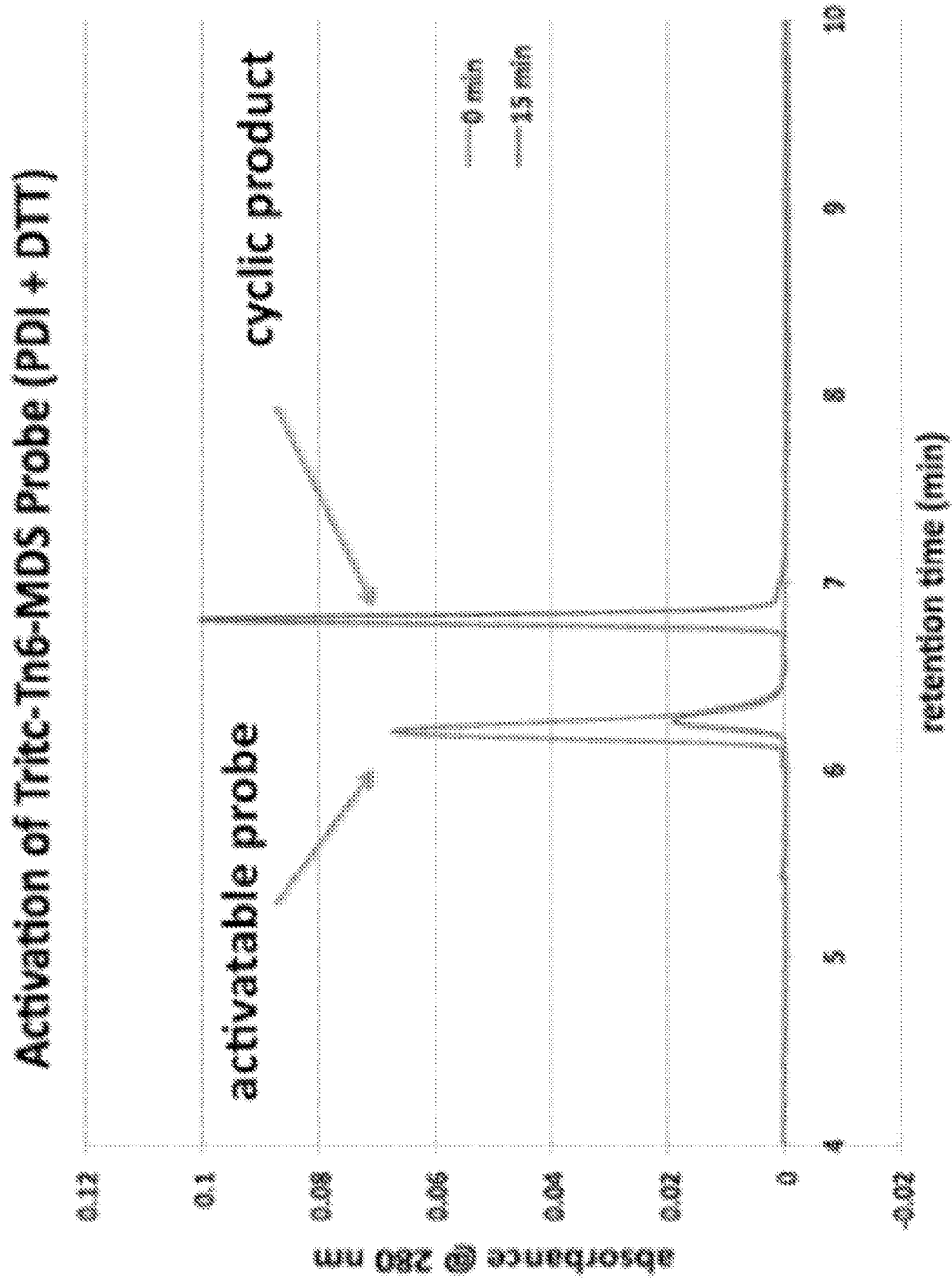
FIG. 15 shows an HPLC trace of the conversion of a linear TRITC-Tn6-MDS probe to the cyclized form under slightly reducing conditions, catalyzed in the presence of PDI.
FIG. 15B shows the conversion kinetics of a linear TRITC-Tn6-MDS probe (6.5 µM) to the corresponding cyclized form under three different conditions.
Figure 15B:
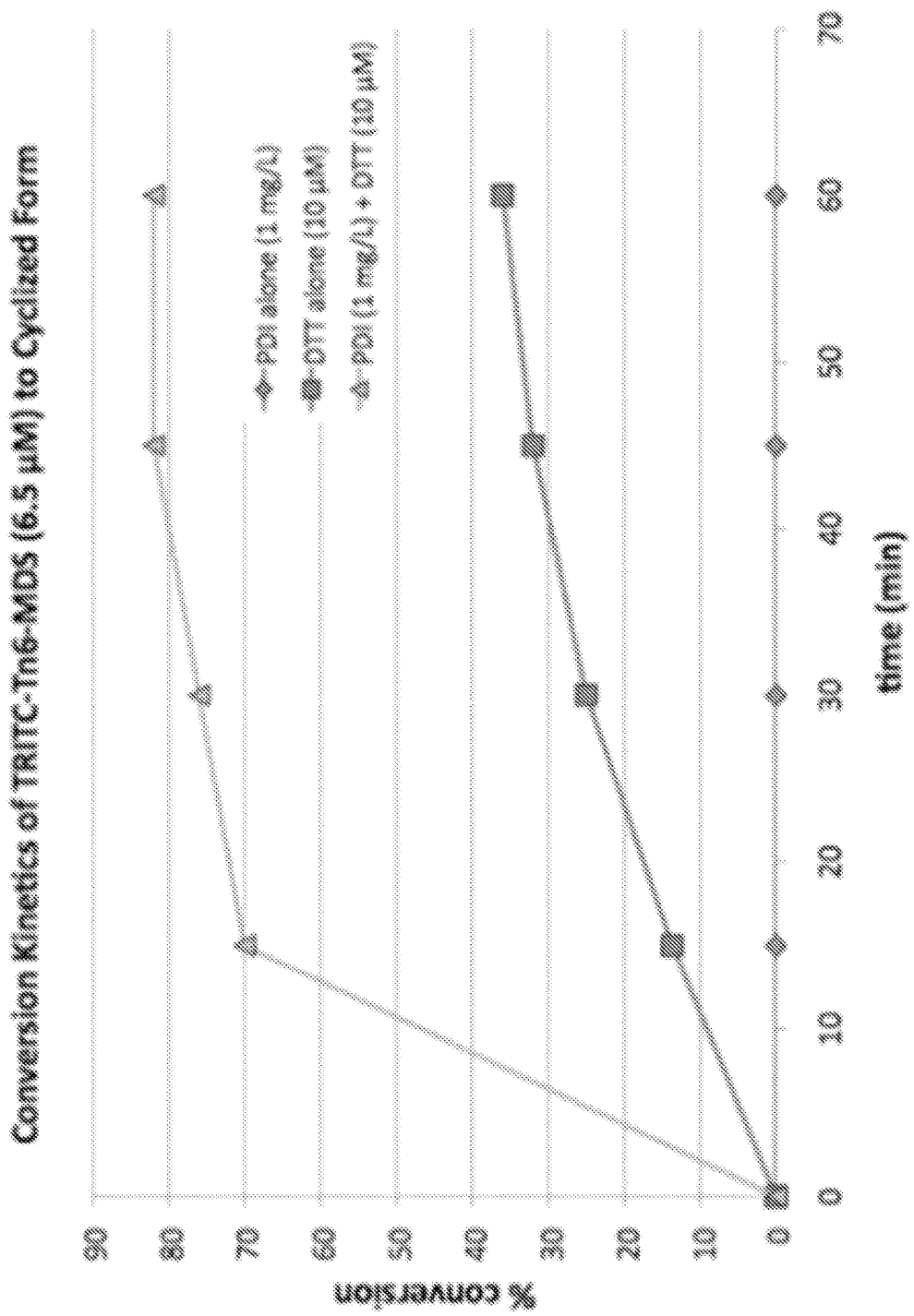

This mixed disulfide (MDS) probe, denoted as TRITC-Tn6-MDS, was then tested to determine whether it could be recognized as a substrate by PDI. Conversion of the probe from the mixed-disulfide (MDS) form to the cyclized form was followed by LC-MS under three sets of reaction conditions (PDI alone; DTT alone; and PDI+DTT). The assay buffer for these experiments was 50 mM TRIS, 100 mM NaCl, 2 mM CaCl, and 0.1% Triton X-100. PDI alone does not promote cyclization of the probe, but PDI in the presence of a reducing agent like dithiothreitol (DTT) promotes rapid conversion of the probe to the desired product compared to DTT alone (FIG. 15A and FIG. 15B).

Binding Constants

Figure 16:
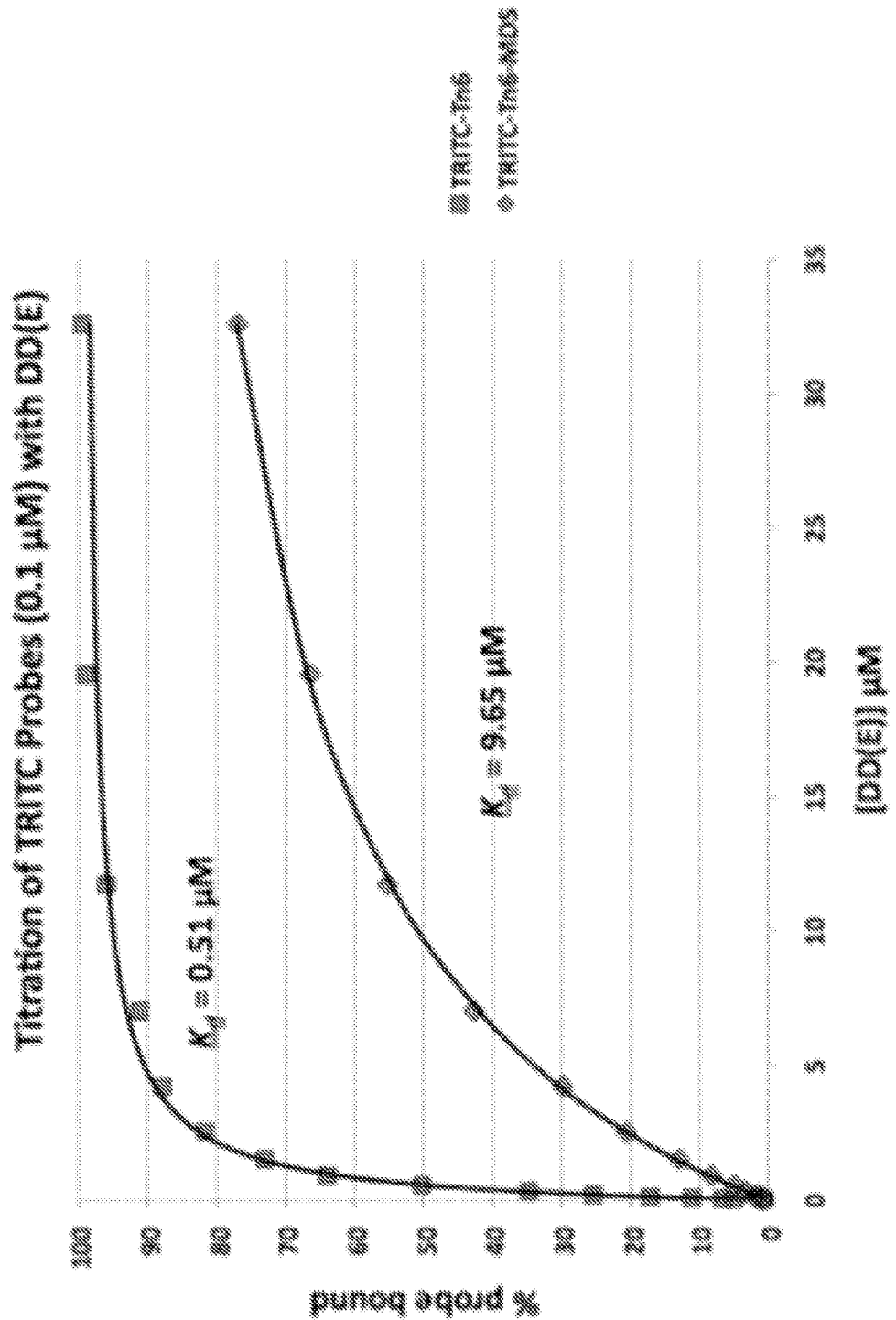
FIG. 16 shows binding curves of a linear TRITC-Tn6-MDS probe and the corresponding cyclic form determined by measuring the change in fluorescence anisotropy that occurs upon binding to DD(E).

The binding constants of the TRITC-Tn6-MDS probe and its activated cyclic form were then measured with the fibrin fragment DD(E). A serial dilution of the DD(E) protein was prepared and then mixed with the two probes. The binding curves were then measured by fluorescence anisotropy, shown in FIG. 16. The TRITC-Tn6-MDS probe had a Kd value that was roughly 20-fold greater than that of the cyclic form. Therefore, the disulfide linkage of this probe can act as a switch for binding.

Real-Time Assay

Figure 17:
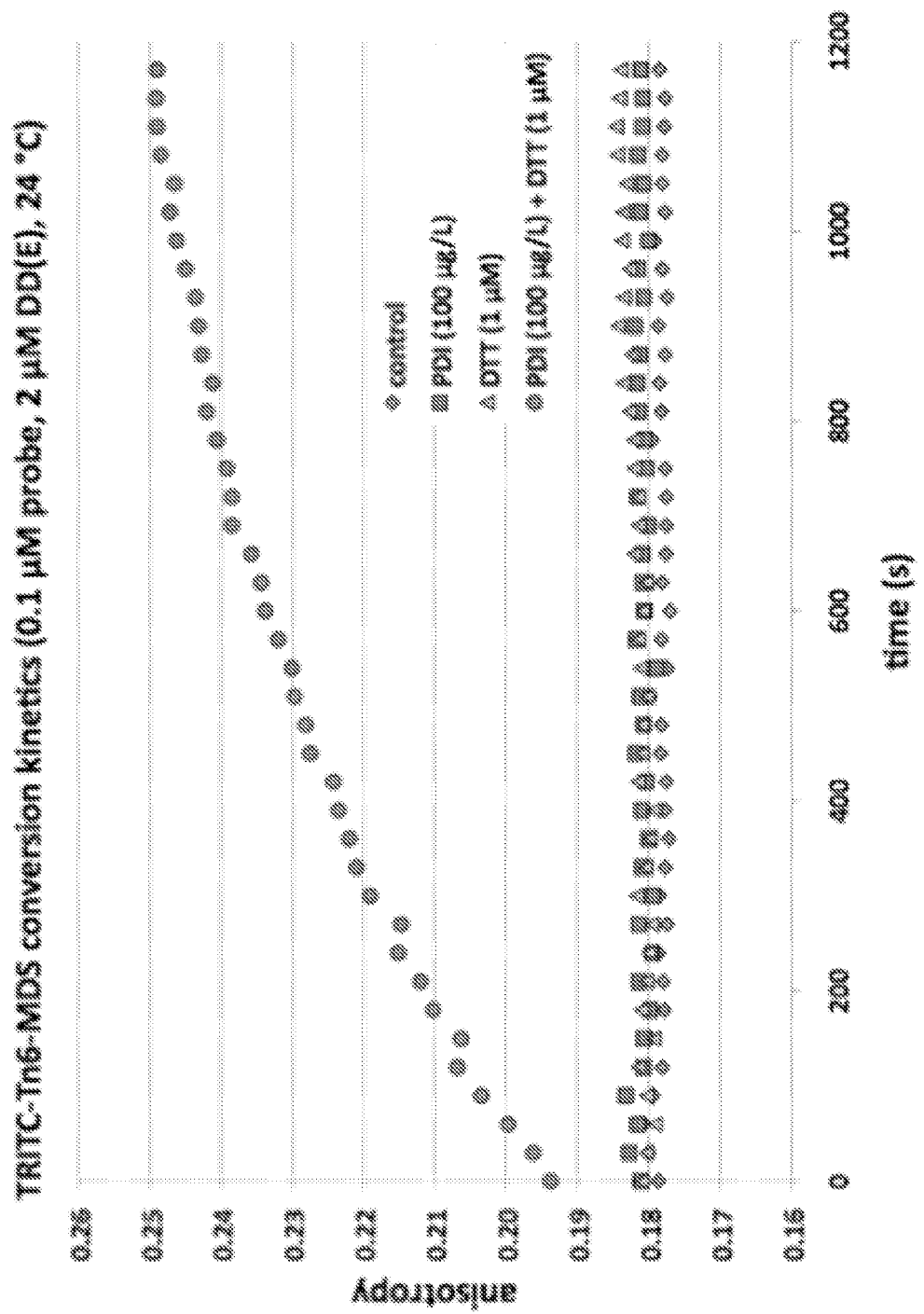
FIG. 17 illustrates a real-time assay showing the conversion of a linear TRITC-Tn6-MDS probe to cyclic TRITC-Tn6, which binds DD(E) leading to an increase in fluorescence anisotropy.

A real-time assay was also developed to show that the activation of the TRITC -Tn6-MDS probe was dependent on the presence of PDI activity. These experiments were conducted in the same assay buffer as was used for the LC-MS experiment described above. The reactions were run in the presence of 2 µM DD(E) and followed by monitoring the change in fluorescence anisotropy that occurs as the inactive form of the probe becomes cyclized and then binds to DD(E). Under these conditions, it is evident that only when both PDI and DTT are present simultaneously that the probe is efficiently activated. Results of the real-time assay are shown in FIG. 17.

Example 10. In vivo Positron Emission Tomography (PET) Imaging

In vivo studies were performed in a rat model of arterial thrombosis induced by ferric chloride application. Briefly, adult male Sprague-Dawley rats (250-300 g, Charles River Laboratories) were anesthetized with isoflurane (4% induction, 2-2.5% maintenance, in medical air), and a midline neck incision was performed to expose the right common carotid artery. A small piece of filter paper (Whatman #1; size: 2×1 mm) was soaked for 1 min in a solution of ferric chloride (Sigma, 25% w/v, in sterile saline), and then applied on the vessel for 5 min to induce thrombosis. At the end of the procedure, the surgical site was rinsed with sterile saline to remove the excess of ferric chloride, and the formation of the clot was confirmed by visual inspection. Femoral artery and vein catheterization was performed to collect blood samples and to deliver the probe, respectively. Approximately 15-30 min after the induction of thrombosis, the animals were injected with the molecular probe FBP14.

PET scans were performed with a dedicated small-animal PET/SPECT/CT scanner (Triumph; TriFoil Imaging), equipped with gas anesthesia and heating system. Instrument calibration was performed each day by scanning a phantom of known activity. After carotid artery induction, rats were transferred into the scanner and imaged for 90 min immediately after the injection of the probe. The PET field of view was 80 mm and covered the head to the base of the heart with the neck at the isocenter. Images were acquired over 6 min with 512 projections with 3 frames per projection (exposure time per frame, ~200 ms; peak tube voltage, 70 kV; tube current, 177 mA).

Figure 18:
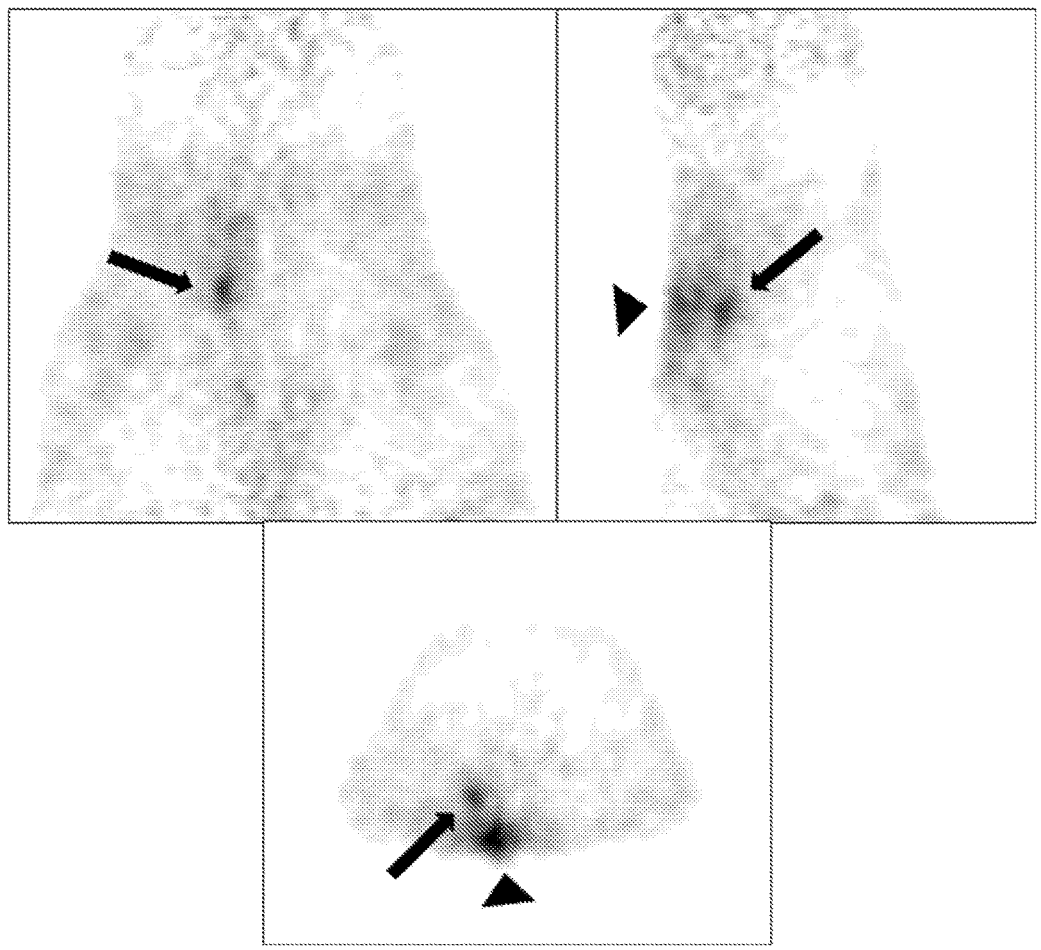
FIG. 18 shows three representative PET image scans. The images show orthogonal image planes that bisect the thrombus. The images are from the 45-90 min reconstruction. Arrows denote an area of high radioactivity in the location of the ferric chloride injury to the carotid artery (thrombus). The arrowhead shows a region of superficial high radioactivity corresponding to the site of the surgical incision and associated fresh thrombi.

PET and CT images were reconstructed using the LabPET software (TriFoil Imaging) to a voxel size of 0.5×0.5×0.6 mm$^3$ (PET) and isotropic 0.3 mm$^3$ (CT), and are shown in FIG. 18. Data obtained from the 90 min scan were framed into a dynamic sequence of 10×60, 10×180 and 5'600 seconds; an additional image was reconstructed from the 45-90 min data. Data of each frame were reconstructed employing an iterative algorithm (maximum-likelihood expectation-maximization (MLEM), 30 iterations). All images were corrected for decay, randoms, and dead time; CT data was used to provide for attenuation correction. Results were expressed as percent of injected dose per cubic centimeter of tissue (% ID/cc).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound, which is:
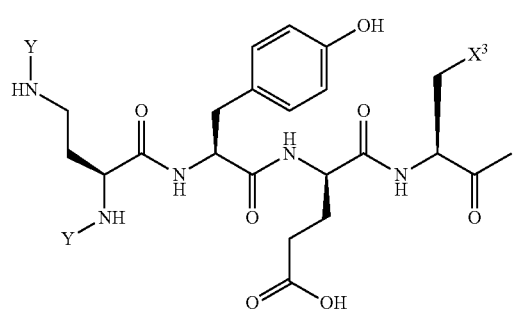
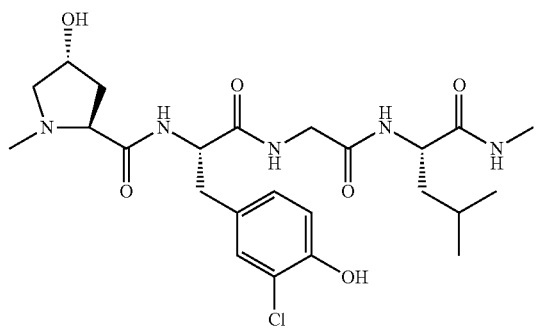
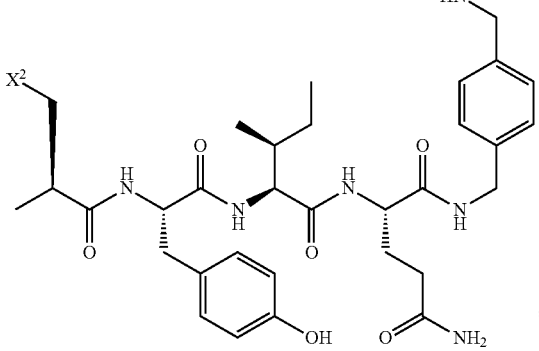
or a pharmaceutically acceptable salt thereof, wherein:
$X^1$ and $X^2$ are each
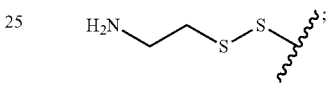
and Y is
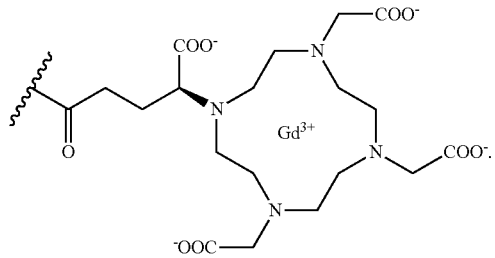
2. A pharmaceutical composition, comprising a compound of claim 1, or a pharmaceutically acceptable salt thereof, and one or more pharmaceutically acceptable carriers.
* * * * *

SEQUENCE LISTING

```
<160> NUMBER OF SEQ ID NOS: 218

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Gln Pro Cys Pro Trp Glu Ser Trp Thr Phe Cys Trp Asp Pro
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Gln Pro Cys Pro Ala Glu Ser Trp Thr Phe Cys Trp Asp Pro
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Pro Pro Gly Trp Gln Pro Cys Pro Trp Glu Ser Trp Thr Phe Cys
1               5                   10                  15

Trp Asp Pro

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Arg Gly Trp Gln Pro Cys Pro Trp Glu Ser Trp Thr Phe Cys
```

Trp Asp Pro

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Trp Gln Pro Cys Pro Trp Glu Ser Trp Thr Phe Cys Trp Asp Pro
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Ser Gly Thr Trp Gln Pro Cys Pro Trp Glu Ser Trp Thr Phe
1               5                   10                  15

Cys Trp Asp Pro
            20

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 2-cyclohexyl-L-alanine

<400> SEQUENCE: 7

Trp Gln Pro Cys Pro Trp Glu Ser Trp Thr Xaa Cys Trp Asp Pro
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: L-4-fluorophenylalanine

<400> SEQUENCE: 8

Trp Gln Pro Cys Pro Trp Glu Ser Trp Thr Xaa Cys Trp Asp Pro
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (11)..(11)
<223> OTHER INFORMATION: L-3,4-difluorophenylalanine

<400> SEQUENCE: 9

Trp Gln Pro Cys Pro Trp Glu Ser Trp Thr Xaa Cys Trp Asp Pro
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Gly Trp Gln Pro Cys Pro Trp Glu Ser Trp Thr Phe Cys Trp Asp
1               5                   10                  15

Pro

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Trp Gln Pro Cys Pro Trp Glu Ser Trp Thr Phe Cys Trp Asp Pro
1               5                   10                  15

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Ser Gly Ser Gly Ser Gly Trp Gln Pro Cys Pro Trp Glu Ser
1               5                   10                  15

Trp Thr Phe Cys Trp Asp Pro
            20

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Lys Gly Trp Gln Pro Cys Pro Trp Glu Ser Trp Thr Phe Cys Trp
1               5                   10                  15

Asp Pro

<210> SEQ ID NO 14
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 14

Lys Gly Lys Gly Lys Gly Trp Gln Pro Cys Pro Trp Glu Ser Trp Thr
1               5                   10                  15

Phe Cys Trp Asp Pro
            20

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Trp Gln Pro Cys Pro Trp Glu Ser Trp Thr Phe Cys Trp Asp Pro
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term 1-(tetrahydrofuran-2-yl)methan-1-onyl
      modified

<400> SEQUENCE: 16

Trp Gln Pro Cys Pro Trp Glu Ser Trp Thr Phe Cys Trp Asp Pro
1               5                   10                  15

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Gly Gly Trp Gln Pro Cys Pro Trp Glu Ser Trp Thr Phe Cys
1               5                   10                  15

Trp Asp Pro

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Thr Trp Gln Pro Cys Pro Trp Glu Ser Trp Thr Phe Cys Trp Asp
1               5                   10                  15

Pro

<210> SEQ ID NO 19
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: trans-4-hydroxy-L-proline

<400> SEQUENCE: 19

Trp Gln Pro Cys Xaa Trp Glu Ser Trp Thr Phe Cys Trp Asp Pro
1               5                   10                  15

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Pro Pro Gly Trp Gln Pro Cys Pro Ala Glu Ser Trp Thr Phe Cys
1               5                   10                  15

Trp Asp Pro

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Arg Gly Trp Gln Pro Cys Pro Ala Glu Ser Trp Thr Phe Cys
1               5                   10                  15

Trp Asp Pro

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Lys Gly Trp Gln Pro Cys Pro Ala Glu Ser Trp Thr Phe Cys Trp
1               5                   10                  15

Asp Pro

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Gly Lys Gly Lys Gly Trp Gln Pro Cys Pro Ala Glu Ser Trp Thr
1               5                   10                  15

Phe Cys Trp Asp Pro
            20
```

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Trp Gln Pro Cys Pro Ala Glu Ser Trp Thr Phe Cys Trp Asp Pro
1               5                   10                  15

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Gly Ser Gly Ser Gly Ser Gly Trp Gln Pro Cys Pro Ala Glu Ser
1               5                   10                  15

Trp Thr Phe Cys Trp Asp Pro
            20

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: L-4-fluorophenylalanine

<400> SEQUENCE: 26

Trp Gln Pro Cys Pro Ala Glu Ser Trp Thr Xaa Cys Trp Asp Pro
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 2-cyclohexyl-L-alanine

<400> SEQUENCE: 27

Trp Gln Pro Cys Pro Ala Glu Ser Trp Thr Xaa Cys Trp Asp Pro
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)

<223> OTHER INFORMATION: L-3,4-difluorophenylalanine

<400> SEQUENCE: 28

Trp Gln Pro Cys Pro Ala Glu Ser Trp Thr Xaa Cys Trp Asp Pro
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term 1-(tetrahydrofuran-2-yl)methan-1-onyl
      modified

<400> SEQUENCE: 29

Trp Gln Pro Cys Pro Ala Glu Ser Trp Thr Phe Cys Trp Asp Pro
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Gly Ser Gly Thr Trp Gln Pro Cys Pro Ala Glu Ser Trp Thr Phe
1               5                   10                  15

Cys Trp Asp Pro
            20

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Gly Gly Trp Gln Pro Cys Pro Ala Glu Ser Trp Thr Phe Cys
1               5                   10                  15

Trp Asp Pro

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: trans-4-hydroxy-L-proline

<400> SEQUENCE: 32

Arg Arg Gly Gly Trp Gln Pro Cys Xaa Trp Glu Ser Trp Thr Phe Cys
1               5                   10                  15

Trp Asp Pro

```
<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term Fmoc-8-amino-3,6-dioxaoctanoic acid
      modified
<220> FEATURE:
<221> NAME/KEY: MOD_RES
<222> LOCATION: (12)..(12)
<223> OTHER INFORMATION: 2-cyclohexyl-L-alanine

<400> SEQUENCE: 33

Ser Trp Gln Pro Cys Pro Ala Glu Ser Trp Thr Xaa Cys Trp Asp Pro
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: 2-cyclohexyl-L-alanine

<400> SEQUENCE: 34

Gly Trp Gln Pro Cys Pro Ala Glu Ser Trp Thr Xaa Cys Trp Asp Pro
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Gly Trp Gln Pro Cys Pro Ala Glu Ser Trp Thr Phe Cys Trp Asp
1               5                   10                  15

Pro

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: 2-cyclohexyl-L-alanine

<400> SEQUENCE: 36

Arg Gly Trp Gln Pro Cys Pro Ala Glu Ser Trp Thr Xaa Cys Trp Asp
1               5                   10                  15

Pro

<210> SEQ ID NO 37
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ser Trp Gln Pro Cys Pro Ala Glu Ser Trp Thr Phe Cys Trp Asp
1               5                   10                  15

Pro

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp, Tyr, Phe, Ser, Biphenylalanine,
      Diaminopropionic acid, Homophenylalanine, 3-pyridylalanine,
      4-pyridylalanine, 3,4-Dimethoxyphenylalanine, Nor-Tyr, D-Trp,
      D-Phe, Phe(3/4*), or Tyr(3*), wherein Phe(3/4*) is a phenylalanine
      (Cont'd)
<220> FEATURE:
<221> NAME/KEY: MOD_RES
<222> LOCATION: (1)..(1)
<223> OTHER INFORMATION: Cont'd from above: substituted at either the 3
      or the 4 position with a moiety such as CH3, CF3, NH2, CH2NH2, CN,
      F, Cl, Br, I, Et, or Orne, and Tyr(3*) is a tyrosine substituted
      at the 3 position with a moiety such as F, Cl, Br, I, and NO2.
<220> FEATURE:
<221> NAME/KEY: MISC_FEATURE
<222> LOCATION: (1)..(1)
<223> OTHER INFORMATION: This position may or may not be present. If
      not present N-term may be modified by Hexanoic acid,
      cytosine-PNA, Guanosine-PNA, or Adenosine-PNA
<220> FEATURE:
<221> NAME/KEY: MOD_RES
<222> LOCATION: (2)..(2)
<223> OTHER INFORMATION: Glu, His, D-Glu, Ser, His(Bzl),
      2-pyridylalanine, Diaminopropionic acid, or
      Thiazolidine-4-carboxylic acid
<220> FEATURE:
<221> NAME/KEY: MOD_RES
<222> LOCATION: (6)..(6)
<223> OTHER INFORMATION: Gly or Asp
<220> FEATURE:
<221> NAME/KEY: MOD_RES
<222> LOCATION: (9)..(9)
<223> OTHER INFORMATION: His, Phe, Tyr, or Trp
<220> FEATURE:
<221> NAME/KEY: MOD_RES
<222> LOCATION: (10)..(10)
<223> OTHER INFORMATION: Ile, Leu, Val, Asn, 4-Benzoyl-Phe,
      Beta-alanine, Homophenylalanine, Nor-Leu, Tert-leucine, Nor-Val,
      phenylglycine, 2-cyclohexyl-L-alanine, 4-thiazoylalanine,
      2-furylalanine, Thiazolidine-4-carboxylic acid, (Cont'd)
<220> FEATURE:
<221> NAME/KEY: MOD_RES
<222> LOCATION: (10)..(10)
<223> OTHER INFORMATION: Cont'd from above: 4-pyridylalanine, or
      Phe(3/4*), wherein Phe(3/4*) is a phenylalanine substituted at
      either the 3 or the 4 position with a moiety such as CF3, Et, iPr,
      or OMe
<220> FEATURE:
<221> NAME/KEY: MOD_RES
<222> LOCATION: (11)..(11)
<223> OTHER INFORMATION: Asn, Gln, Ile, Leu, Val, or not present
<220> FEATURE:
<223> OTHER INFORMATION: See specification as filed for detailed
      description of substitutions and preferred embodiments
```

```
<400> SEQUENCE: 38

Xaa Xaa Cys Pro Tyr Xaa Leu Cys Xaa Xaa Xaa
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 39

Trp Glu Cys Pro Tyr Gly Leu Cys Trp Ile Gln
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 40

Tyr Glu Cys Pro Tyr Gly Leu Cys Tyr Ile Gln
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 41

Tyr Glu Cys Pro Tyr Gly Leu Cys Trp Ile Gln
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 42

Trp Glu Cys Pro Tyr Gly Leu Cys Tyr Ile Gln
1               5                   10

<210> SEQ ID NO 43
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 43

Trp Glu Cys Pro Tyr Asp Leu Cys Trp Ile Gln
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 44

Tyr Glu Cys Pro Tyr Asp Leu Cys Tyr Ile Gln
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 45

Tyr Glu Cys Pro Tyr Asp Leu Cys Trp Ile Gln
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 46

Trp Glu Cys Pro Tyr Asp Leu Cys Tyr Ile Gln
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Phe His Cys Pro Tyr Asp Leu Cys His Ile Leu
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr His Cys Pro Tyr Gly Leu Cys Trp Ile Gln
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 49

Trp Glu Cys Pro Tyr Gly Leu Cys Trp Ile Gln
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 50

Trp Glu Cys Pro Tyr Gly Leu Cys Trp Ile Gln
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Phe His Cys Pro Tyr Asp Leu Cys His Ile Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

Phe His Cys Pro Tyr Asp Leu Cys His Ile
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 4-Benzoyl-Phe

<400> SEQUENCE: 53

Phe His Cys Pro Tyr Asp Leu Cys His Xaa
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Homophenylalanine

<400> SEQUENCE: 54

Phe His Cys Pro Tyr Asp Leu Cys His Xaa
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 4-Benzoyl-Phe

<400> SEQUENCE: 55

Phe His Cys Pro Tyr Asp Leu Cys His Xaa
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr His Cys Pro Tyr Asp Leu Cys His Ile
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Phe His Cys Pro Tyr Asp Leu Cys His Ile Leu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 4-Benzoyl-Phe

<400> SEQUENCE: 58

Phe His Cys Pro Tyr Asp Leu Cys His Xaa
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe His Cys Pro Tyr Asp Leu Cys His Ile
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Phe His Cys Pro Tyr Asp Leu Cys His Ile
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-pyridylalanine

<400> SEQUENCE: 61

Xaa His Cys Pro Tyr Asp Leu Cys His Ile
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: 4-pyridylalanine

<400> SEQUENCE: 62

Xaa His Cys Pro Tyr Asp Leu Cys His Ile
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe His Cys Pro Tyr Asp Leu Cys His Ile
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr His Cys Pro Tyr Asp Leu Cys His Ile
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe His Cys Pro Tyr Asp Leu Cys His Ile Leu
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 4-Benzoyl-Phe

<400> SEQUENCE: 66

Phe His Cys Pro Tyr Asp Leu Cys His Xaa Leu
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (10)..(10)
<223> OTHER INFORMATION: 4-Benzoyl-Phe

<400> SEQUENCE: 67

Phe His Cys Pro Tyr Asp Leu Cys His Xaa Leu
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe His Cys Pro Tyr Asp Leu Cys His Ile Leu
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-naphthylalanine

<400> SEQUENCE: 69

Xaa His Cys Pro Tyr Asp Leu Cys His Ile
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr His Cys Pro Tyr Asp Leu Cys His Ile
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 4-Benzoyl-Phe

<400> SEQUENCE: 71

Phe His Cys Pro Tyr Asp Leu Cys His Xaa
1               5                   10

<210> SEQ ID NO 72
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 72

Phe His Cys Pro Tyr Asp Leu Cys His Ile
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 3-pyridylalanine

<400> SEQUENCE: 73

Phe His Cys Pro Tyr Asp Leu Cys Xaa Ile
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe His Cys Pro Tyr Asp Leu Cys His Ile
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe His Cys Pro Tyr Asp Leu Cys His Ile
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Phe His Cys Pro Tyr Asp Leu Cys His Ile
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Phe His Cys Pro Tyr Asp Leu Cys His Ile
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe His Cys Pro Tyr Asp Leu Cys His Ile
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr His Cys Pro Tyr Asp Leu Cys His Ile
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr His Cys Pro Tyr Asp Leu Cys His Ile
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe His Cys Pro Tyr Asp Leu Cys His Ile
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe His Cys Pro Tyr Asp Leu Cys His Ile
1               5                   10

<210> SEQ ID NO 83
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 83

Phe His Cys Pro Tyr Asp Leu Cys His Ile
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-Dimethoxyphenylalanine

<400> SEQUENCE: 84

Xaa His Cys Pro Tyr Asp Leu Cys His Ile
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Phe His Cys Pro Tyr Asp Leu Cys His Ile
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Phe His Cys Pro Tyr Asp Leu Cys His Ile
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Phe His Cys Pro Tyr Asp Leu Cys His Ile
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Phe His Cys Pro Tyr Asp Leu Cys His Phe
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Phe His Cys Pro Tyr Asp Leu Cys His Ile
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe His Cys Pro Tyr Asp Leu Cys His Ile
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Homophenylalanine

<400> SEQUENCE: 91

Xaa His Cys Pro Tyr Asp Leu Cys His Ile
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nor-Tyr

<400> SEQUENCE: 92

Xaa His Cys Pro Tyr Asp Leu Cys His Ile
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Glu Cys Pro Tyr Gly Leu Cys Trp Ile Gln
```

```
1               5                   10
```

```
<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Phe His Cys Pro Tyr Asp Leu Cys His Ile Leu
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe His Cys Pro Tyr Asp Leu Cys His Ile
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Nor-Leu

<400> SEQUENCE: 96

Phe His Cys Pro Tyr Asp Leu Cys His Xaa
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Tert-leucine

<400> SEQUENCE: 97

Phe His Cys Pro Tyr Asp Leu Cys His Xaa
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Phe His Cys Pro Tyr Asp Leu Cys His Phe
1               5                   10
```

```
<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: biphenylalanine

<400> SEQUENCE: 99

Phe His Cys Pro Tyr Asp Leu Cys His Xaa
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Phe His Cys Pro Tyr Asp Leu Cys His Phe
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Phe His Cys Pro Tyr Asp Leu Cys His Phe
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Phe His Cys Pro Tyr Asp Leu Cys His Phe
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Phe His Cys Pro Tyr Asp Leu Cys His Ile
1               5                   10

<210> SEQ ID NO 104
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 104

Phe His Cys Pro Tyr Asp Leu Cys His Ile Leu
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Trp Glu Cys Pro Tyr Gly Leu Cys Trp Ile Gln
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 106

Thr Glu Cys Pro Tyr Gly Leu Cys Trp Ile Gln
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Phe His Cys Pro Tyr Asp Leu Cys His Ile Leu
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr His Cys Pro Tyr Asp Leu Cys His Ile
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 109

Trp Glu Cys Pro Tyr Gly Leu Cys His Ile Gln
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Glu

<400> SEQUENCE: 110

Phe Glu Cys Pro Tyr Gly Leu Cys Trp Ile Gln
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Glu Cys Pro Tyr Gly Leu Cys Tyr Ile Gln
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Trp Glu Cys Pro Tyr Gly Leu Cys Phe Ile Gln
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 113

His Glu Cys Pro Tyr Gly Leu Cys Trp Ile Gln
1               5                   10

<210> SEQ ID NO 114
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 114

Phe His Cys Pro Tyr Asp Leu Cys His Ile Leu
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Trp Glu Cys Pro Tyr Gly Leu Cys Trp Ile Gln
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Nor-Val

<400> SEQUENCE: 116

Phe His Cys Pro Tyr Asp Leu Cys His Xaa
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: phenylglycine

<400> SEQUENCE: 117

Phe His Cys Pro Tyr Asp Leu Cys His Xaa
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Phe His Cys Pro Tyr Asp Leu Cys His Phe
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (9)..(9)
<223> OTHER INFORMATION: 4-pyridylalanine

<400> SEQUENCE: 119

Phe His Cys Pro Tyr Asp Leu Cys Xaa Ile
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 120

Ser Glu Cys Pro Tyr Gly Leu Cys Trp Ile Gln
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Trp Glu Cys Pro Tyr Gly Leu Cys Tyr Ile Gln
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Tyr Glu Cys Pro Tyr Gly Leu Cys Trp Ile Gln
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 123

Phe Glu Cys Pro Tyr Gly Leu Cys Trp Ile Gln
1               5                   10

<210> SEQ ID NO 124
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 124

Phe His Cys Pro Tyr Asp Leu Cys His Ile Leu
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Phe His Cys Pro Tyr Asp Leu Cys His Ile Leu
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: 4-Benzoyl-Phe

<400> SEQUENCE: 126

Phe His Cys Pro Tyr Asp Leu Cys His Xaa
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Phe His Cys Pro Tyr Gly Leu Cys His Ile Leu
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser His Cys Pro Tyr Asp Leu Cys His Ile Leu
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 129

His Glu Cys Pro Tyr Gly Leu Cys His Ile Gln
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Phe His Cys Pro Tyr Asp Leu Cys His Ile Leu
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 4-Benzoyl-Phe

<400> SEQUENCE: 131

Phe His Cys Pro Tyr Asp Leu Cys Xaa Ile
1               5                   10

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

His Cys Pro Tyr Asp Leu Cys His Ile
1               5

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Phe His Cys Pro Tyr Phe Leu Cys His Ile Leu
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Phe Glu Cys Pro Tyr Gly Leu Cys Trp Ile Gln
1               5                   10
```

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-naphthylalanine

<400> SEQUENCE: 135

Phe His Cys Pro Tyr Xaa Leu Cys His Ile Leu
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Phe His Cys Pro Tyr Asp Leu Cys His Ile Leu
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Homophenylalanine

<400> SEQUENCE: 137

Xaa His Cys Pro Tyr Asp Leu Cys His Ile Leu
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: biphenylalanine

<400> SEQUENCE: 138

Xaa His Cys Pro Tyr Asp Leu Cys His Ile Leu
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Trp Glu Cys Pro Tyr Gly Leu Cys Trp Ile Gln
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Phe Trp Cys Pro Tyr Asp Leu Cys His Ile
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 2-pyridylalanine

<400> SEQUENCE: 141

Phe His Cys Pro Tyr Asp Leu Cys Xaa Ile
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 4-thiazoylalanine

<400> SEQUENCE: 142

Phe His Cys Pro Tyr Asp Leu Cys Xaa Ile
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: dihydrotryptophane

<400> SEQUENCE: 143

Phe His Cys Pro Tyr Asp Leu Cys Xaa Ile
1               5                   10

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 144

His Cys Pro Tyr Asp Leu Cys His Ile
1               5

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gly or Asp
<220> FEATURE:
<223> OTHER INFORMATION: See specification as filed for detailed
      description of substitutions and preferred embodiments

<400> SEQUENCE: 145

Cys Pro Tyr Xaa Leu Cys
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: n(decyl)Gly, n(4-PhBu)Gly, methyl-Leu,
      4-Benzoyl-Phe, Biphenylalanine, Me-Biphenylalanine, Phe(4*),
      Phe(3-Me), Phe(3, 4-difiuoro), 4-amino-6-methylheptanoic acid,
      Homophenylalanine, Tyr(3,5-di-iodo), (cont'd below)
<220> FEATURE:
<221> NAME/KEY: MOD_RES
<222> LOCATION: (8)..(8)
<223> OTHER INFORMATION: Cont'd from above: Pentafluorophenylalanine,
      1-naphthylalanine, D-1-naphthylalanine, or methyl-Leu wherein
      Phe(4*) is a phenylalanine substituted at the 4 position with a
      moiety selected from the group consisting of Et, CF3, I, and iPr
<220> FEATURE:
<223> OTHER INFORMATION: See specification as filed for detailed
      description of substitutions and preferred embodiments

<400> SEQUENCE: 146

Cys Asp Tyr Tyr Gly Thr Cys Xaa
1               5

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any natural or non-natural amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Asp, D-Asp, beta-Asp, isonipecotic acid,
      Nipecotic acid, Me-Asp, D-Cys, 2-carboxymorpholine, or carboxymethylpiperdine
<220> FEATURE:
<223> OTHER INFORMATION: See specification as filed for detailed
      description of substitutions and preferred embodiments

<400> SEQUENCE: 147

Xaa Pro Cys Asp Tyr Tyr Gly Thr Cys Xaa Xaa
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: D-Asp

<400> SEQUENCE: 148

Leu Pro Cys Asp Tyr Tyr Gly Thr Cys Gly Asp
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Leu Pro Cys Asp Tyr Tyr Gly Thr Cys Gly Asp
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: biphenylalanine

<400> SEQUENCE: 150

Leu Pro Cys Asp Tyr Tyr Gly Thr Cys Xaa Asp
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: biphenylalanine
<220> FEATURE:
<221> NAME/KEY: MOD_RES
<222> LOCATION: (11)..(11)
<223> OTHER INFORMATION: D-Asp

<400> SEQUENCE: 151

Leu Pro Cys Asp Tyr Tyr Gly Thr Cys Xaa Asp
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: isonipecotic acid

<400> SEQUENCE: 152

Leu Pro Cys Asp Tyr Tyr Gly Thr Cys Leu Xaa
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: carboxymethylpiperdine

<400> SEQUENCE: 153

Leu Pro Cys Asp Tyr Tyr Gly Thr Cys Leu Xaa
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: N-methylbiphenylalanine

<400> SEQUENCE: 154

Leu Pro Cys Asp Tyr Tyr Gly Thr Cys Xaa Asp
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: D-Asp

<400> SEQUENCE: 155

Leu Pro Cys Asp Tyr Tyr Gly Thr Cys Gly Asp
1               5                   10

<210> SEQ ID NO 156
<211> LENGTH: 11
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 156

Leu Pro Cys Asp Tyr Tyr Gly Thr Cys Gly Asp
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: isonipecotic acid

<400> SEQUENCE: 157

Leu Pro Cys Asp Tyr Tyr Gly Thr Cys Leu Xaa
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: biphenylalanine

<400> SEQUENCE: 158

Leu Pro Cys Asp Tyr Tyr Gly Thr Cys Xaa Asp
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: biphenylalanine
<220> FEATURE:
<221> NAME/KEY: MOD_RES
<222> LOCATION: (11)..(11)
<223> OTHER INFORMATION: D-Asp

<400> SEQUENCE: 159

Leu Pro Cys Asp Tyr Tyr Gly Thr Cys Xaa Asp
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)

```
<223> OTHER INFORMATION: N-methylbiphenylalanine

<400> SEQUENCE: 160

Leu Pro Cys Asp Tyr Tyr Gly Thr Cys Xaa Asp
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: carboxymethylpiperdine

<400> SEQUENCE: 161

Leu Pro Cys Asp Tyr Tyr Gly Thr Cys Leu Xaa
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Leu Pro Cys Asp Tyr Tyr Gly Thr Cys Leu Asp
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-cyclohexyl-L-alanine
<220> FEATURE:
<221> NAME/KEY: MOD_RES
<222> LOCATION: (10)..(10)
<223> OTHER INFORMATION: biphenylalanine

<400> SEQUENCE: 163

Xaa Pro Cys Asp Tyr Tyr Gly Thr Cys Xaa Asp
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Glu

<400> SEQUENCE: 164

Tyr Glu Cys Pro Tyr Gly Leu Cys Tyr Ile Gln
1               5                   10
```

```
<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: 2-cyclohexyl-L-alanine

<400> SEQUENCE: 165

Arg Trp Gln Pro Cys Pro Ala Glu Ser Trp Thr Xaa Cys Trp Asp Pro
1               5                   10                  15

<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: 2-cyclohexyl-L-alanine

<400> SEQUENCE: 166

Arg Trp Gln Pro Cys Pro Ala Glu Ser Trp Thr Xaa Cys Trp Asp Pro
1               5                   10                  15

Gly Gly Gly Lys
            20

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala, Glu, Phe, Gly, Ile, Lys, Leu, Met, Arg,
      Thr, Val, Tyr, Asn, Asp, Gln, His, Ser, or Thr(phi)
<220> FEATURE:
<221> NAME/KEY: MOD_RES
<222> LOCATION: (3)..(3)
<223> OTHER INFORMATION: Ser, Phe, Ala, or Tyr
<220> FEATURE:
<221> NAME/KEY: MOD_RES
<222> LOCATION: (5)..(5)
<223> OTHER INFORMATION: Gly, Ala, or D-Ala
<220> FEATURE:
<221> NAME/KEY: MOD_RES
<222> LOCATION: (6)..(6)
<223> OTHER INFORMATION: Thr, Val, or Ser
<220> FEATURE:
<223> OTHER INFORMATION: See specification as filed for detailed
      description of substitutions and preferred embodiments

<400> SEQUENCE: 167

Cys Xaa Xaa Tyr Xaa Xaa Cys
1               5

<210> SEQ ID NO 168
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala, Glu, Phe, Gly, Ile, Lys, Leu, Met, Arg,
      Thr, Val, Tyr, Asn, Asp, Gln, His, Ser, or Thr(phi)
<220> FEATURE:
<221> NAME/KEY: MOD_RES
<222> LOCATION: (3)..(3)
<223> OTHER INFORMATION: Ser, Phe, Ala, or Tyr
<220> FEATURE:
<223> OTHER INFORMATION: See specification as filed for detailed
      description of substitutions and preferred embodiments

<400> SEQUENCE: 168

Cys Xaa Xaa Tyr Gly Thr Cys
1               5

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Asp, His, Leu, or Phe
<220> FEATURE:
<221> NAME/KEY: MOD_RES
<222> LOCATION: (2)..(2)
<223> OTHER INFORMATION: Ala, Asp, Gly, Pro, or Ser
<220> FEATURE:
<221> NAME/KEY: MOD_RES
<222> LOCATION: (4)..(4)
<223> OTHER INFORMATION: Ala, Glu, Phe, Gly, Ile, Lys, Leu, Met, Arg,
      Thr, Val, Tyr, Asn, Asp, Gln, His, Ser, or Thr(phi)
<220> FEATURE:
<221> NAME/KEY: MOD_RES
<222> LOCATION: (5)..(5)
<223> OTHER INFORMATION: Ala, Tyr, Phe, or Ser
<220> FEATURE:
<221> NAME/KEY: MOD_RES
<222> LOCATION: (7)..(7)
<223> OTHER INFORMATION: Gly, Ala, or D-Ala
<220> FEATURE:
<221> NAME/KEY: MOD_RES
<222> LOCATION: (8)..(8)
<223> OTHER INFORMATION: Thr, Val, or Ser
<220> FEATURE:
<221> NAME/KEY: MOD_RES
<222> LOCATION: (10)..(10)
<223> OTHER INFORMATION: His, Leu, or Phe
<220> FEATURE:
<221> NAME/KEY: MOD_RES
<222> LOCATION: (11)..(11)
<223> OTHER INFORMATION: Arg, Asp, or His
<220> FEATURE:
<223> OTHER INFORMATION: See specification as filed for detailed
      description of substitutions and preferred embodiments

<400> SEQUENCE: 169

Xaa Xaa Cys Xaa Xaa Tyr Xaa Xaa Cys Xaa Xaa
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (3)..(3)
<223> OTHER INFORMATION: Asn or Asp
<220> FEATURE:
<221> NAME/KEY: MOD_RES
<222> LOCATION: (6)..(6)
<223> OTHER INFORMATION: Gly or Tyr
<220> FEATURE:
<221> NAME/KEY: MOD_RES
<222> LOCATION: (7)..(7)
<223> OTHER INFORMATION: His or Val
<220> FEATURE:
<221> NAME/KEY: MOD_RES
<222> LOCATION: (8)..(8)
<223> OTHER INFORMATION: Pro or Thr(phi)
<220> FEATURE:
<221> NAME/KEY: MOD_RES
<222> LOCATION: (9)..(9)
<223> OTHER INFORMATION: Thr(phi) or Tyr
<220> FEATURE:
<223> OTHER INFORMATION: See specification as filed for detailed
      description of substitutions and preferred embodiments

<400> SEQUENCE: 170

Cys Tyr Xaa Ser Tyr Xaa Xaa Xaa Xaa Cys
1               5                   10

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn or Arg
<220> FEATURE:
<221> NAME/KEY: MOD_RES
<222> LOCATION: (2)..(2)
<223> OTHER INFORMATION: His or Phe
<220> FEATURE:
<221> NAME/KEY: MOD_RES
<222> LOCATION: (3)..(3)
<223> OTHER INFORMATION: Gly or Leu
<220> FEATURE:
<221> NAME/KEY: MOD_RES
<222> LOCATION: (6)..(6)
<223> OTHER INFORMATION: Asn or Asp
<220> FEATURE:
<221> NAME/KEY: MOD_RES
<222> LOCATION: (9)..(9)
<223> OTHER INFORMATION: Gly or Tyr
<220> FEATURE:
<221> NAME/KEY: MOD_RES
<222> LOCATION: (10)..(10)
<223> OTHER INFORMATION: Val or His
<220> FEATURE:
<221> NAME/KEY: MOD_RES
<222> LOCATION: (11)..(11)
<223> OTHER INFORMATION: Pro or Thr(phi)
<220> FEATURE:
<221> NAME/KEY: MOD_RES
<222> LOCATION: (12)..(12)
<223> OTHER INFORMATION: Tyr or Thr(phi)
<220> FEATURE:
<221> NAME/KEY: MOD_RES
<222> LOCATION: (14)..(14)
<223> OTHER INFORMATION: Asp or Ser
<220> FEATURE:
<221> NAME/KEY: MOD_RES
<222> LOCATION: (15)..(15)
<223> OTHER INFORMATION: Tyr or His
<220> FEATURE:
<221> NAME/KEY: MOD_RES
<222> LOCATION: (16)..(16)
```

```
<223> OTHER INFORMATION: Ser or His
<220> FEATURE:
<223> OTHER INFORMATION: See specification as filed for detailed
      description of substitutions and preferred embodiments

<400> SEQUENCE: 171

Xaa Xaa Xaa Cys Tyr Xaa Ser Tyr Xaa Xaa Xaa Xaa Cys Xaa Xaa Xaa
1               5                   10                  15

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr(phi), Phe, His, or Tyr
<220> FEATURE:
<221> NAME/KEY: MOD_RES
<222> LOCATION: (2)..(2)
<223> OTHER INFORMATION: His, Asp, or Glu
<220> FEATURE:
<221> NAME/KEY: MOD_RES
<222> LOCATION: (6)..(6)
<223> OTHER INFORMATION: Asp, Gly, or Ala
<220> FEATURE:
<221> NAME/KEY: MOD_RES
<222> LOCATION: (9)..(9)
<223> OTHER INFORMATION: His, Phe, Tyr, or Thr(phi)
<220> FEATURE:
<221> NAME/KEY: MOD_RES
<222> LOCATION: (10)..(10)
<223> OTHER INFORMATION: Ile, Leu, or Val
<220> FEATURE:
<221> NAME/KEY: MOD_RES
<222> LOCATION: (11)..(11)
<223> OTHER INFORMATION: Asn, Gln, Ile, Leu, or Val
<220> FEATURE:
<223> OTHER INFORMATION: See specification as filed for detailed
      description of substitutions and preferred embodiments

<400> SEQUENCE: 172

Xaa Xaa Cys Pro Tyr Xaa Leu Cys Xaa Xaa Xaa
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Arg Ser Cys Asn Tyr Tyr Gly Thr Cys Leu His
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

His Asp Cys Gln Tyr Tyr Gly Thr Cys Leu His
1               5                   10
```

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Phe Ala Cys His Tyr Tyr Gly Thr Cys Leu His
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Pro Cys Asp Tyr Tyr Gly Thr Cys Phe Asp
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Pro Cys Asp Tyr Tyr Gly Thr Cys Leu Asp
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Phe Ser Cys Thr Tyr Ser Leu His Cys His Arg
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Pro Cys Ser Tyr Tyr Gly Thr Cys Leu His
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 180

Leu Pro Cys Ser Tyr Tyr Gly Thr Cys Leu His
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Leu Ser Cys Asp Tyr Tyr Gly Thr Cys Leu Arg
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Leu Ala Cys His Tyr Tyr Gly Thr Cys Leu His
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Gly Cys His Tyr Tyr Gly Thr Cys Leu His
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Pro Cys Asn Tyr Tyr Gly Thr Cys Leu His
1               5                   10

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asn His Gly Cys Tyr Asn Ser Tyr Gly Val Pro Tyr Cys Asp Tyr Ser
1               5                   10                  15

<210> SEQ ID NO 186
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 186

Arg Phe Leu Cys Tyr Asp Ser Tyr Tyr His Thr Thr Cys Ser His His
1               5                   10                  15

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Thr Phe His Cys Pro Tyr Asp Leu Cys His Ile Leu
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Trp Glu Cys Pro Tyr Gly Leu Cys Thr Ile Gln
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Phe His Cys Pro Tyr Asp Leu Cys His Ile Leu
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Phe His Cys Pro Tyr Asp Leu Cys His Ile Leu
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

His Cys Pro Tyr Asp Leu Cys His Ile Leu
1               5                   10
```

```
<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Phe His Cys Pro Tyr Asp Leu Cys His Ile
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Thr Glu Cys Pro Tyr Gly Leu Cys Thr Ile Gln
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Cys Pro Tyr Gly Leu Cys Thr Ile Gln
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Glu Cys Pro Tyr Gly Leu Cys Thr Ile
1               5                   10

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Pro Cys Asp Tyr Tyr Gly Thr Cys Leu
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 197

Cys Asp Tyr Tyr Gly Thr Cys Leu
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Cys Asp Tyr Tyr Gly Thr Cys
1               5

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Leu Pro Cys Asp Tyr Tyr Asp Ala Thr Cys Leu Asp
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Ala Cys Asp Tyr Tyr Gly Thr Cys Leu Asp
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Leu Pro Cys Ala Tyr Tyr Gly Thr Cys Leu Asp
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Leu Pro Cys Asp Ala Tyr Gly Thr Cys Leu Asp
1               5                   10

<210> SEQ ID NO 203
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Leu Pro Cys Asp Tyr Ala Gly Thr Cys Leu Asp
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Leu Pro Cys Asp Tyr Tyr Ala Thr Cys Leu Asp
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Leu Pro Cys Asp Tyr Tyr Gly Ala Cys Leu Asp
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Leu Pro Cys Asp Tyr Tyr Gly Thr Cys Ala Asp
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Leu Pro Cys Asp Tyr Tyr Gly Ser Cys Leu Asp
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Leu Pro Cys Asp Tyr Tyr Gly Val Cys Ala Asp
```

<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Phe His Cys Pro Tyr Asp Leu Cys His Ile Leu
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Phe His Cys Pro Tyr Asp Leu Cys His Ile Leu
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

His Cys Pro Tyr Asp Leu Cys His Ile Leu
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Phe His Cys Pro Tyr Asp Leu Cys His Ile
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Trp Glu Cys Pro Tyr Gly Leu Cys Thr Ile Gln
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

Glu Cys Pro Tyr Gly Leu Cys Thr Ile Gln
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Trp Glu Cys Pro Tyr Gly Leu Cys Thr Ile
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Phe His Cys Pro Tyr Asp Leu Cys His Ile Gln
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Tyr Asp Glu Cys Pro Tyr Gly Leu Cys Tyr Ile Gln
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gln Trp Glu Cys Pro Tyr Gly Leu Cys Trp Ile Gln
1               5                   10

UNITED STATES PATENT AND TRADEMARK OFFICE
CERTIFICATE OF CORRECTION

PATENT NO. : 10,471,163 B2  
APPLICATION NO. : 14/917733  
DATED : November 12, 2019  
INVENTOR(S) : Galen Loving and Peter D. Caravan Page 1 of 1

It is certified that error appears in the above-identified patent and that said Letters Patent is hereby corrected as shown below:

In the Claims

In Column 191, Line 5, Claim 1, delete "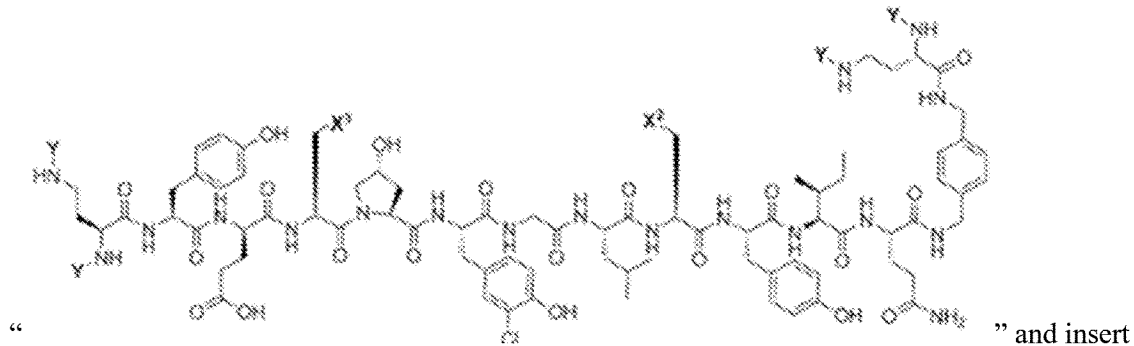" and insert

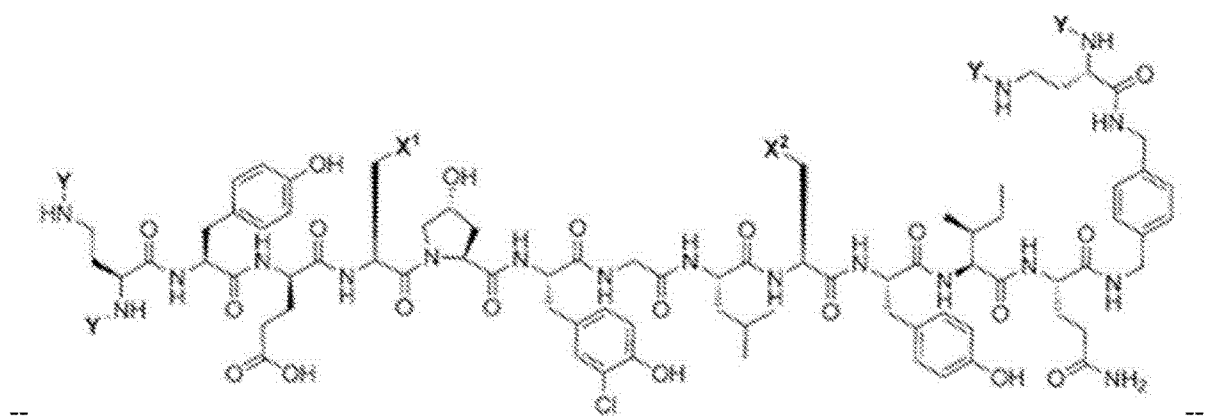

-- --

Signed and Sealed this  
Twenty-ninth Day of June, 2021

Drew Hirshfeld  
*Performing the Functions and Duties of the*  
*Under Secretary of Commerce for Intellectual Property and*  
*Director of the United States Patent and Trademark Office*